US010743886B2

(12) United States Patent
Malkowski et al.

(10) Patent No.: US 10,743,886 B2
(45) Date of Patent: *Aug. 18, 2020

(54) SURGICAL CLIP APPLIER

(71) Applicant: Covidien LP, Mansfield, MA (US)

(72) Inventors: Jaroslaw T. Malkowski, Trumbull, CT (US); Brian Rockrohr, Waterbury, CT (US)

(73) Assignee: Covidien LP, Mansfield, MA (US)

( * ) Notice: Subject to any disclaimer, the term of this patent is extended or adjusted under 35 U.S.C. 154(b) by 275 days.

This patent is subject to a terminal disclaimer.

(21) Appl. No.: 15/818,802

(22) Filed: Nov. 21, 2017

(65) Prior Publication Data

US 2018/0070952 A1    Mar. 15, 2018

Related U.S. Application Data

(63) Continuation of application No. 14/828,588, filed on Aug. 18, 2015, now Pat. No. 9,848,886, which is a
(Continued)

(51) Int. Cl.
*A61B 17/128* (2006.01)
*A61B 17/00* (2006.01)
*A61B 17/29* (2006.01)

(52) U.S. Cl.
CPC .............. *A61B 17/1285* (2013.01); *A61B 2017/00407* (2013.01); *A61B 2017/2943* (2013.01)

(58) Field of Classification Search
CPC ... A61B 17/10; A61B 17/128; A61B 17/1285; A61B 2017/00407; A61B 2017/2943
See application file for complete search history.

(56) References Cited

U.S. PATENT DOCUMENTS 3,120,230 A   2/1964   Skold
3,363,628 A   1/1968   Wood
(Continued)

FOREIGN PATENT DOCUMENTS

AU   2010200641 A1   10/2010
AU   2013254887 A1   11/2013
(Continued)

OTHER PUBLICATIONS

Extended European Search Report issued in corresponding European Application No. EP 16184652 dated Jan. 4, 2017.
(Continued)

*Primary Examiner* — Kathleen S Holwerda
(74) *Attorney, Agent, or Firm* — Carter, DeLuca & Farrell LLP

(57) ABSTRACT

A surgical clip applier is provided and includes a ratchet mechanism having a rack member connected to a drive channel such that axial translation of the drive channel results in axial translation of the rack member, the rack member defining a first set of teeth along a first side thereof and a second set of teeth along a second side thereof. The ratchet mechanism including a first pawl and a second pawl each tiltably supported in the housing and disposed on respective opposed sides of the rack member; and a buckling spring interposed between the first pawl and the second pawl and constrained in a slot formed in the rack member, wherein the buckling spring is dimensioned so as to bow in one of a proximal direction and a distal direction.

9 Claims, 42 Drawing Sheets

Related U.S. Application Data continuation of application No. 13/736,109, filed on Jan. 8, 2013, now Pat. No. 9,113,892.

(56) References Cited

U.S. PATENT DOCUMENTS

| | | |
|---|---|---|
| 3,638,847 A | 2/1972 | Noiles et al. |
| 3,675,688 A | 7/1972 | Bryan et al. |
| 3,735,762 A | 5/1973 | Bryan et al. |
| 3,867,944 A | 2/1975 | Samuels |
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,412,539 A | 11/1983 | Jarvik |
| 4,418,694 A | 12/1983 | Beroff et al. |
| 4,449,531 A | 5/1984 | Cerwin et al. |
| 4,471,780 A | 9/1984 | Menges et al. |
| 4,478,220 A | 10/1984 | Di Giovanni et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,592,498 A | 6/1986 | Braun et al. |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,796,625 A | 1/1989 | Kees, Jr. |
| 4,799,481 A | 1/1989 | Transue et al. |
| 4,815,466 A | 3/1989 | Perlin |
| 4,821,721 A | 4/1989 | Chin et al. |
| 4,822,348 A | 4/1989 | Casey |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,931,058 A | 6/1990 | Cooper |
| 4,934,364 A | 6/1990 | Green |
| 4,951,860 A | 8/1990 | Peters et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,563 A | 11/1991 | Green et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,381,943 A | 1/1995 | Allen et al. |
| 5,382,253 A | 1/1995 | Hogendijk |

(56) References Cited

U.S. PATENT DOCUMENTS

| | | |
|---|---|---|
| 5,382,254 A | 1/1995 | McGarry et al. |
| 5,382,255 A | 1/1995 | Castro et al. |
| 5,383,880 A | 1/1995 | Hooven |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,499 A | 1/1996 | Sorrentino et al. |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,587 A | 5/1997 | Bishop et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,662 A | 9/1997 | Bishop et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A * | 12/1997 | Peyser .............. A61B 17/1285 606/142 |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,749,881 A | 5/1998 | Sackier et al. |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,827,323 A | 10/1998 | Klieman et al. |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,906,625 A | 5/1999 | Bito et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,009,551 A | 12/1999 | Sheynblat |
| 6,017,358 A | 1/2000 | Yoon et al. |
| 6,044,971 A | 4/2000 | Esposito et al. |
| 6,045,560 A | 4/2000 | McKean et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |

(56) References Cited

U.S. PATENT DOCUMENTS

| | | |
|---|---|---|
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,562,051 B1 | 5/2003 | Bolduc et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,656,193 B2 | 12/2003 | Grant et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,357,805 B2 | 4/2008 | Masuda et al. |
| 7,510,562 B2 | 3/2009 | Lindsay |
| 7,552,853 B2 | 6/2009 | Mas et al. |
| 7,585,304 B2 | 9/2009 | Hughett |
| 7,637,917 B2 | 12/2009 | Whitfield et al. |
| 7,644,848 B2 | 1/2010 | Swayze et al. |
| 7,686,820 B2 | 3/2010 | Huitema et al. |
| 7,695,482 B2 | 4/2010 | Viola |
| 7,717,926 B2 | 5/2010 | Whitfield et al. |
| 7,727,248 B2 | 6/2010 | Smith et al. |
| 7,731,724 B2 | 6/2010 | Huitema et al. |
| 7,740,641 B2 | 6/2010 | Huitema |
| 7,752,853 B2 | 7/2010 | Singh et al. |
| 7,753,250 B2 | 7/2010 | Clauson et al. |
| 7,766,207 B2 | 8/2010 | Mather et al. |
| 7,819,886 B2 | 10/2010 | Whitfield et al. |
| 7,887,553 B2 | 2/2011 | Lehman et al. |
| 7,905,890 B2 | 3/2011 | Whitfield et al. |
| 7,942,885 B2 | 5/2011 | Sixto, Jr. et al. |
| 7,952,060 B2 | 5/2011 | Watanabe et al. |
| 7,963,433 B2 | 6/2011 | Whitman et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,038,686 B2 | 10/2011 | Huitema et al. |
| 8,048,088 B2 | 11/2011 | Green et al. |

(56) References Cited

U.S. PATENT DOCUMENTS

| | | |
|---|---|---|
| 8,056,565 B2 | 11/2011 | Zergiebel |
| 8,062,310 B2 | 11/2011 | Shibata et al. |
| 8,066,720 B2 | 11/2011 | Knodel et al. |
| 8,066,721 B2 | 11/2011 | Kortenbach et al. |
| 8,066,722 B2 | 11/2011 | Miyagi et al. |
| 8,070,760 B2 | 12/2011 | Fujita |
| 8,075,571 B2 | 12/2011 | Vitali et al. |
| 8,080,021 B2 | 12/2011 | Griego |
| 8,083,668 B2 | 12/2011 | Durgin et al. |
| 8,088,061 B2 | 1/2012 | Wells et al. |
| 8,091,755 B2 | 1/2012 | Kayan et al. |
| 8,100,926 B1 | 1/2012 | Filshie et al. |
| 8,128,643 B2 | 3/2012 | Aranyi et al. |
| 8,133,240 B2 | 3/2012 | Damarati |
| 8,142,451 B2 | 3/2012 | Boulnois et al. |
| 8,157,145 B2 | 4/2012 | Shelton, IV et al. |
| 8,157,149 B2 | 4/2012 | Olson et al. |
| 8,157,151 B2 | 4/2012 | Ingmanson et al. |
| 8,172,859 B2 | 5/2012 | Matsuno et al. |
| 8,172,870 B2 | 5/2012 | Shipp |
| 8,187,290 B2 | 5/2012 | Buckman et al. |
| 8,211,120 B2 | 7/2012 | Itoh |
| 8,211,124 B2 | 7/2012 | Ainsworth et al. |
| 8,216,255 B2 | 7/2012 | Smith et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,678 B2 | 9/2012 | Matsuoka et al. |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,272,554 B2 | 9/2012 | Whitman et al. |
| 8,282,655 B2 | 10/2012 | Whitfield et al. |
| 8,308,743 B2 | 11/2012 | Matsuno et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,366,709 B2 | 2/2013 | Schechter et al. |
| 8,366,726 B2 | 2/2013 | Dennis |
| 8,371,491 B2 | 2/2013 | Huitema et al. |
| 8,372,095 B2 | 2/2013 | Viola |
| 8,382,773 B2 | 2/2013 | Whitfield et al. |
| 8,398,655 B2 | 3/2013 | Cheng et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,408,442 B2 | 4/2013 | Racenet et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,460 B2 | 6/2013 | Yodfat et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,518,055 B1 | 8/2013 | Cardinale et al. |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,556,920 B2 | 10/2013 | Huitema et al. |
| 8,568,430 B2 | 10/2013 | Shipp |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,652,151 B2 | 2/2014 | Lehman et al. |
| 8,652,152 B2 | 2/2014 | Aranyi et al. |
| 8,663,247 B2 | 3/2014 | Menn et al. |
| 8,685,048 B2 | 4/2014 | Adams et al. |
| 8,690,899 B2 | 4/2014 | Kogiso et al. |
| 8,708,213 B2 | 4/2014 | Shelton, IV et al. |
| 8,709,027 B2 | 4/2014 | Adams et al. |
| 8,715,299 B2 | 5/2014 | Menn et al. |
| 8,720,766 B2 | 5/2014 | Hess et al. |
| 8,734,469 B2 | 5/2014 | Pribanic et al. |
| 8,747,423 B2 | 6/2014 | Whitfield et al. |
| 8,753,356 B2 | 6/2014 | Vitali et al. |
| 8,814,884 B2 | 8/2014 | Whitfield et al. |
| 8,821,516 B2 | 9/2014 | Huitema |
| 8,839,954 B2 | 9/2014 | Disch |
| 8,845,659 B2 | 9/2014 | Whitfield et al. |
| 8,894,665 B2 | 11/2014 | Sorrentino et al. |
| 8,894,666 B2 | 11/2014 | Schulz et al. |
| 8,900,253 B2 | 12/2014 | Aranyi et al. |
| 8,915,930 B2 | 12/2014 | Huitema et al. |
| 8,920,438 B2 | 12/2014 | Aranyi et al. |
| 8,939,974 B2 | 1/2015 | Boudreaux et al. |
| 8,950,646 B2 | 2/2015 | Viola |
| 8,961,542 B2 | 2/2015 | Whitfield et al. |
| 8,968,337 B2 | 3/2015 | Whitfield et al. |
| 8,968,342 B2 | 3/2015 | Wingardner, III et al. |
| 8,973,804 B2 | 3/2015 | Hess |
| 9,011,464 B2 | 4/2015 | Zammataro |
| 9,011,465 B2 | 4/2015 | Whitfield et al. |
| 9,089,334 B2 | 7/2015 | Sorrentino et al. |
| 9,113,892 B2 * | 8/2015 | Malkowski ........ A61B 17/1285 |
| 9,113,893 B2 | 8/2015 | Sorrentino et al. |
| 9,119,629 B2 | 9/2015 | Cardinale et al. |
| 9,186,136 B2 | 11/2015 | Malkowski et al. |
| 9,186,153 B2 | 11/2015 | Zammataro |
| 9,208,429 B2 | 12/2015 | Thornton et al. |
| 9,220,507 B1 | 12/2015 | Patel et al. |
| 9,282,961 B2 | 3/2016 | Whitman et al. |
| 9,282,972 B1 | 3/2016 | Patel et al. |
| 9,326,776 B2 | 5/2016 | Gadberry et al. |
| 9,358,011 B2 | 6/2016 | Sorrentino et al. |
| 9,358,015 B2 | 6/2016 | Sorrentino et al. |
| 9,364,216 B2 | 6/2016 | Rockrohr et al. |
| 9,364,239 B2 | 6/2016 | Malkowski |
| 9,364,240 B2 | 6/2016 | Whitfield et al. |
| 9,370,400 B2 | 6/2016 | Parihar |
| 9,393,024 B2 | 7/2016 | Whitfield et al. |
| 9,398,917 B2 | 7/2016 | Whitfield et al. |
| 9,408,610 B2 | 8/2016 | Hartoumbekis |
| 9,414,844 B2 | 8/2016 | Zergiebel et al. |
| 9,433,411 B2 | 9/2016 | Racenet et al. |
| 9,439,654 B2 | 9/2016 | Sorrentino et al. |
| 9,445,810 B2 | 9/2016 | Cappola |
| 9,480,477 B2 | 11/2016 | Aranyi et al. |
| 9,498,227 B2 | 11/2016 | Zergiebel et al. |
| 9,526,501 B2 | 12/2016 | Malkowski |
| 9,526,565 B2 | 12/2016 | Strobl |
| 9,532,787 B2 | 1/2017 | Zammataro |
| 9,545,254 B2 | 1/2017 | Sorrentino et al. |
| 9,549,741 B2 | 1/2017 | Zergiebel |
| 9,642,627 B2 | 5/2017 | Zammataro |
| 9,687,247 B2 | 6/2017 | Aranyi et al. |
| 9,717,504 B2 | 8/2017 | Huitema |
| 9,717,505 B2 | 8/2017 | Whitfield et al. |
| 9,737,310 B2 | 8/2017 | Whitfield et al. |
| 9,750,500 B2 | 9/2017 | Malkowski |
| 9,763,668 B2 | 9/2017 | Whitfield et al. |
| 9,775,623 B2 | 10/2017 | Zammataro et al. |
| 9,775,624 B2 | 10/2017 | Rockrohr et al. |
| 9,782,181 B2 | 10/2017 | Vitali et al. |
| 9,848,886 B2 * | 12/2017 | Malkowski ........ A61B 17/1285 |
| 9,855,043 B2 | 1/2018 | Malkowski |
| 9,931,124 B2 | 4/2018 | Gokharu |
| 9,968,361 B2 | 5/2018 | Aranyi et al. |
| 9,968,362 B2 | 5/2018 | Malkowski et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |

(56) References Cited

U.S. PATENT DOCUMENTS

| | | |
|---|---|---|
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0040226 A1 | 4/2002 | Laufer et al. |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0208231 A1 | 11/2003 | Williamson et al. |
| 2003/0220657 A1 | 11/2003 | Adams |
| 2003/0225423 A1 | 12/2003 | Huitema |
| 2003/0229360 A1 | 12/2003 | Gayton |
| 2003/0233105 A1 | 12/2003 | Gayton |
| 2004/0010272 A1 | 1/2004 | Manetakis et al. |
| 2004/0044352 A1 | 3/2004 | Fowler et al. |
| 2004/0097970 A1 | 5/2004 | Hughett |
| 2004/0097971 A1 | 5/2004 | Hughett |
| 2004/0097972 A1 | 5/2004 | Shipp et al. |
| 2004/0106936 A1 | 6/2004 | Shipp et al. |
| 2004/0133215 A1 | 7/2004 | Baxter |
| 2004/0138681 A1 | 7/2004 | Pier |
| 2004/0153100 A1 | 8/2004 | Ahlberg et al. |
| 2004/0158266 A1 | 8/2004 | Damarati |
| 2004/0162567 A9 | 8/2004 | Adams |
| 2004/0167545 A1 | 8/2004 | Sadler et al. |
| 2004/0176776 A1 | 9/2004 | Zubok et al. |
| 2004/0176783 A1 | 9/2004 | Edoga et al. |
| 2004/0176784 A1 | 9/2004 | Okada |
| 2004/0193213 A1 | 9/2004 | Aranyi et al. |
| 2004/0232197 A1 | 11/2004 | Shelton et al. |
| 2005/0080440 A1 | 4/2005 | Durgin et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter et al. |
| 2005/0177176 A1 | 8/2005 | Gerbi et al. |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079913 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0135992 A1 | 6/2006 | Bettuchi et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker |
| 2006/0212050 A1 | 9/2006 | D'Agostino et al. |
| 2006/0217749 A1 | 9/2006 | Wilson et al. |
| 2006/0224165 A1 | 10/2006 | Surti et al. |
| 2006/0224170 A1 | 10/2006 | Duff |
| 2006/0235437 A1 | 10/2006 | Vitali |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |

(56) References Cited

U.S. PATENT DOCUMENTS

| | | |
|---|---|---|
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0066981 A1 | 3/2007 | Meagher |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0173866 A1 | 7/2007 | Sorrentino et al. |
| 2007/0175949 A1 | 8/2007 | Shelton et al. |
| 2007/0185504 A1 | 8/2007 | Manetakis et al. |
| 2007/0191868 A1 | 8/2007 | Theroux et al. |
| 2007/0203509 A1 | 8/2007 | Bettuchi |
| 2007/0203510 A1 | 8/2007 | Bettuchi |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0083813 A1 | 4/2008 | Zemlok et al. |
| 2008/0103510 A1 | 5/2008 | Taylor et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0167671 A1 | 7/2008 | Giordano et al. |
| 2008/0228199 A1 | 9/2008 | Cropper et al. |
| 2008/0243145 A1 | 10/2008 | Whitfield et al. |
| 2008/0255413 A1 | 10/2008 | Zemlok et al. |
| 2008/0255589 A1 | 10/2008 | Blakeney et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312670 A1 | 12/2008 | Lutze et al. |
| 2008/0319456 A1 | 12/2008 | Hart |
| 2009/0076533 A1 | 3/2009 | Kayan et al. |
| 2009/0088777 A1 | 4/2009 | Miyagi et al. |
| 2009/0088783 A1 | 4/2009 | Kennedy et al. |
| 2009/0171380 A1 | 7/2009 | Whiting |
| 2009/0204115 A1 | 8/2009 | Dees, Jr. et al. |
| 2009/0209946 A1 | 8/2009 | Swayze et al. |
| 2009/0222003 A1 | 9/2009 | Otley |
| 2009/0228023 A1 | 9/2009 | Cui |
| 2009/0228024 A1 | 9/2009 | Whitfield et al. |
| 2009/0261142 A1 | 10/2009 | Milliman et al. |
| 2009/0264904 A1 | 10/2009 | Aldrich et al. |
| 2009/0299382 A1* | 12/2009 | Zergiebel ............ A61B 17/1285 606/142 |
| 2009/0312775 A1 | 12/2009 | Gilkey et al. |
| 2009/0326558 A1 | 12/2009 | Cui et al. |
| 2010/0049216 A1 | 2/2010 | Zergiebel |
| 2010/0057105 A1 | 3/2010 | Sorrentino et al. |
| 2010/0057107 A1 | 3/2010 | Sorrentino et al. |
| 2010/0069935 A1 | 3/2010 | Crainich |
| 2010/0089970 A1 | 4/2010 | Smith et al. |
| 2010/0274262 A1 | 10/2010 | Schulz et al. |
| 2010/0274264 A1 | 10/2010 | Schulz et al. |
| 2010/0318103 A1 | 12/2010 | Cheng et al. |
| 2010/0331862 A1 | 12/2010 | Monassevitch et al. |
| 2011/0054498 A1 | 3/2011 | Monassevitch et al. |
| 2011/0082474 A1 | 4/2011 | Bindra et al. |
| 2011/0087220 A1 | 4/2011 | Felder et al. |
| 2011/0087241 A1 | 4/2011 | Nguyen |
| 2011/0087243 A1 | 4/2011 | Nguyen et al. |
| 2011/0087268 A1 | 4/2011 | Livneh |
| 2011/0112552 A1 | 5/2011 | Lehman et al. |
| 2011/0137323 A1 | 6/2011 | Malkowski et al. |
| 2011/0137324 A1 | 6/2011 | Boudreaux et al. |
| 2011/0144662 A1 | 6/2011 | McLawhorn et al. |
| 2011/0144665 A1 | 6/2011 | Malkowski |
| 2011/0190791 A1 | 8/2011 | Jacobs et al. |
| 2011/0208211 A1 | 8/2011 | Whitfield et al. |
| 2011/0208212 A1 | 8/2011 | Zergiebel et al. |
| 2011/0218553 A1 | 9/2011 | Huitema et al. |
| 2011/0218554 A1 | 9/2011 | Cheng et al. |
| 2011/0218555 A1 | 9/2011 | Huitema |
| 2011/0218556 A1 | 9/2011 | Nguyen et al. |
| 2011/0224696 A1 | 9/2011 | Huitema et al. |
| 2011/0224700 A1 | 9/2011 | Schmidt et al. |
| 2011/0224701 A1 | 9/2011 | Menn |
| 2011/0230900 A1 | 9/2011 | Sarradon |
| 2011/0245847 A1 | 10/2011 | Menn et al. |
| 2011/0245848 A1 | 10/2011 | Rosenberg et al. |
| 2011/0251608 A1 | 10/2011 | Timm et al. |
| 2011/0295290 A1 | 12/2011 | Whitfield |
| 2011/0313437 A1 | 12/2011 | Yeh |
| 2012/0022526 A1 | 1/2012 | Aldridge et al. |
| 2012/0029534 A1 | 2/2012 | Whitfield et al. |
| 2012/0041455 A1 | 2/2012 | Martinez |
| 2012/0046671 A1 | 2/2012 | Matsuoka et al. |
| 2012/0053402 A1 | 3/2012 | Conlon et al. |
| 2012/0059394 A1 | 3/2012 | Brenner et al. |
| 2012/0065647 A1 | 3/2012 | Litscher et al. |
| 2012/0109158 A1 | 5/2012 | Zammataro |
| 2012/0116420 A1 | 5/2012 | Sorrentino et al. |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro et al. |
| 2012/0330326 A1 | 12/2012 | Creston et al. |
| 2013/0041379 A1 | 2/2013 | Bodor et al. |
| 2013/0110135 A1 | 5/2013 | Whitfield et al. |
| 2013/0131697 A1 | 5/2013 | Hartoumbekis |
| 2013/0165951 A1 | 6/2013 | Blake, III |
| 2013/0165952 A1 | 6/2013 | Whitfield et al. |
| 2013/0172909 A1 | 7/2013 | Harris |
| 2013/0172910 A1 | 7/2013 | Malkowski |
| 2013/0172911 A1 | 7/2013 | Rockrohr et al. |
| 2013/0172912 A1 | 7/2013 | Whitfield et al. |
| 2013/0175320 A1 | 7/2013 | Mandakolathur Vasudevan et al. |
| 2013/0226200 A1 | 8/2013 | Kappel et al. |
| 2013/0253540 A1 | 9/2013 | Castro et al. |
| 2013/0253541 A1 | 9/2013 | Zergiebel |
| 2013/0274767 A1 | 10/2013 | Sorrentino et al. |
| 2013/0289583 A1 | 10/2013 | Zergiebel et al. |
| 2013/0296891 A1 | 11/2013 | Hartoumbekis |
| 2013/0296892 A1 | 11/2013 | Sorrentino et al. |
| 2013/0310849 A1 | 11/2013 | Malkowski |

(56) References Cited

U.S. PATENT DOCUMENTS

| | | |
|---|---|---|
| 2013/0325040 A1 | 12/2013 | Zammataro |
| 2013/0325057 A1 | 12/2013 | Larson et al. |
| 2014/0005693 A1 | 1/2014 | Shelton, IV et al. |
| 2014/0039526 A1 | 2/2014 | Malkowski |
| 2014/0052157 A1 | 2/2014 | Whitfield et al. |
| 2014/0058412 A1 | 2/2014 | Aranyi et al. |
| 2014/0074143 A1 | 3/2014 | Fitzgerald et al. |
| 2014/0188159 A1 | 7/2014 | Steege |
| 2014/0194903 A1 | 7/2014 | Malkowski et al. |
| 2014/0207156 A1 | 7/2014 | Malkowski |
| 2014/0263565 A1 | 9/2014 | Lytle, IV et al. |
| 2014/0276970 A1 | 9/2014 | Messerly et al. |
| 2014/0296879 A1 | 10/2014 | Menn et al. |
| 2014/0316441 A1 | 10/2014 | Zergiebel et al. |
| 2014/0330291 A1 | 11/2014 | Whitfield et al. |
| 2014/0371728 A1 | 12/2014 | Vaughn |
| 2015/0005790 A1 | 1/2015 | Whitfield et al. |
| 2015/0032131 A1 | 1/2015 | Sorrentino et al. |
| 2015/0045816 A1 | 2/2015 | Aranyi et al. |
| 2015/0066057 A1 | 3/2015 | Rockrohr et al. |
| 2015/0080916 A1 | 3/2015 | Aranyi et al. |
| 2015/0127022 A1 | 5/2015 | Whitfield et al. |
| 2015/0164511 A1 | 6/2015 | Whitfield et al. |
| 2015/0190138 A1 | 7/2015 | Whitfield et al. |
| 2015/0190139 A1 | 7/2015 | Zammataro |
| 2015/0201953 A1 | 7/2015 | Strobl et al. |
| 2015/0265282 A1 | 9/2015 | Miles et al. |
| 2015/0282808 A1 | 10/2015 | Sorrentino et al. |
| 2015/0313452 A1 | 11/2015 | Hasser et al. |
| 2015/0314451 A1 | 11/2015 | Nixon |
| 2015/0351771 A1 | 12/2015 | Malkowski et al. |
| 2015/0351772 A1 | 12/2015 | Malkowski et al. |
| 2016/0004956 A1 | 1/2016 | Reynolds et al. |
| 2016/0030044 A1 | 2/2016 | Zammataro |
| 2016/0030045 A1 | 2/2016 | Malkowski et al. |
| 2016/0113655 A1 | 4/2016 | Holsten |
| 2016/0151071 A1 | 6/2016 | Tokarz et al. |
| 2016/0192940 A1 | 7/2016 | Gokharu |
| 2016/0213377 A1 | 7/2016 | Shankarsetty |
| 2016/0242789 A1 | 8/2016 | Sorrentino et al. |
| 2016/0256157 A1 | 9/2016 | Rockrohr et al. |
| 2016/0256158 A1 | 9/2016 | Whitfield et al. |
| 2016/0262764 A1 | 9/2016 | Gokharu |
| 2016/0296236 A1 | 10/2016 | Whitfield et al. |
| 2016/0338695 A1 | 11/2016 | Hartoumbekis |
| 2016/0338699 A1 | 11/2016 | Sorrentino et al. |
| 2017/0027581 A1 | 2/2017 | Zergiebel et al. |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0172780 A1 | 6/2017 | Aravalli |
| 2017/0202567 A1 | 7/2017 | Griffiths et al. |
| 2017/0238936 A1 | 8/2017 | Mujawar |
| 2017/0245921 A1 | 8/2017 | Joseph et al. |
| 2017/0252042 A1 | 9/2017 | Kethman et al. |
| 2017/0258472 A1 | 9/2017 | Aranyi et al. |
| 2017/0290587 A1 | 10/2017 | Schober et al. |
| 2017/0325814 A1 | 11/2017 | Malkowski |
| 2017/0340325 A1 | 11/2017 | Baril et al. |
| 2017/0340331 A1 | 11/2017 | Hu et al. |
| 2017/0340332 A1 | 11/2017 | Whitfield et al. |
| 2017/0360449 A1 | 12/2017 | Rockrohr et al. |
| 2018/0008276 A1 | 1/2018 | Bhatnagar et al. |
| 2018/0008277 A1 | 1/2018 | Baril |
| 2018/0021041 A1 | 1/2018 | Zhang et al. |
| 2018/0070952 A1 | 3/2018 | Malkowski et al. |
| 2018/0116671 A1 | 5/2018 | Prior |
| 2018/0116673 A1 | 5/2018 | Baril et al. |
| 2018/0116674 A1 | 5/2018 | Baril |
| 2018/0116675 A1 | 5/2018 | Baril |
| 2018/0116676 A1 | 5/2018 | Williams |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cai et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CA | 1163889 A | 3/1984 |
| CA | 2740831 A1 | 4/2010 |
| CN | 1 939 231 A | 4/2007 |
| CN | 1994236 A | 7/2007 |
| CN | 101401737 A | 4/2009 |
| CN | 101530340 A | 9/2009 |
| CN | 101658437 A | 3/2010 |
| CN | 101664329 A | 3/2010 |
| CN | 101664331 A | 3/2010 |
| CN | 101703414 A | 5/2010 |
| CN | 201683954 U | 12/2010 |
| CN | 103083059 A | 5/2013 |
| CN | 103181809 A | 7/2013 |
| CN | 103181810 A | 7/2013 |
| CN | 103251441 A | 8/2013 |
| CN | 103976771 A | 8/2014 |
| CN | 104487006 A | 4/2015 |
| CN | 104605911 B | 2/2017 |
| DE | 202007003398 U1 | 6/2007 |
| DE | 20 2009 006113 U1 | 7/2009 |
| EP | 0073655 A1 | 3/1983 |
| EP | 0085931 A2 | 8/1983 |
| EP | 0086721 A2 | 8/1983 |
| EP | 0089737 A1 | 9/1983 |
| EP | 0092300 A1 | 10/1983 |
| EP | 0324166 A2 | 7/1989 |
| EP | 0392750 A1 | 10/1990 |
| EP | 0406724 A1 | 1/1991 |
| EP | 0409569 A1 | 1/1991 |
| EP | 0569223 A1 | 11/1993 |
| EP | 0594003 A1 | 4/1994 |
| EP | 0598529 A2 | 5/1994 |

(56) References Cited

FOREIGN PATENT DOCUMENTS

| | | |
|---|---|---|
| EP | 0685204 A1 | 12/1995 |
| EP | 0732078 A2 | 9/1996 |
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1468653 A2 | 10/2004 |
| EP | 1609427 A1 | 12/2005 |
| EP | 1 712 189 A2 | 10/2006 |
| EP | 1712187 A2 | 10/2006 |
| EP | 1712191 A2 | 10/2006 |
| EP | 1757236 A2 | 2/2007 |
| EP | 1813199 A1 | 8/2007 |
| EP | 1813207 A1 | 8/2007 |
| EP | 1894531 A2 | 3/2008 |
| EP | 1908423 A2 | 4/2008 |
| EP | 1913881 A1 | 4/2008 |
| EP | 2000102 A2 | 12/2008 |
| EP | 2140817 A1 | 1/2010 |
| EP | 2229895 A1 | 9/2010 |
| EP | 2 263 570 A1 | 12/2010 |
| EP | 2332471 A1 | 6/2011 |
| EP | 2412318 A2 | 2/2012 |
| EP | 2412319 A2 | 2/2012 |
| EP | 2 752 165 A2 | 7/2014 |
| EP | 3132756 A1 | 2/2017 |
| GB | 1134832 A | 11/1968 |
| GB | 2073022 A | 10/1981 |
| GB | 2 132 899 A | 7/1984 |
| JP | 2003033361 A | 2/2003 |
| JP | 2006154230 A | 6/2006 |
| JP | 2006277221 A | 10/2006 |
| JP | 2008017876 A | 1/2008 |
| JP | 2008515550 A | 5/2008 |
| JP | 2009198991 A | 9/2009 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 01/65997 A2 | 9/2001 |
| WO | 2001-66001 A2 | 9/2001 |
| WO | 2001-67965 A1 | 9/2001 |
| WO | 2003-086207 A1 | 10/2003 |
| WO | 2003-092473 A2 | 11/2003 |
| WO | 2004032762 A1 | 4/2004 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

Chinese First Office Action corresponding to Int'l Appln. No. CN 201410008877.5 dated Apr. 6, 2017.
Chinese Office Action corresponding to counterpart Int'l Appln No. CN 201210212642.9 dated Jun. 3, 2015.
European Office Action corresponding to counterpart Int'l Appln No. EP 04 719 757.9 dated Jun. 12, 2015.
European Office Action corresponding to counterpart Int'l Appln No. EP 13 166 382.5 dated Jun. 19, 2015.
Japanese Office Action corresponding to counterpart Int'l Application No. JP 2010-226908 dated Jun. 26, 2015.
Extended European Search Report corresponding to counterpart Int'l Application No. EP 15 15 5024.1 dated Jul. 17, 2015.
Extended European Search Report corresponding to counterpart Int'l Application No. EP 14 19 2026.4 dated Jul. 17, 2015.
Japanese Office Action corresponding to counterpart Int'l Application No. JP 2011-160126 dated Aug. 10, 2015.
Extended European Search Report corresponding to counterpart Int'l Application No. EP 11 25 0675.3 dated Oct. 1, 2015.
Extended European Search Report corresponding to counterpart Int'l Application No. EP 11 25 0674.6 dated Oct. 1, 2015.
Extended European Search Report corresponding to counterpart Int'l Application No. EP 12 19 3447.5 dated Oct. 19, 2015.
Canadian Office Action corresponding to counterpart Int'l Application No. CA 2,675,875 dated Oct. 26, 2015.
Japanese Office Action corresponding to counterpart Int'l Application No. JP 2015-005629 dated Oct. 28, 2015.
Japanese Office Action corresponding to counterpart Int'l Application No. JP 2014-245081 dated Oct. 28, 2015.
Canadian Office Action corresponding to counterpart Int'l Application No. CA 2,675,921 dated Oct. 30, 2015.
Chinese Office Action corresponding to counterpart Int'l Application No. CN 201210555570.8 dated Nov. 2, 2015.
Canadian Office Action corresponding to counterpart Int'l Application No. CA 2,676,309 dated Nov. 3, 2015.
Canadian Office Action corresponding to counterpart Int'l Application No. CA 2,676,211 dated Nov. 24, 2015.
Canadian Office Action corresponding to counterpart Int'l Application No. CA 2,676,547 dated Nov. 25, 2015.
Extended European Search Report corresponding to counterpart Int'l Application No. EP 15 17 3809.3 dated Nov. 25, 2015.
Chinese Office Action corresponding to counterpart Int'l Application No. CN 201210586814.9 dated Dec. 2, 2015.
Extended European Search Report corresponding to counterpart Int'l Application No. EP 12 17 2940.4 dated Dec. 14, 2015.
Chinese First Office Action corresponding to counterpart Int'l Appln. No. CN 201210586826.1 dated Dec. 30, 2015.
Extended European Search Report corresponding to counterpart Int'l Appln. No. EP 15 19 1313.4 dated Feb. 1, 2016.
Extended European Search Report corresponding to counterpart Int'l Appln. No. EP 15 18 5362.9 dated Feb. 12, 2016.
European Search Report corresponding to counterpart Int'l Appln. No. EP 12 19 7813.4 dated Mar. 7, 2016.
Office Action corresponding to counterpart Int'l Appln. No. CA 2,676,465 dated Mar. 8, 2016.
Office Action corresponding to counterpart Int'l Appln. No. JP 2014-245081 dated Mar. 18, 2016.
Office Action corresponding to counterpart Int'l Appln. No. JP 2015-005629 dated Mar. 18, 2016.
Extended European Search Report corresponding to counterpart Int'l Appln. No. EP 15 19 3549.1 dated Mar. 22, 2016.
International Search Report and Written Opinion corresponding to counterpart Int'l Appln. No. PCT/CN2015/082199 dated Mar. 31, 2016.
Extended European Search Report corresponding to counterpart Int'l Appln. No. EP 15 19 7251.0 dated Apr. 8, 2016.
Extended European Search Report corresponding to counterpart Int'l Appln. No. EP 16 15 0739.7 dated May 17, 2016.
Canadian Office Action corresponding to counterpart Int'l Appln. No. CA 2,716,672 dated May 31, 2016.
Canadian Office Action corresponding to counterpart Int'l Appln. No. CA 2,717,448 dated May 31, 2016.
Canadian Office Action corresponding to counterpart Int'l Appln. No. CA 2,721,951 dated Jun. 1, 2016.
Partial European Search Report corresponding to counterpart Int'l Appln. No. EP 16 15 0287.7 dated Jun. 16, 2016.
Chinese Second Office Action corresponding to counterpart Int'l Appln. No. CN 201210555570.8 dated Jun. 20, 2016.
International Search Report & Written Opinion corresponding to Int'l Appln. No. PCT/CN2015/091603 dated Jul. 8, 2016.
European Office Action corresponding to EP 12 152 989.5 dated May 4, 2015.
Australian Office Action corresponding to AU 2009212759 dated May 7, 2015.

(56) References Cited

OTHER PUBLICATIONS

Extended European Search Report corresponding to counterpart International Application No. EP 14 15 0321.9, dated Sep. 23, 2015; (8 pp.).
The extended European Search Report corresponding to European Application No. EP 07 25 3905.9, completed Jan. 29, 2008; dated Feb. 7, 2008; (7 Pages).
International Search Report corresponding to International Application No. PCT-US08-58185, completed Sep. 4, 2008; dated Sep. 9, 2008; (2 Pages).
The International Search Report corresponding to International Application No. PCT-US08-59859, completed Sep. 14, 2008; dated Sep. 18, 2008; (2 Pages).
The extended European Search Report corresponding to European Application No. EP 07 25 3807.7, completed Nov. 1, 2008; dated Nov. 26, 2008; (11 Pages).
The extended European Search Report corresponding to European Application No. EP 09 25 2049.3, completed Dec. 11, 2009; dated Jan. 12, 2010; (3 Pages).
The extended European Search Report corresponding to European Application No. EP 09 25 2050.1, completed Dec. 23, 2009; dated Jan. 21, 2010; (3 Pages).
The extended European Search Report corresponding to European Application No. EP 09 25 2051.9, completed Dec. 21, 2009; dated Jan. 28, 2010; (3 Pages).
European Office Action corresponding to Int'l Appln. No. EP 08 73 2820.9 dated Nov. 3, 2016.
Extended European Search Report corresponding to Int'l Appln. No. EP 16 18 5465.8 dated Dec. 21, 2016.
Chinese First Office Action corresponding to Int'l Appln. No. CN 201510419902.3 dated Jan. 4, 2017.
The extended European Search Report corresponding to European Application No. EP 09 25 2052.7, completed Nov. 16, 2009; dated Nov. 24, 2009; (3 Pages).
The extended European Search Report corresponding to European Application No. EP 09 25 2053.5, completed Nov. 24, 2009; dated Dec. 1, 2009; (3 Pages).
The extended European Search Report corresponding to European Application No. EP 09 25 2054.3, completed Jan. 7, 2010; dated Jan. 22, 2010; (3 Pages).
The extended European Search Report corresponding to European Application No. EP 09 25 2056.8, completed Jan. 3, 2010; dated Feb. 5, 2010; (3 Pages).
The extended European Search Report corresponding to European Application No. EP 10 25 0497.4, completed May 1, 2010; dated May 12, 2010; (6 Pages).
The extended European Search Report corresponding to European Application No. EP 10 25 2079.8, completed Mar. 3, 2011; dated Mar. 17, 2011; (3 Pages).
The European Search Report corresponding to European Application No. EP 05 81 0218.7, completed Apr. 18, 2011; dated May 20, 2011; (3 pages).
The European Search Report corresponding to European Application No. EP 05 80 7612.6, completed May 2, 2011; dated May 20, 2011; (3 pages).
The extended European Search Report corresponding to European Application No. EP 10 25 1737.2, completed May 9, 2011; dated May 20, 2011; (4 pages).
The extended European Search Report corresponding to European Application No. EP 11 25 0214.1, completed May 25, 2011; dated Jun. 1, 2011; (3 Pages).
The extended European Search Report corresponding to European Application No. EP 11 00 2681.2, completed May 31, 2011; dated Jun. 10, 2011; (3 Pages).
The European Search Report corresponding to European Application No. EP 05 80 2686.5, completed Jan. 9, 2012; dated Jan. 18, 2012; (3 Pages).
The extended European Search Report corresponding to European Application No. EP 12 15 1313.9, completed Mar. 20, 2012 and dated Apr. 12, 2012; (5 Pages).

The extended European Search Report corresponding to European Application No. EP 12 16 1291.5, completed Apr. 24, 2012 and dated May 4, 2012; (5 Pages).
The extended European Search Report corresponding to European Application No. EP 12 16 5891.8, completed Jun. 12, 2012 and dated Jun. 20, 2012; (6 Pages).
The extended European Search Report corresponding to European Application No. EP 12 16 2288.0, completed Jun. 1, 2012 and dated Jul. 7, 2012; (6 Pages).
The extended European Search Report corresponding to European Application No. EP 12 16 4955.2, completed Aug. 23, 2012 and dated Sep. 4, 2012; (5 Pages).
The extended European Search Report corresponding to European Application No. EP 11 25 0754.6, completed Oct. 22, 2012 and dated Oct. 31, 2012; (6 Pages).
The extended European Search Report corresponding to European Application No. EP 12 18 6401.1, completed Nov. 22, 2012 and dated Nov. 30, 2012; (7 Pages).
The extended European Search Report corresponding to European Application No. EP 12 18 6448.2, completed Nov. 28, 2012 and dated Dec. 10, 2012; (6 Pages).
The extended European Search Report corresponding to European Application No. EP 12 19 1706.6, completed Dec. 19, 2012 and dated Jan. 8, 2013; (6 Pages).
The Extended European Search Report corresponding to EP 12 19 8745.7, completed Mar. 19, 2013 and dated Apr. 11, 2013; (8 Pages).
The Extended European Search Report corresponding to EP 12 15 2989.5, completed Apr. 9, 2013 and dated Apr. 18, 2013; (9 Pages).
The Extended European Search Report corresponding to EP 08 73 2820.9, completed Jul. 2, 2013 and dated Jul. 9, 2013; (10 Pages).
The Extended European Search Report corresponding to EP 13 17 2008.8, completed Aug. 14, 2013 and dated Aug. 28, 2013; (8 Pages).
The Extended European Search Report corresponding to EP 13 16 6382.5, completed Nov. 19, 2013 and dated Nov. 28, 2013; (8 Pages).
The Extended European Search Report corresponding to EP 11 25 0194.5, completed Nov. 25, 2013 and dated Dec. 3, 2013; (8 Pages).
The Extended European Search Report corresponding to EP 10 25 1798.4, completed Dec. 12, 2013 and dated Jan. 2, 2014; (9 Pages).
"Salute II Disposable Fixation Device", Technique Guide—Laparoscopic and Open Inguinal and Ventral Hernia Repair; Davol, A Bard Company, 2006; (7 Pages) .
The Extended European Search Report corresponding to EP 10 25 2112.7, completed Jul. 29, 2014 and dated Aug. 5, 2014; (8 pp).
The Extended European Search Report corresponding to EP 14 15 1673.2, completed Apr. 25, 2014 and dated May 8, 2014; (8 pp).
Japanese Office Action corresponding to JP 2011-160130 dated Dec. 1, 2014.
Chinese Office Action corresponding to CN 201210015011.8 dated Jan. 4, 2015.
Japanese Office Action corresponding to JP 2011-160126 dated Jan. 9, 2015.
Japanese Office Action corresponding to JP 2011-184521 dated Jan. 15, 2015.
Extended European Search Report corresponding to 14 18 2236.1 dated Jan. 20, 2015.
Chinese Office Action corresponding to CN 201110201736.1 dated Feb. 9, 2015.
Extended European Search Report corresponding to EP 14 16 1540.1 dated Feb. 27, 2015.
Australian Office Action corresponding to AU 2010226985 dated Mar. 31, 2015.
Australian Office Action corresponding to AU 2013211526 dated Apr. 6, 2015.
Australian Office Action corresponding to AU 2011211463 dated Apr. 13, 2015.
Australian Office Action corresponding to AU 2013254887 dated Apr. 14, 2015.
Japanese Office Action corresponding to JP 2013-225272 dated May 1, 2015.

(56) References Cited

OTHER PUBLICATIONS

Chinese Second Office Action corresponding to Int'l Appln. No. CN 201210586814.9 dated Jul. 18, 2016.
Chinese First Office Action corresponding to Int'l Appln. No. CN 201510093591.6 dated Jul. 25, 2016.
International Search Report & Written Opinion corresponding to Int'l Appln. No. PCT/CN2015/094172 dated Aug. 4, 2016.
Canadian Office Action corresponding to Int'l Appln. No. CA 2,728,538 dated Sep. 6, 2016.
Chinese Second Office Action corresponding to Int'l Appln. No. CN 201210586826.1 dated Sep. 14, 2016.
Extended European Search Report corresponding to Int'l Appln. No. EP 16 15 0287.7 dated Oct. 4, 2016.
Chinese First Office Action corresponding to Int'l Appln. No. CN 201510205737.1 dated Nov. 1, 2016.
Extended European Search Report corresponding to Patent Application EP 18154617.7 dated Jun. 25, 2018.
Extended European Search Report corresponding to Patent Application EP 18155158.1 dated Jun. 28, 2018.
European Search Report corresponding to Patent Application EP 15877428.1 dated Jul. 2, 2018.
European Search Report corresponding to Patent Application EP 18157789.1 dated Jul. 5, 2018.
Office Action corresponding to Patent Application CA 2,972,444 dated Aug. 9, 2018.
European Search Report corresponding to Patent Application EP 18156458.4 dated Sep. 3, 2018.
European Search Report corresponding to Patent Application EP 18171682.0 dated Sep. 18, 2018.
European Search Report corresponding to Patent Application EP 15878354.8 dated Sep. 19, 2018.
European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.
International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
European Office Action corresponding to European Appln. No. EP 16 15 9324.9 dated Aug. 7, 2017.
Chinese First Office Action corresponding to Chinese Appln. No. CN 2014104295806 dated Aug. 31, 2017.
Extended European Search Report corresponding to European Appln. No. EP 17 17 3508.7 dated Sep. 29, 2017.
Chinese Second Office Action corresponding to Chinese Appln. No. CN 201410076318.8 dated Oct. 10, 2017.
Extended European Search Report corresponding to European Appln. No. EP 17 18 0570.8 dated Dec. 6, 2017.
Chinese Office Acttion for application No. 201610694951.2 dated Apr. 23, 2020 with English translation.

\* cited by examiner

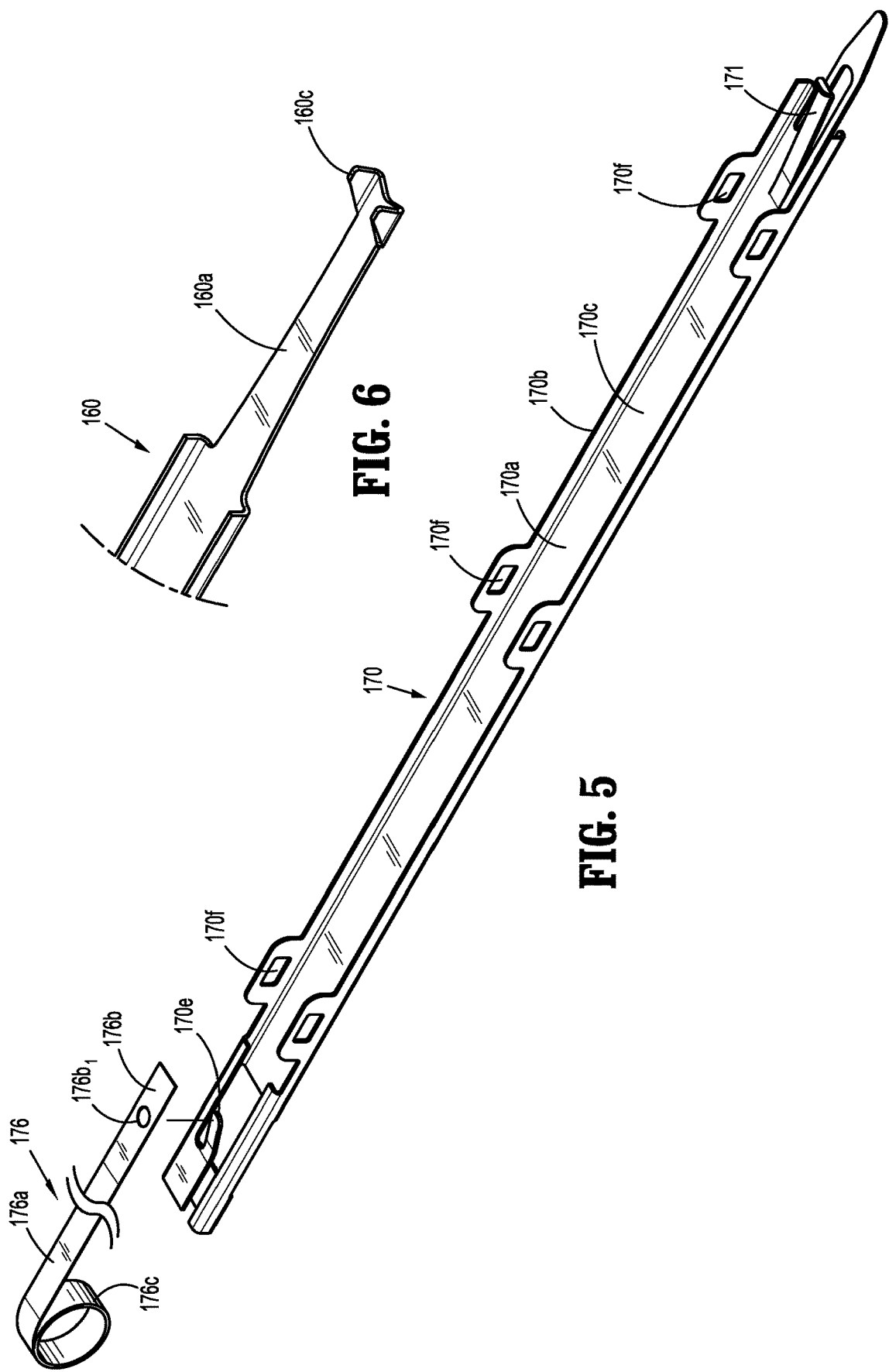

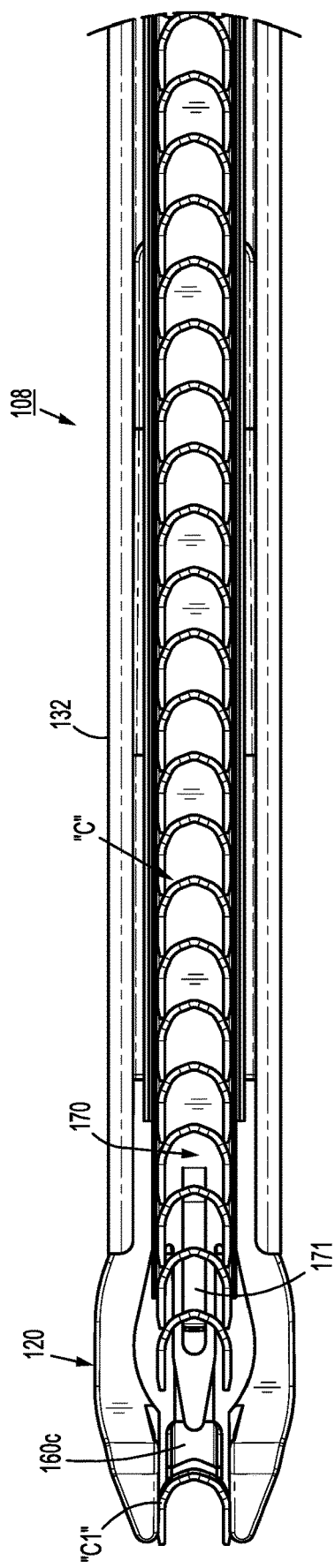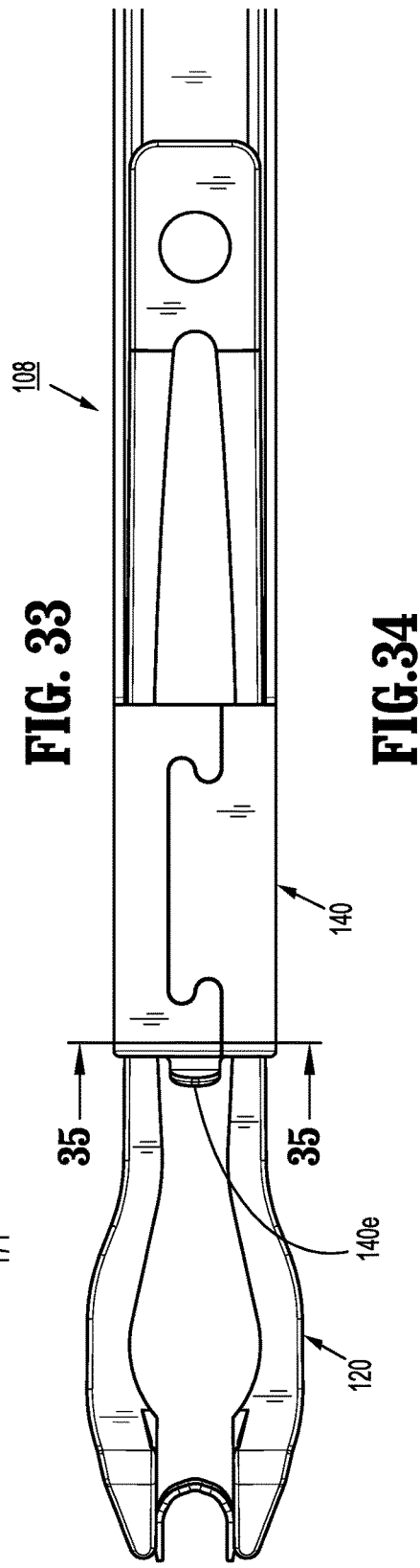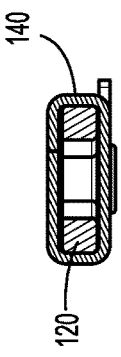
FIG. 33
FIG. 34
FIG. 35

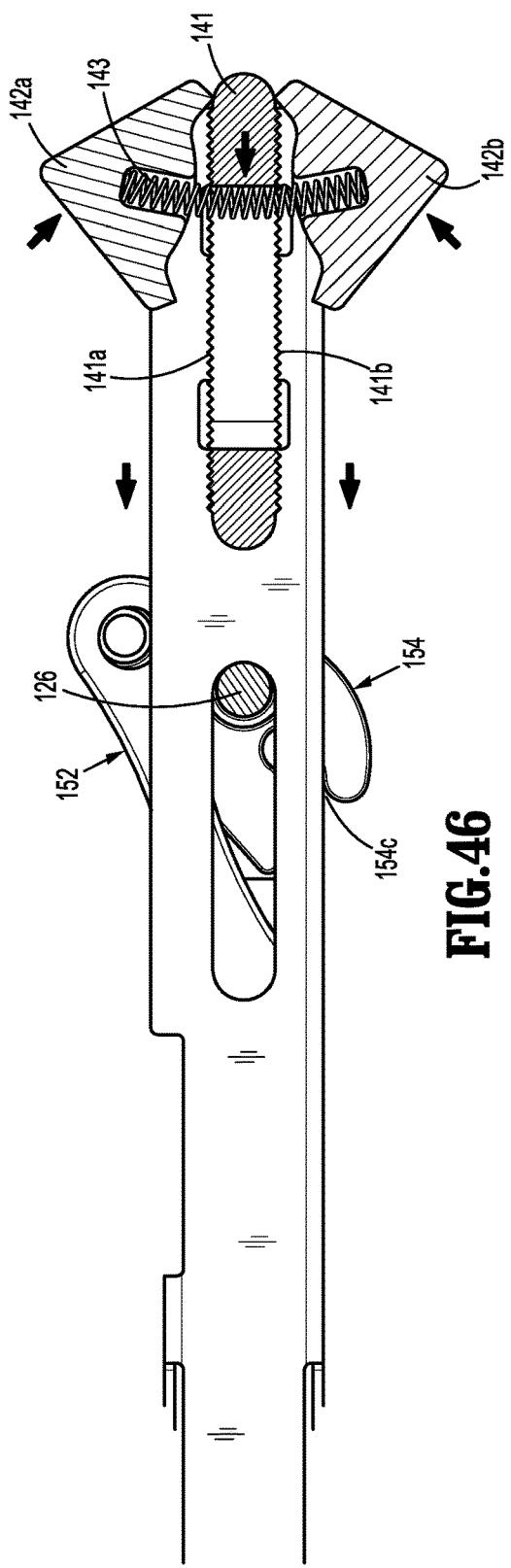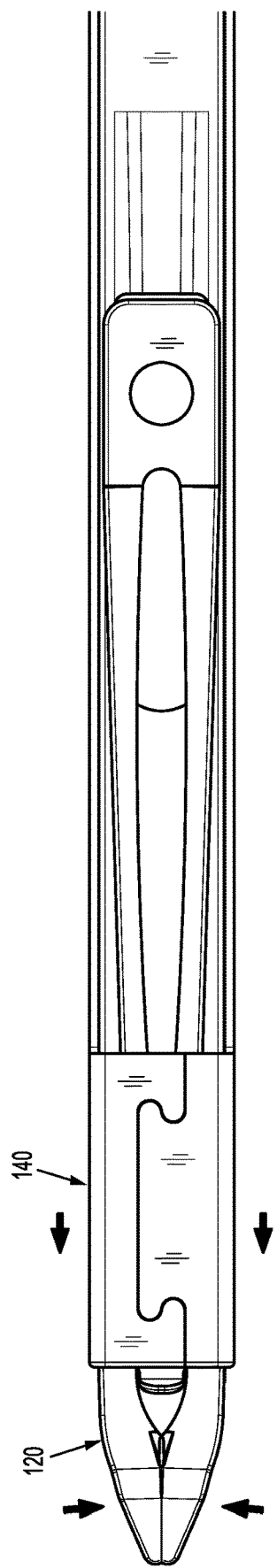
FIG. 46
FIG. 47

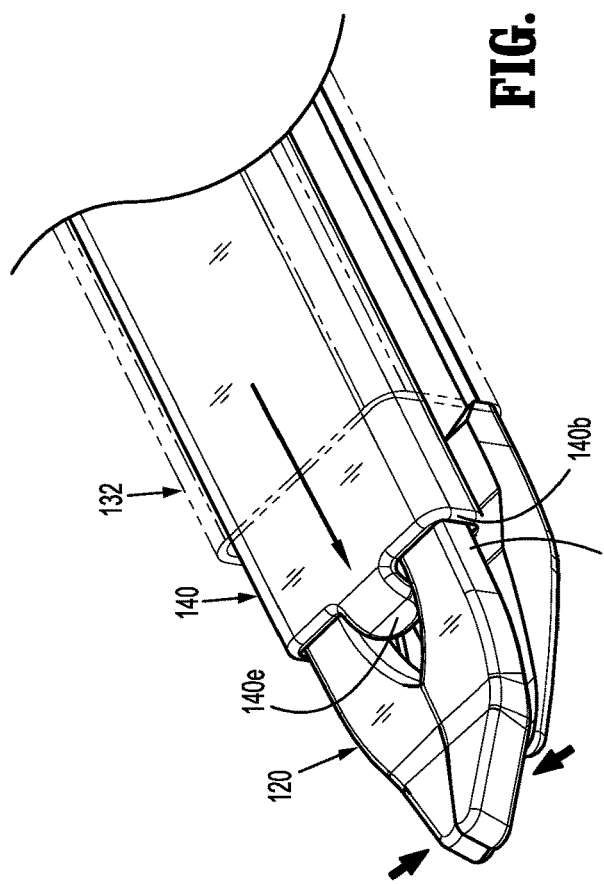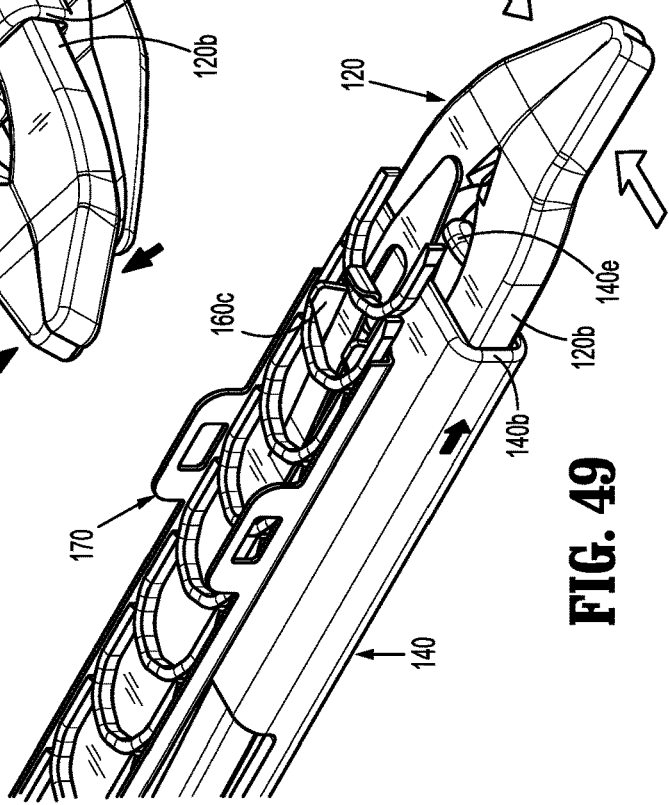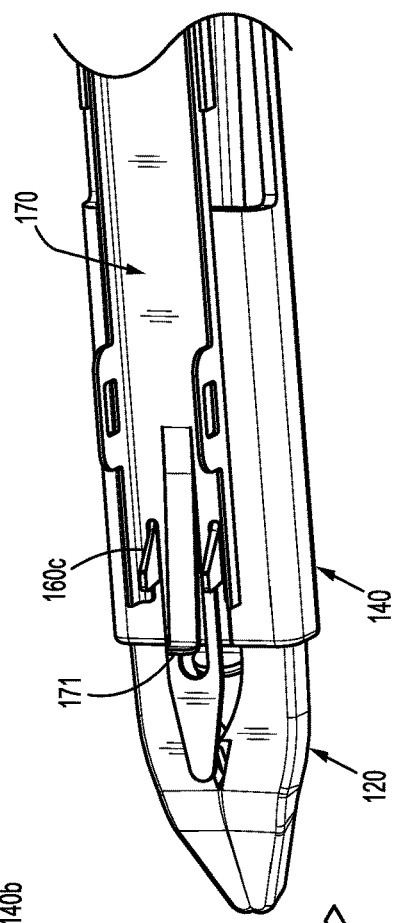
FIG. 48
FIG. 49
FIG. 50

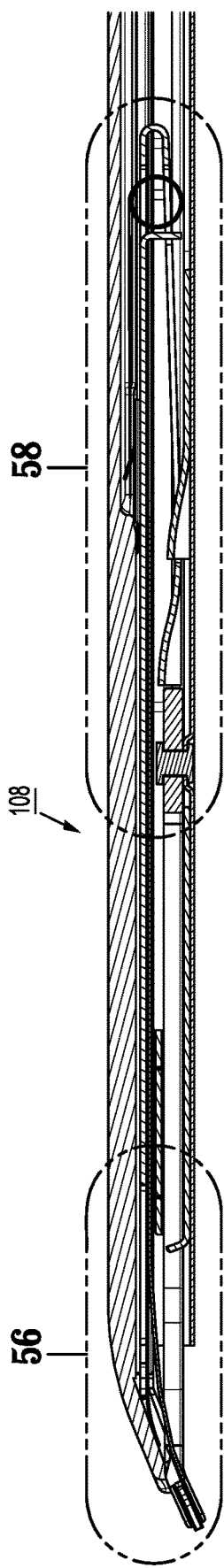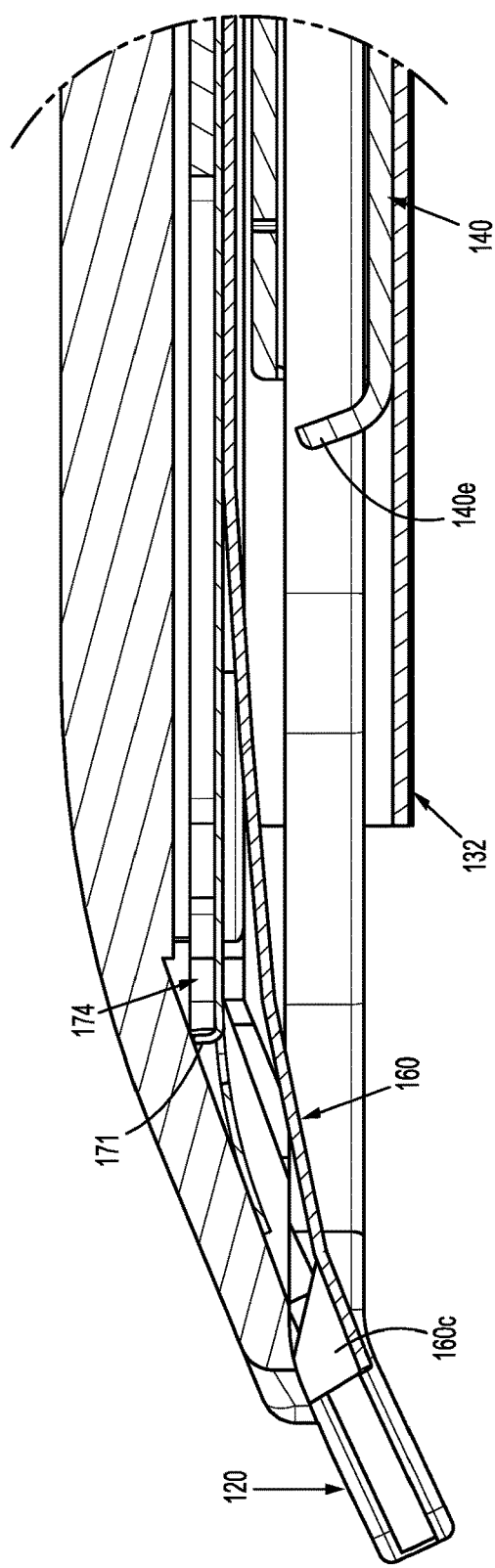
FIG. 55
FIG. 56

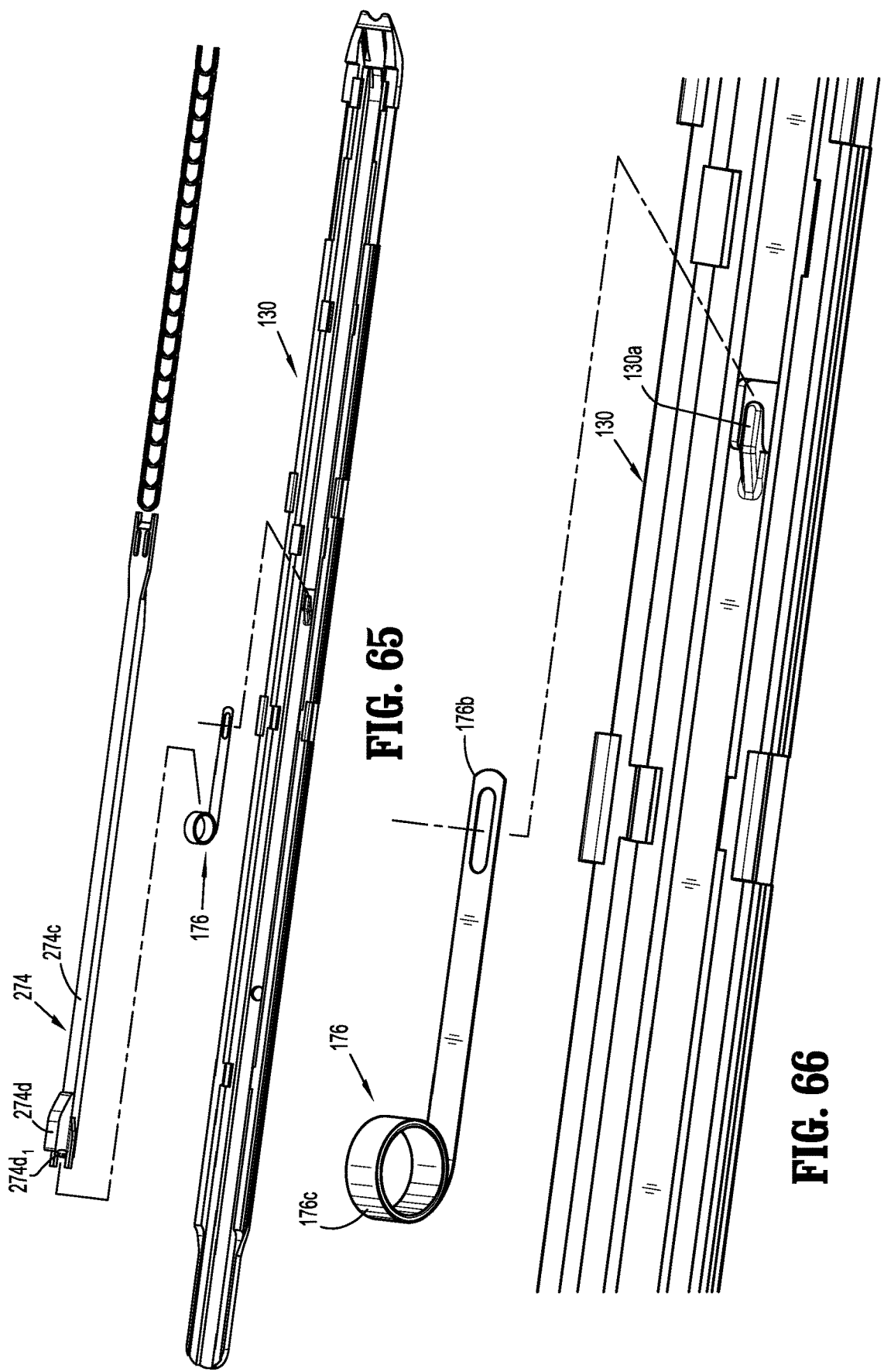

SURGICAL CLIP APPLIER

CROSS REFERENCE TO RELATED APPLICATIONS

The present application is a continuation of U.S. patent application Ser. No. 14/828,588 filed Aug. 18, 2015, which is a continuation which claims the benefit of and priority to U.S. patent application Ser. No. 13/736,109, now U.S. Pat. No. 9,113,892, filed Jan. 8, 2013, the entire content of which is incorporated by reference herein.

TECHNICAL FIELD

The present application relates to surgical instruments, and more particularly, to surgical clip appliers having a plurality of clips for applying the clips to body tissues and vessels during surgical procedures.

BACKGROUND

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank, III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Inevitably, these instruments tend to be relatively complex, including many parts, many of which move and cooperate with one another.

Thus, in light of the increasing cost of healthcare and surgery, a need exists to curb the costs of the devices used during a surgical procedure or the like.

Accordingly, a need exists for an improved clip applier having fewer parts and which is more economical to manufacture.

SUMMARY

The present application relates to surgical clip appliers having a plurality of clips for applying the clips to body tissues and vessels during surgical procedures and their methods of use.

According to an aspect of the present disclosure, a surgical clip applier is provided and includes a housing; at least one handle pivotably connected to the housing; a channel assembly extending distally from the housing; a clip carrier disposed within the channel assembly and defining a channel; a plurality of clips loaded in the channel of the clip carrier; a drive channel translatably supported in the housing and the channel assembly, the drive channel being translated upon actuation of the at least one handle; and a ratchet mechanism disposed within the housing. The ratchet mechanism includes a rack member connected to the drive channel such that axial translation of the drive channel results in axial translation of the rack member, the rack member defining a first set of teeth along a first side thereof and a second set of teeth along a second side thereof; a first pawl and a second pawl each tiltably supported in the housing and disposed on respective opposed sides of the rack member; and a buckling spring interposed between the first pawl and the second pawl and constrained in a slot formed in the rack member, wherein the buckling spring is dimensioned so as to bow in one of a proximal direction and a distal direction.

In use, when the buckling spring is bowed in the proximal direction, the first pawl and the second pawl are engaged with the rack member so as to permit the drive channel to move in a distal direction; and, when the buckling spring is bowed in the distal direction, the first pawl and the second pawl are engaged with the rack member so as to permit the drive channel to move in a proximal direction.

The surgical clip applier may further include a clip follower slidably disposed within the channel of the clip carrier and disposed proximally of the plurality of clips, the clip follower being configured and adapted for selective incremental advancement through the channel of the clip carrier and through the channel assembly, wherein the clip follower is configured and adapted to urge the plurality of clips, in a distal direction relative to the clip carrier, following a loading of a distal-most clip of the plurality of clips into the pair of jaws.

The clip follower may be urged in a distal direction by a biasing member. The biasing member may be a constant force spring. The constant force spring may include a distal end secured against movement in the surgical clip applier, and a proximal end coiled onto itself. The coiled proximal end of the constant force spring may be connected to the clip follower so as to draw the clip follower distally upon a coiling of the coiled proximal end of the constant force spring.

The surgical clip applier may further include a clip pusher bar reciprocally positioned within at least one of the housing and the channel assembly. The pusher bar may have a first end operatively connected to the at least one handle and a second end defining a pusher. The pusher bar may be movable away from the pair of jaws as the at least one handle is actuated in order to move the pusher behind a distal-most clip stored in the channel of the clip carrier. The pusher bar may be configured and adapted to move towards the jaws as the at least one handle is returned to an un-actuated position to move the distal-most clip between the pair of jaws.

The clip follower may include a head configured and dimensioned for engagement by the pusher of the clip pusher bar, when in a retracted position, following a loading of a final clip of the stack of clips into a pair of jaws of the surgical clip applier.

In use, following engagement of the head of the clip follower by the pusher of the clip pusher bar, a distal advancement of the clip pusher bar may advance the clip follower distally such that the head of the clip follower is positioned between the pair of jaws.

In use, when the head of the clip follower is positioned between the pair of jaws, the head of the clip follower may prevent the pair of jaws from closing and thus prevents the at least one handle from actuating completely.

The surgical clip applier may further include a jaw assembly including a pair of jaws extending from an end of the channel assembly, opposite the housing, the jaw assembly adapted to accommodate a clip therein and being operable to effect formation of a clip in response to movement of the at least one handle.

The drive channel may include a first end operatively connected to the at least one handle and a second end configured and dimensioned to surround and selectively engage the pair of jaws to effectuate closure of the pair of jaws. The drive channel may be moved towards the jaw assembly as the at least one handle is moved in a first direction to move the second end of the drive channel against the pair of jaws to close the pair of jaws. The drive channel may be moved away from the jaw assembly as the at least one handle is moved in a second direction, opposite the first direction, to move the second end of the drive channel away from the jaw assembly to allow the pair of jaws to open.

The second end of the drive channel may include a tongue extending between the pair of jaws.

In use, with the drive channel disposed at a proximal-most position, with the buckling spring bowed in the proximal direction, and with the first pawl and the second pawl engaged with the rack member so as to permit the drive channel to move in a distal direction, when the drive channel is advanced to a distal-most position, the proximally bowing buckling spring may be acted on and caused to bow in the distal direction, whereby the drive channel is permitted to move in a proximal direction.

In use, with the drive channel disposed at a distal-most position, with the buckling spring bowed in the distal direction, and with the first pawl and the second pawl engaged with the rack member so as to permit the drive channel to move in a proximal direction, when the drive channel is retracted to the proximal-most position, the distally bowing buckling spring may be acted on and caused to bow in the proximal direction, whereby the drive channel is permitted to move in a distal direction.

The drive channel may include a stop tab projecting therefrom in a direction toward the clip follower, and wherein the clip follower defines a window therein. In use, when the clip follower is in a distal-most position with the head thereof disposed between the pair of jaws, and when the drive channel is in a proximal-most position, the stop tab of the drive channel may be disposed in the window of the clip follower.

The clip follower may include an elongate body having a distal end and a proximal end, wherein the head is supported at the distal end thereof; and a tail having a distal end and a proximal end, wherein the proximal end of the tail is connected to the proximal end of the elongate body such that the tail and the elongate body bias away from one another.

The window of the clip follower that configured to receive the stop tab of the drive channel may be formed in the tail.

The clip follower may be urged in a distal direction by a constant force spring. The constant force spring may include a distal end secured against movement in the surgical clip applier, and a proximal end coiled onto itself and at least partially disposed in the window of the tail of the clip follower. The coiled proximal end of the constant force spring may draw the clip follower distally upon a coiling of the coiled proximal end of the constant force spring subsequent to a loading of a distal-most clip of the plurality of clips into a pair of jaws of the surgical clip applier.

In use, when the buckling spring is caused to be buckled so as to bow from the proximal direction to the distal direction and from the distal direction to the proximal direction, the pair of pawls may be caused to flip about a pivot point and create at least one of an audible and tactile feedback.

The channel assembly may include a pair of opposed proximal side walls, wherein each proximal side wall of the channel assembly may define a substantially V-shaped channel, and wherein each pawl may be pivotably disposed in a respective V-shaped channel of the channel assembly.

Each V-shaped channel may include a rib projecting into the channel. The rib of the V-shaped channel may be received in a notch defined in a respective pawl, wherein an axial position of each pawl in the V-shaped notch is maintained.

The drive channel may include a tail extending proximally from a proximal end thereof. The tail of the drive channel may extend between the first pawl and the second pawl, and wherein the rack member of the ratchet mechanism may be formed on the tail of the drive channel.

BRIEF DESCRIPTION OF THE DRAWINGS

The present clip applier will be more fully appreciated as the same becomes better understood from the following detailed description when considered in connection with the following drawings, in which:

FIG. 5 is a perspective view of a clip channel of the surgical clip applier of FIGS. 1-3;

FIG. 6 is an enlarged perspective view of a distal end of a pusher bar of the surgical clip applier of FIGS. 1-3;

FIG. 33 is an enlarged view of the indicated area of detail of FIG. 32;

FIG. 34 is a top, plan view of the pair of jaws and the drive channel of the surgical clip applier illustrated in FIG. 32;

FIG. 35 is a cross-sectional view as taken through 35-35 of FIG. 34;

FIG. 46 is a top, plan view of the linkage mechanism and a ratchet mechanism of the surgical clip applier of FIG. 44 when the surgical clip applier in a fully actuated condition;

FIG. 47 is a top, plan view of the pair of jaws and the drive channel of the surgical clip applier of FIG. 44 when the surgical clip applier in a fully actuated condition;

FIG. 48 is a bottom, perspective view of the pair of jaws and the drive channel of the surgical clip applier of FIG. 47;

FIG. 49 is a top, perspective view of the pair of jaws, the drive channel, the clip channel and the stack of clips of the surgical clip applier of FIGS. 1-3 when the surgical clip applier in the fully actuated condition;

FIG. 50 is a top, perspective view of the pair of jaws, the drive channel and the clip channel of the surgical clip applier of FIGS. 1-3 when the surgical clip applier in the fully actuated condition;

FIG. 55 is a longitudinal, cross-sectional view of the channel assembly of the surgical clip applier of FIGS. 1-3, illustrated in a locked out condition;

FIG. 56 is an enlarged view of the indicated area of detail of FIG. 55;

FIG. 65 is a perspective view, with parts separated, illustrating the clip follower of FIG. 63 and a constant force spring according to another embodiment of the present disclosure;

FIG. 66 is an enlarged, perspective view illustrating a connection of the constant force spring of FIG. 63-66 to the cartridge cover;

DETAILED DESCRIPTION

Figure 1:
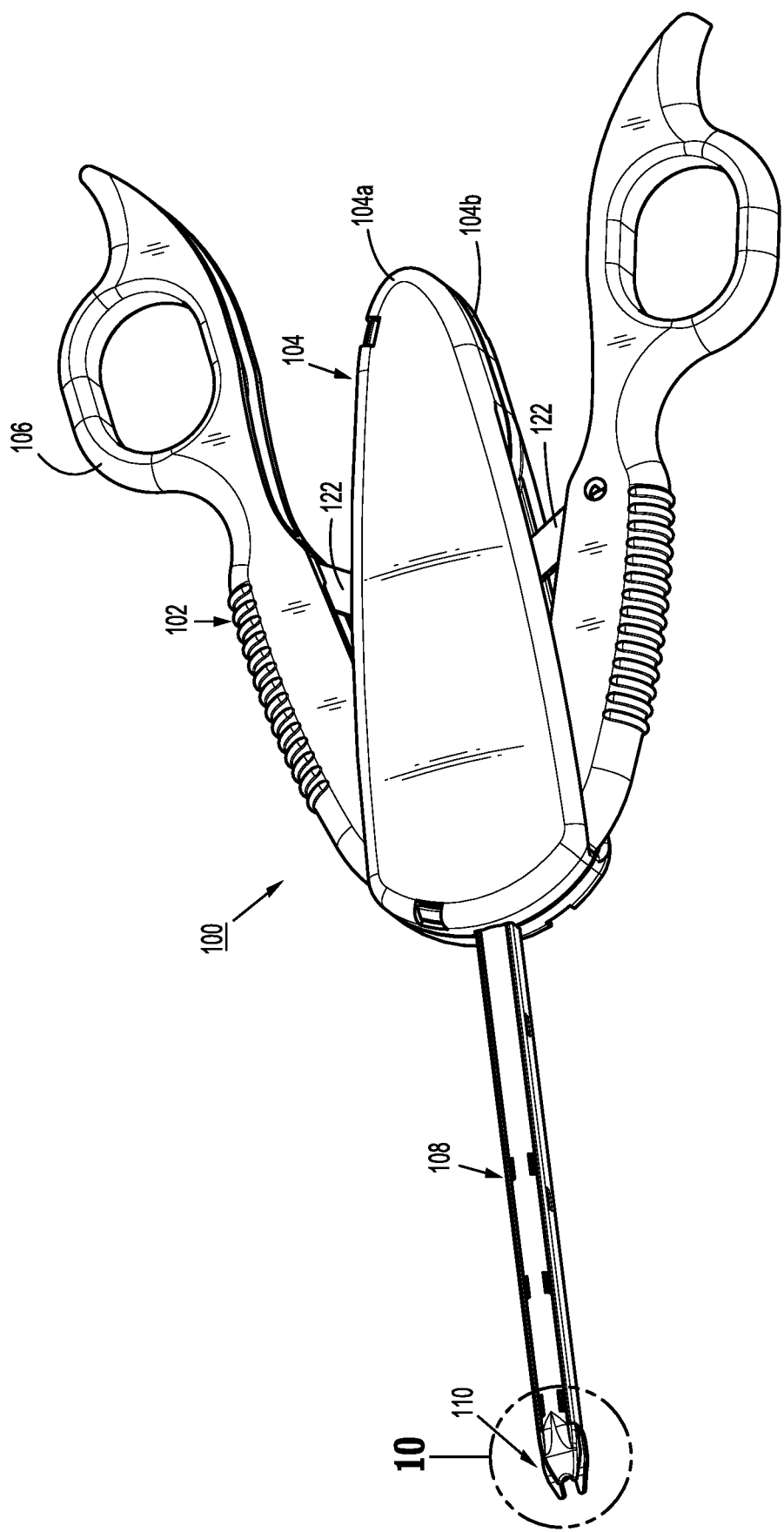
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
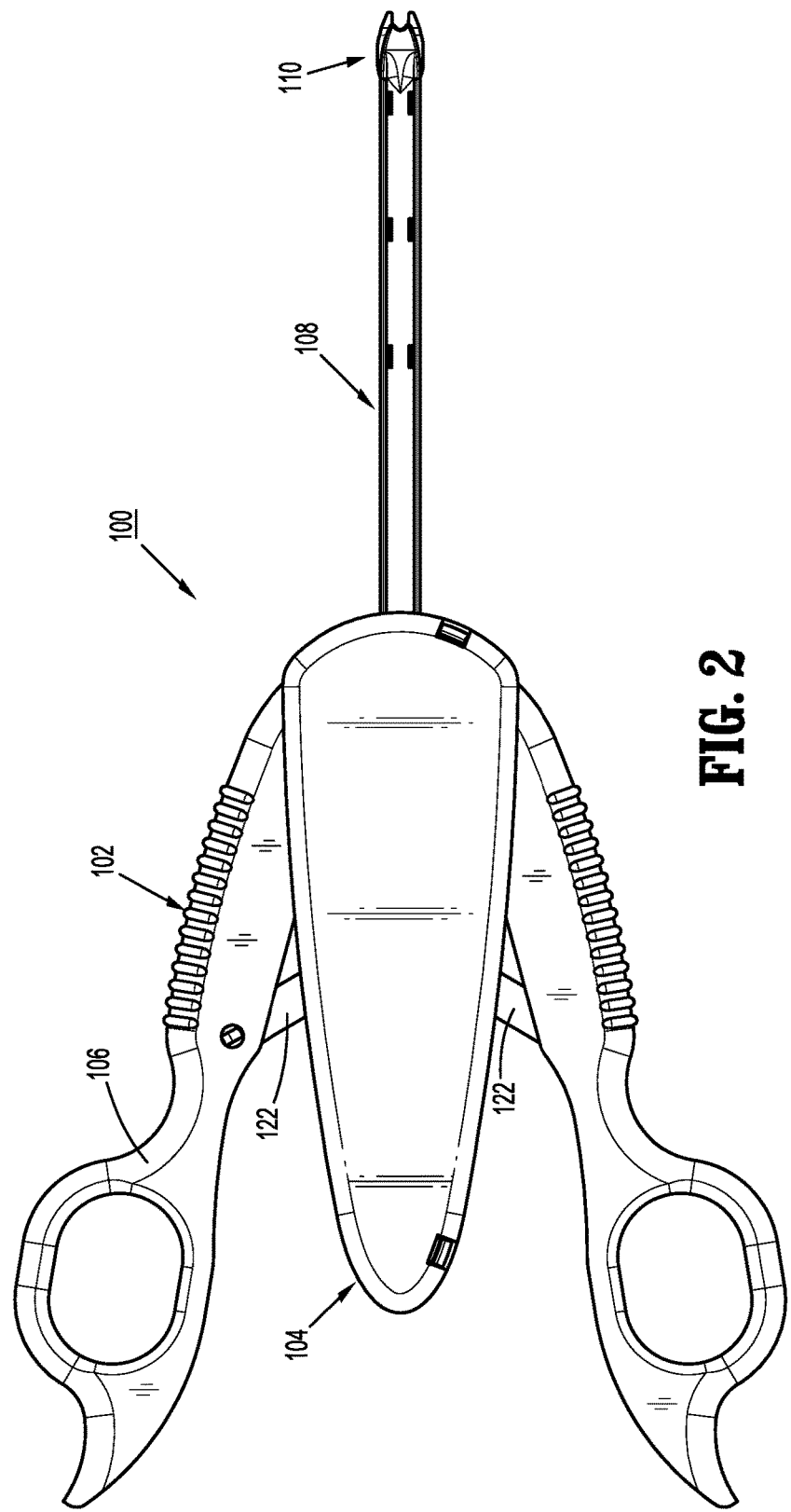
FIG. 2 is a top, plan view of the surgical clip applier of FIG. 1.
Figure 3:
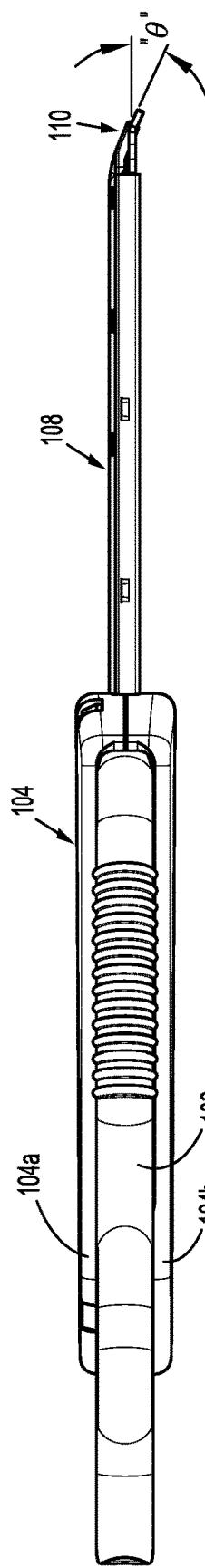
FIG. 3 is side, elevational view of the surgical clip applier of FIGS. 1 and 2.

Turning initially to FIGS. 1-3, a surgical instrument that is capable of applying a number of hemostatic clips to selected tissue for occlusion purposes during open surgical procedures is generally designated as 100.

Clip applier 100 includes a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in and supporting a jaw assembly 110.

Figure 4:
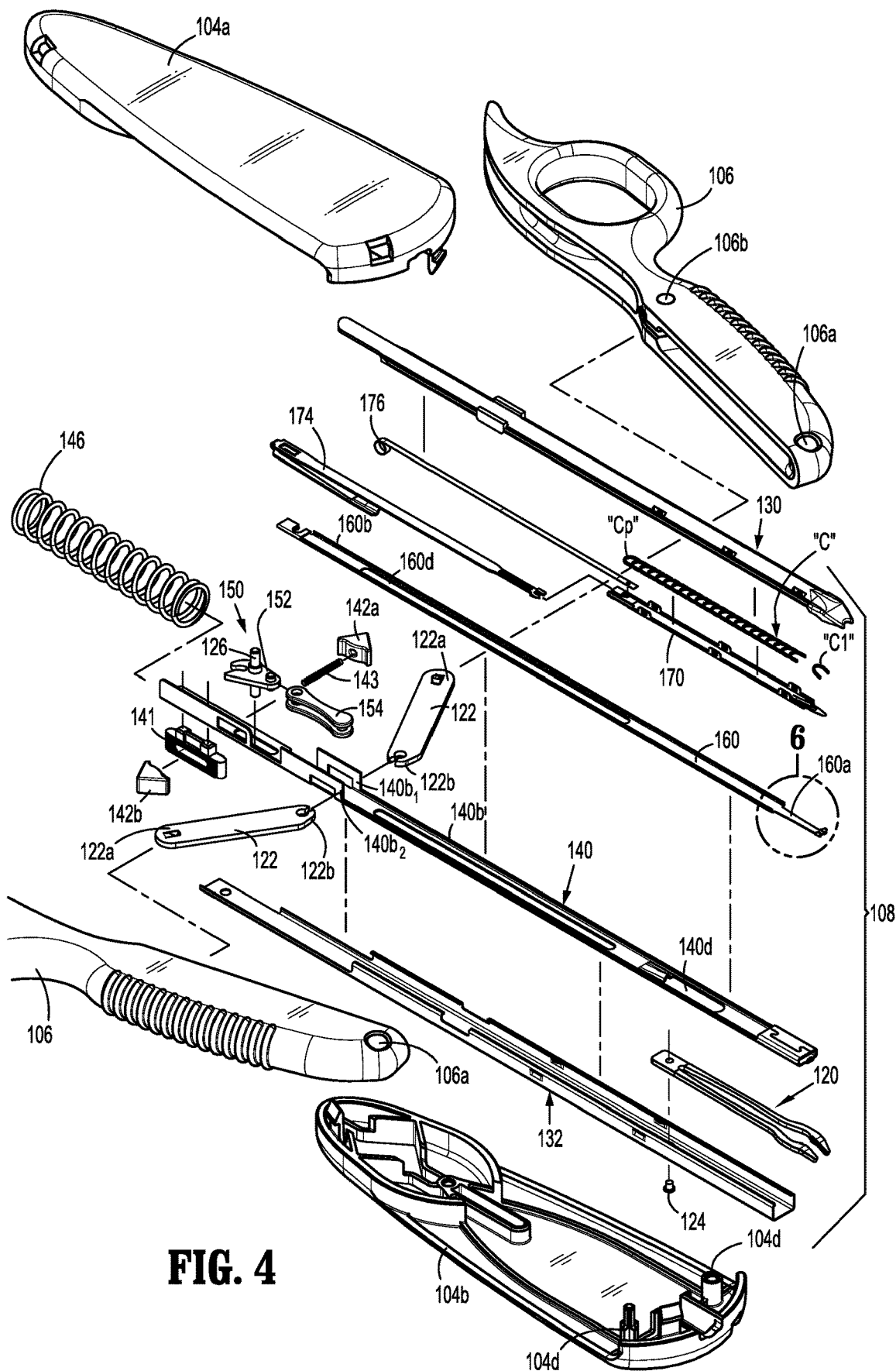
FIG. 4 is an exploded perspective view of the surgical clip applier of FIGS. 1-3.
Figure 7:
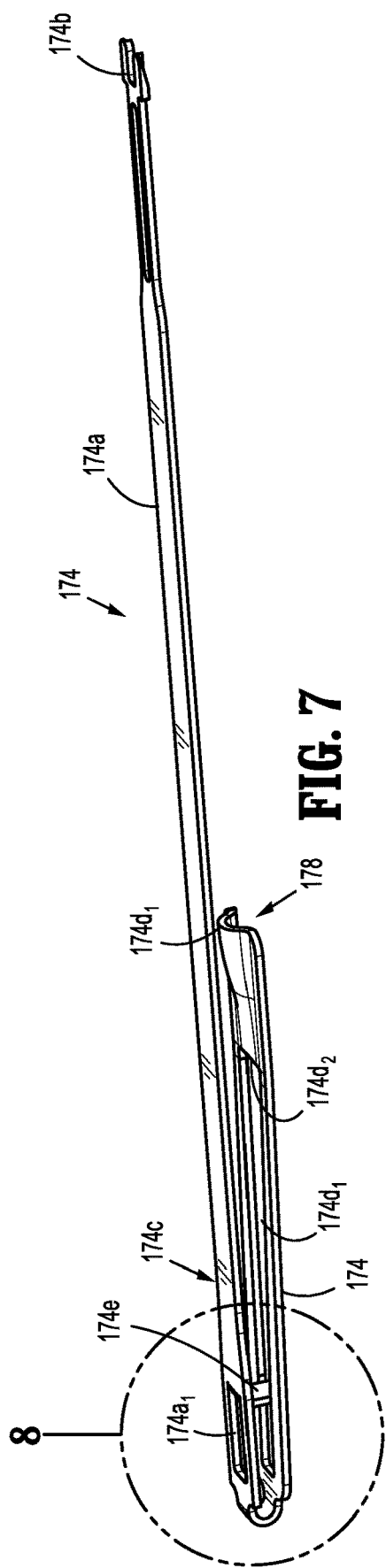
FIG. 7 is a perspective view of a clip follower of the surgical clip applier of FIGS. 1-3.

As seen in FIG. 4, housing halves 104a and 104b of clip applier 100 fit together by snap fit engagement with one another. Housing 104 is formed of a suitable plastic material.

Handles 106 are secured to housing 104 by complementary, two-part handle pivot posts 104d extending from upper housing half 104a and lower housing half 104b which complementary, two-part posts 104d couple with one another when housing halves 104a, 104b are connected or snapped to one another. Pivot posts 104d are received into respective distal apertures 106a formed in handles 106. Handle assembly 102 includes a link member 122 pivotally connected at a first end 122a thereof to each handle 106 at a pivot point 106b formed in a respective handle 106. A second end 122b of each link member 122 is pivotally connected to a respective pivot point $140b_1$, $140b_2$ defined in side walls 140b of drive channel 140.

Channel assembly 108 includes a channel or cartridge cover 130 and an outer or lower channel 132 each having a proximal end retained in housing assembly 102, between upper and lower housing halves 104a, 104b. Cartridge cover 130 includes at least one retention element configured and adapted to selectively engage, in a snap-fit engagement, a complementary or corresponding retention element provided on outer channel 132.

As seen in FIG. 4 and FIGS. 11, 21 and 22, clip applier 100 includes a drive channel 140 reciprocally supported in and extending between housing 104 of handle assembly 102 and channel assembly 108. A proximal end of a drive channel 140 is supported between upper and lower housing halves 104a, 104b of housing 104 and a distal end of drive channel 140 is supported between cartridge cover 130 and outer channel 132 of channel assembly 108.

As seen in FIGS. 11 and 26-28, a distal end of drive channel 140 is a substantially box-shaped tube including a pair of spaced apart side walls 140b interconnecting a top wall 140a and a bottom wall 140c. The distal-most end of drive channel 140 includes a tongue 140e disposed between side walls 140b and extending from and between top wall 140a and bottom wall 140c to define a pair of distal-facing openings $140e_1$, $140e_2$.

A proximal end of drive channel 140 defines an elongate pin slot 140d formed in bottom wall 140c thereof for slidable passage of a pin 124 therealong. Pin 124 is located along a central, longitudinal axis of channel assembly 108.

Figure 12:
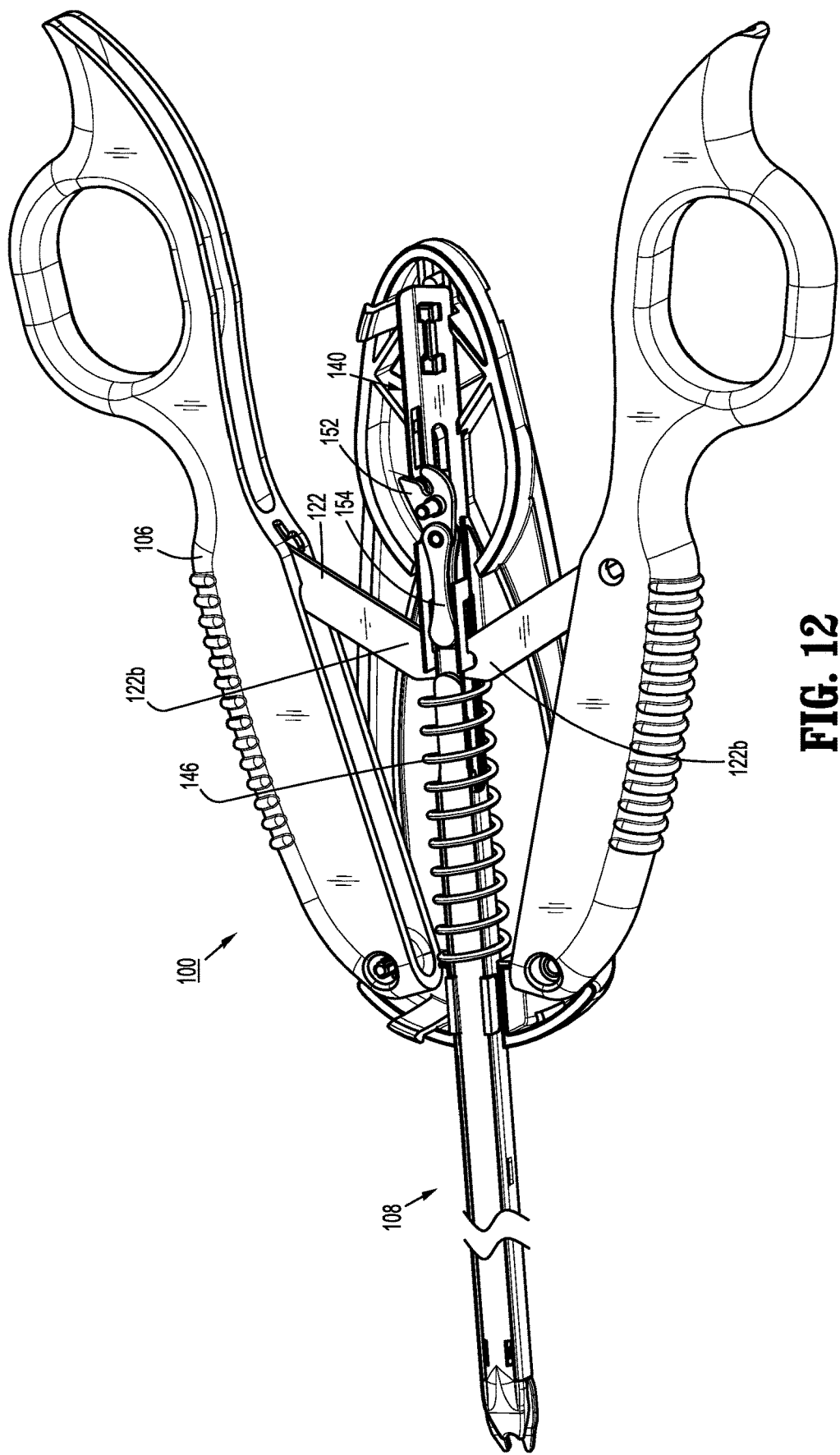
FIG. 12 is a perspective view of the surgical clip applier of FIGS. 1-3 with a housing half-section removed therefrom.
Figure 13:
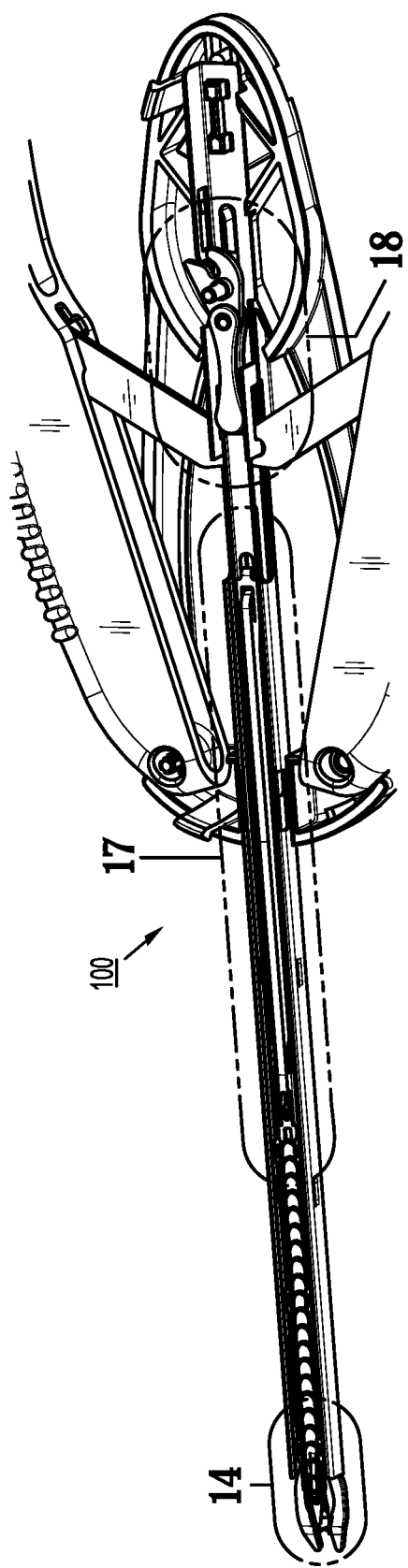
FIG. 13 is a partial enlarged view of the surgical clip applier illustrated in FIG. 12.

As seen in FIG. 4 and FIG. 12, clip applier 100 further includes a biasing member 146, in the form of a compression spring, disposed within housing 104 so as to operatively surround an intermediate portion of drive channel 140 and to abut against an inner distal surface of housing 104. Biasing member 146 functions to generally maintain drive channel 140 in a retracted or proximal-most position. In particular, biasing member 146 functions to retract or facilitate retraction of drive channel 140 following formation of a clip "C" positioned between jaws 120, and following release of handles 106.

Figure 23:
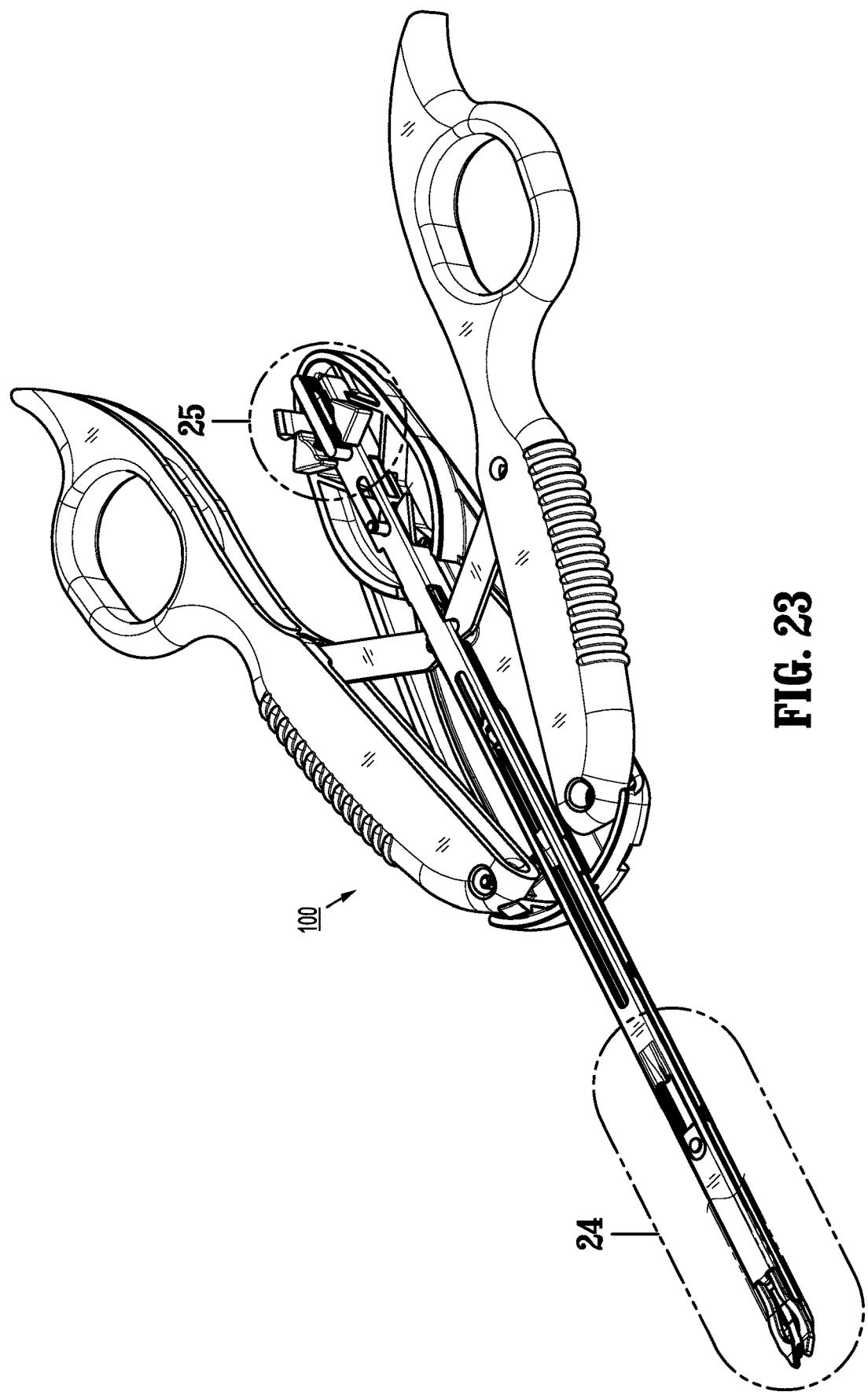
FIG. 23 is a perspective view of the surgical clip applier of FIGS. 1-3 with a housing half-section removed therefrom and illustrating the surgical clip applier in an un-actuated condition.
Figure 25:
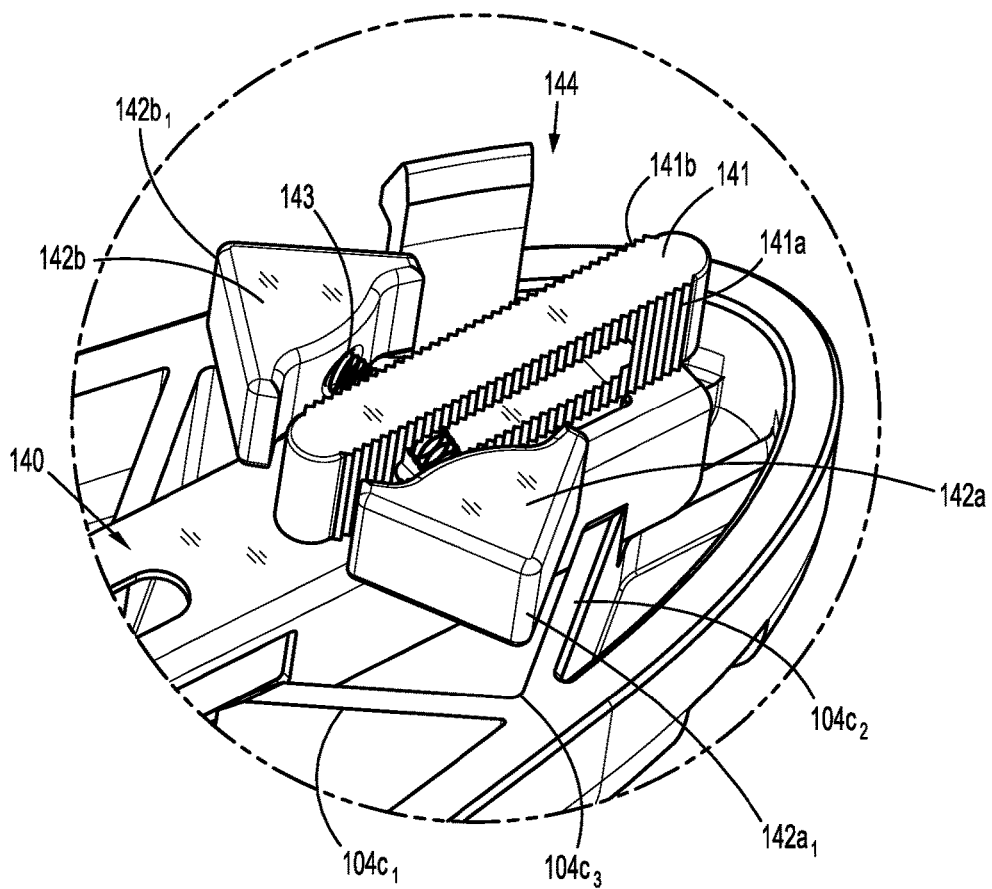
FIG. 25 is an enlarged view of the indicated area of detail of FIG. 23.

As seen in FIGS. 23 and 25, a proximal end of drive channel 140 supports a ratchet rack member 141 and secured thereto, wherein ratchet rack member 141 is movable together with drive channel 140. Ratchet rack member 141 defines a first set of teeth 141a configured and adapted to engage with a first ratchet pawl 142a, and a second set of teeth 141b configured and adapted to engage a second ratchet pawl 142b, wherein the first set and the second set of teeth 141a, 141b are disposed on opposed sides of rack member 141. First ratchet pawl 142a and second ratchet pawl 142b are each supported in housing 104, with first ratchet pawl 142a and second ratchet pawl 142b being disposed on opposed sides of ratchet rack member 141. Rack member 141 and pawls 142a, 142b define a ratchet mechanism 144. In use, as drive channel 140 is moved axially, rack member 141 is also moved axially therewith. In operation, pawls 142a, 142b reverse their direction when a distal/proximal end of a longitudinally extending slot formed in rack member 141 impacts a snap-over ratchet spring 143, causing ratchet spring 143 to flip, and in turn, causing pawls 142a, 142b to flip or reverse their direction, as will be discussed in greater detail below.

Each pawl 142a, 142b is pivotally supported in upper housing half 104a and lower housing half 104b at a location wherein each pawl 142a, 142b is in substantial operative engagement with respective rack teeth 141a, 141b of rack member 141. Pawls 142a, 142b are engageable with rack member 141 to restrict longitudinal movement of rack member 141 and, in turn, drive channel 140.

Additionally, as seen in FIG. 25, each pawl 142a, 142b has a substantially triangular profile, wherein a remote corner $142a_1$, $142b_1$ of each pawl 142a, 142b extends away from rack member 141 and is situated within an internal corner $104c_3$ of a pair of walls $104c_1$, $104c_2$ defined in upper housing half 104a and lower housing half 104b. The interface of the remote corner $142a_1$, $142b_1$ of each pawl 142a, 142b and internal corner $104c_3$ of a pair of walls $104c_1$, $104c_2$ defines a pivot point for pawls 142a, 142b.

Figure 36:
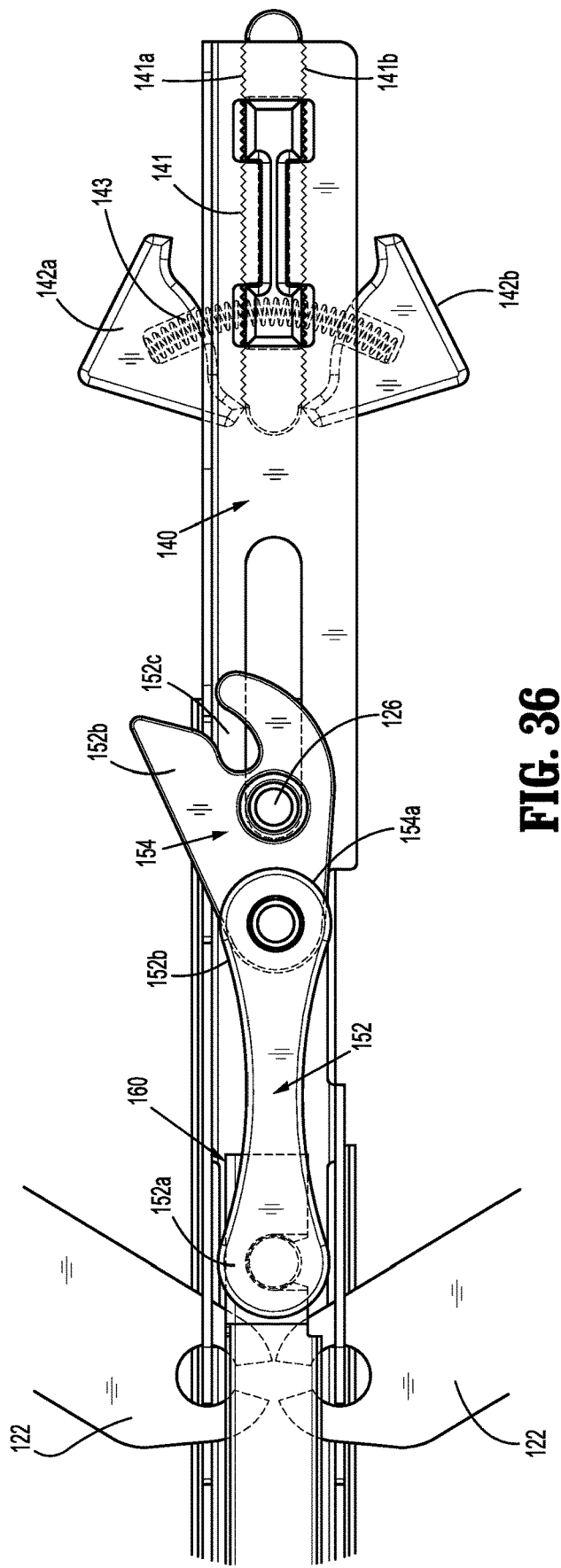
FIG. 36 is an enlarged view of the indicated area of detail of FIG. 32.
Figure 43:
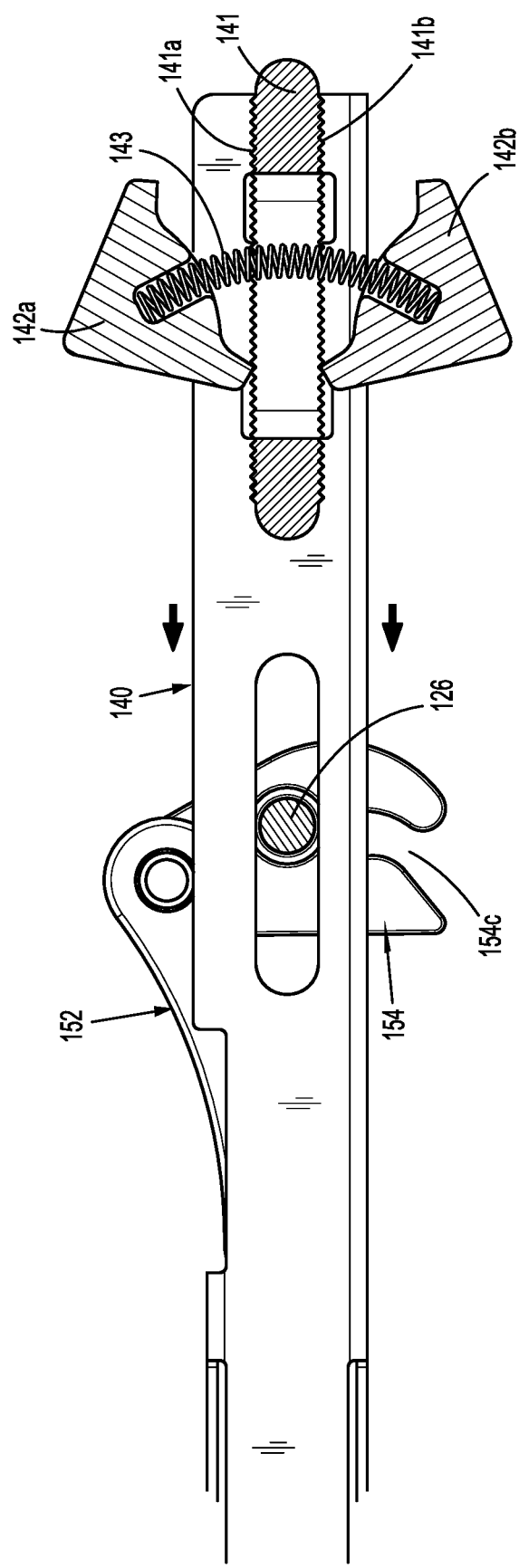
FIG. 43 is a cross-sectional view as taken through 43-43 of FIG. 40.
Figures 44, 45:
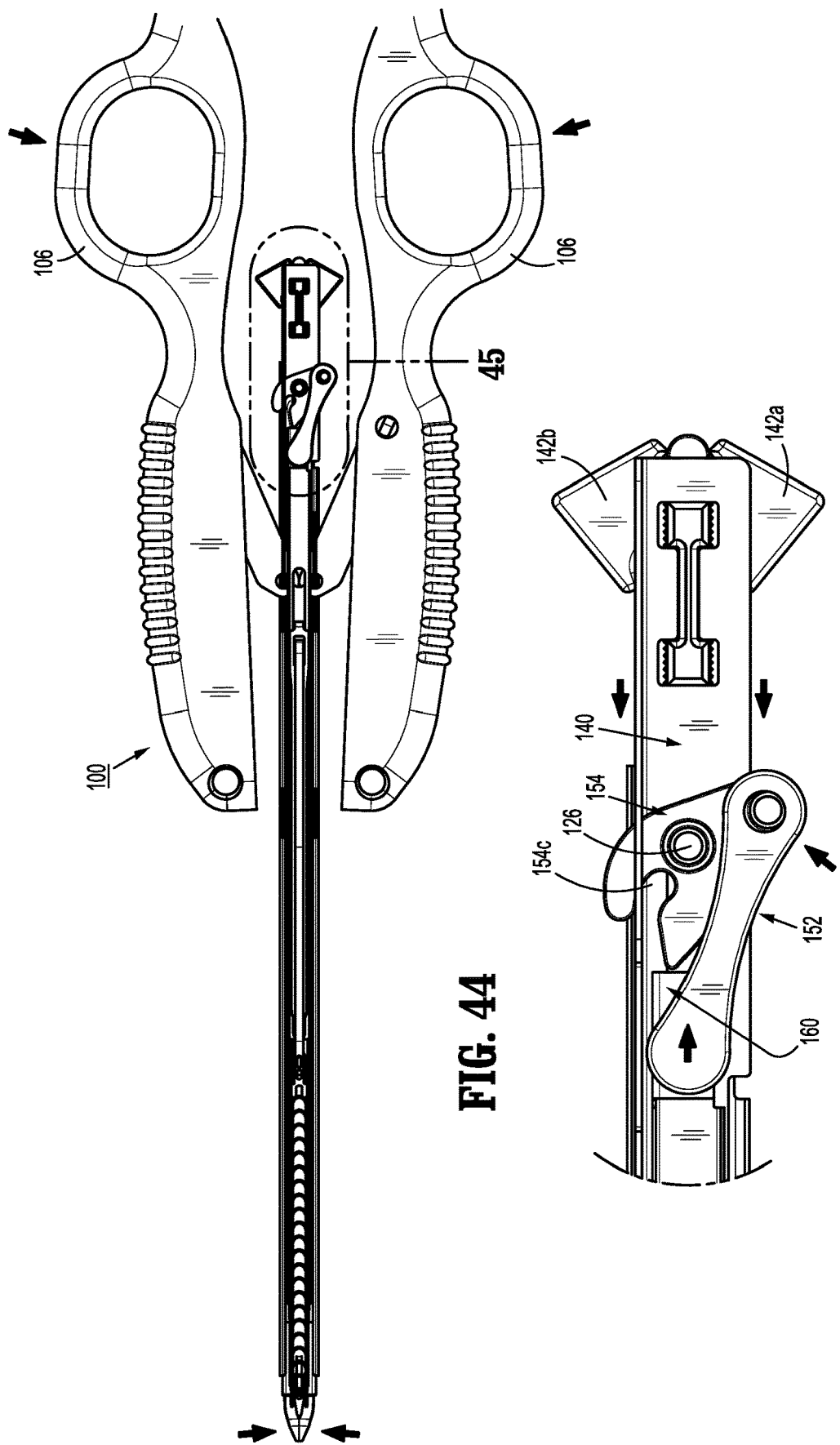
FIG. 44 is a top, plan view of the surgical clip applier of FIGS. 1-3 with the housing removed therefrom and illustrating the surgical clip applier in a fully actuated condition.
FIG. 45 is an enlarged view of the indicated area of detail of FIG. 44.
Figure 51:
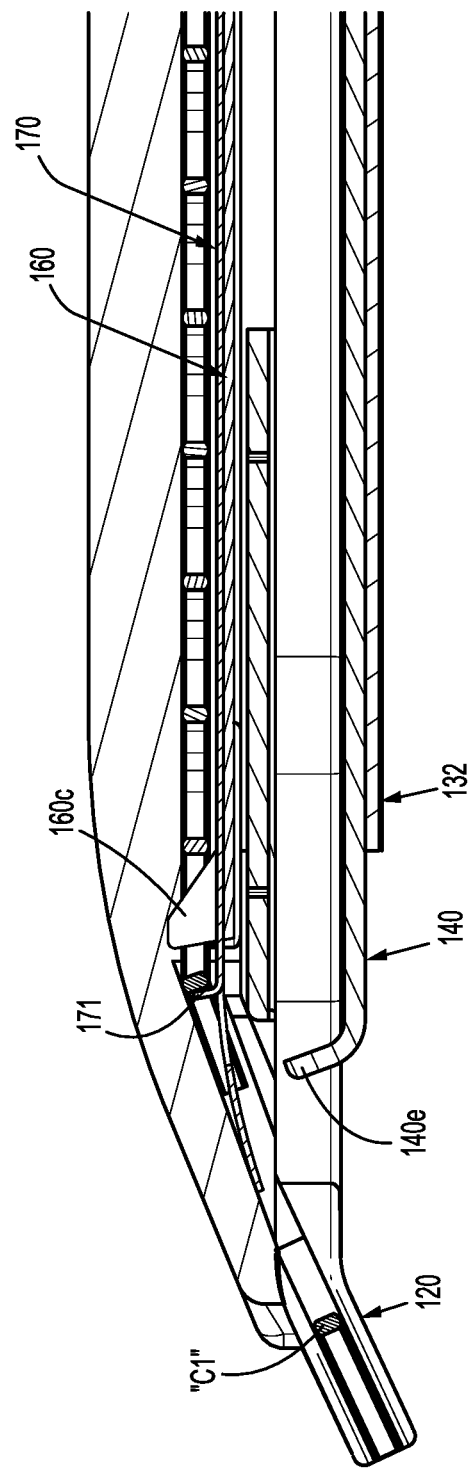
FIG. 51 is a longitudinal, cross-sectional view of the distal end of the surgical clip applier illustrated in FIG. 44.

Ratchet mechanism 144 includes a snap-over ratchet spring 143, in the form of a coil spring, interposed between pawls 142a, 142b and extending through and across rack member 141. Snap-over spring 143 functions to maintain the teeth of pawls 142a, 142b in engagement with the respective rack teeth 141a, 141b of rack member 141 as rack member 141 is axially translated. When pawls 142a, 142b are in a first position (permitting drive channel 140 to move in a distal direction), snap-over spring 143 bulges or buckles in a proximal direction, as seen in FIGS. 36 and 43, and when pawls 142a, 142b are in a second position (permitting drive channel 140 to move in a proximal direction), snap-over spring 143 bulges or buckles in a distal direction, as seen in FIG. 46.

In operation, when drive channel 140 is moved to the distal-most position, a surface of rack member 141 engages distally bulging snap-over spring 143 to reverse the direction of buckling thereof, and thus reverse or change the orientation of pawls 142a, 142b. Additionally, when drive channel 140 is moved to the proximal-most position and rack teeth 141a, 141b of rack member 141 have once again cleared pawls 142a, 142b, another surface of rack member 141 engages proximally bulging snap-over spring 143 to again reverse the direction of buckling thereof, and thus again reverse or change the orientation of pawls 142a, 142b.

Clip applier 100 is provided with audible/tactile indication or feedback when pawls 142a, 142b are flipped at either end of the stroke of drive channel 140. In particular, when pawls 142a, 142b flip pawls 142a, 142b are accelerated by snap-over spring 143 and slap against the pair of walls $104c_1$, $104c_2$ of housing 104, thereby providing the user feedback that end of a stroke has been reached.

As seen in FIGS. 1-4 and FIGS. 10, 34 and 35, clip applier 100 includes a pair of jaws 120 mounted on or at a distal end of channel assembly 108 and actuatable by handles 106 of handle assembly 102. The pair of jaws 120 are formed of a suitable biocompatible material such as, for example, stainless steel or titanium.

The pair of jaws 120 are mounted in a distal end of outer channel 132 via a pin or a rivet 124 extending through the reciprocation limiting slot 140d of drive channel 140 such that jaws 120 are longitudinally stationary relative to outer channel 132 and drive channel 140. The pair of jaws 120 includes a first jaw member 121a, and a second jaw member 121b, wherein first jaw member 121a extends through first distal-facing openings $140e_1$ of drive channel 140, and wherein second jaw member 121b extends through first distal-facing openings $140e_2$ of drive channel 140. In this manner, tongue 140e of drive channel 140 extends between first jaw member 121a, and second jaw member 121b.

As seen in FIG. 4, the pair of jaws 120 defines a channel 120a therebetween for receipt of a surgical clip "C1" therein.

As seen in FIG. 3, a distal end of each jaw member 121a, 121b is angled at an angle "θ" of approximately between 15°-22.5° relative to a longitudinal axis of channel assembly 108 to enable an end user to better visualize a surgical clip disposed in the pair of jaws 120 by altering a line of sight of the end user to jaw members 121a, 121b of the pair of jaws 120. In this manner, the end user may better visualize and verify a presence of a surgical clip in the pair of jaws 120 while the surgical clip is being placed on or over a vessel.

As seen in FIG. 4 and FIGS. 6, 15, 16, 19 and 20, clip applier 100 includes a clip pusher bar 160 slidably disposed against drive channel 140, at a location between drive channel 140 and cartridge cover 130. Pusher bar 160 includes a distal end 160a defining a pusher 160c configured and adapted to selectively engage/move a distal-most surgical clip "C1" stored in surgical clip applier 100. Pusher bar 160 further includes a proximal end 160b operatively connected to drive channel 140. Pusher bar 160 further defines an elongate window 160d therein for operative receipt of a proximal end of a constant force spring 176 therein, as will be discussed in greater detail below.

As seen in FIG. 4 and FIGS. 13, 18, 31 and 32, clip applier 100 further includes linkage mechanism 150 having a distal, driven link arm 154 having a first, distal end 154a pivotally connected to proximal end 160b of pusher bar 160. Linkage mechanism 150 further includes a proximal, driver link arm 152 having a first, distal end 152a pivotally connected to a second, proximal end 154b of driven link arm 154, and a second, proximal end 152b defining an arcuate slot 152c configured to slidably receive a tab 140f of drive channel 140. Arcuate slot 152c is open ended and is only engaged by tab 140f of drive channel 140 during select portions of a distal and proximal translation thereof, as will be described in greater detail below. Driver link arm 152 defines a central eyelet 152c for pivotal connection to a pin 126, such that driver link arm 152 is axially fixed with respect to housing 104.

As seen in FIG. 4 and FIG. 5, clip applier 100 further includes a clip carrier 170 fixedly disposed within channel assembly 108 and disposed against pusher bar 160, at a location between pusher bar 160 and cartridge cover 130. Clip carrier 170 is generally a U-shaped channel structure having a lower wall 170a and a pair of side walls 170b defining a channel 170c between lower wall 170a and cartridge cover 130.

As seen in FIG. 4 and FIG. 33, a stack of surgical clips "C" is loaded and/or retained within channel 170c defined by clip carrier 170 and cartridge cover 130 in a manner so as to slide therewithin and/or therealong. Clip carrier 170 is configured and dimensioned to slidably retain the stack or plurality of surgical clips "C" in tip-to-tail fashion therewithin.

Figure 14:
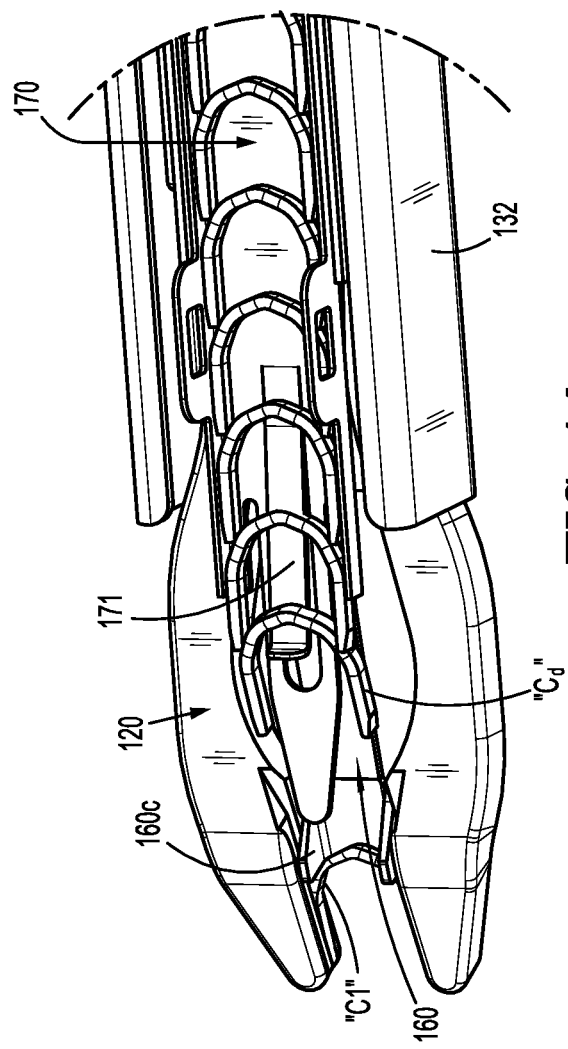
FIG. 14 is an enlarged view of the indicated area of detail of FIG. 13.
Figure 15:
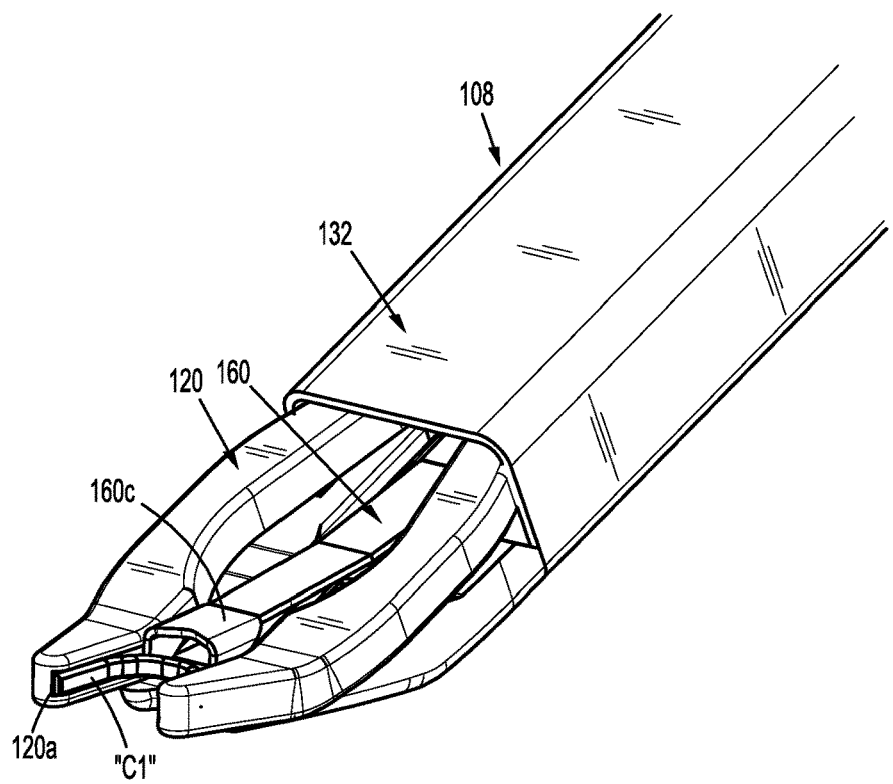
FIG. 15 is a perspective view of the distal end of the surgical clip applier of FIGS. 1-3.
Figure 16:
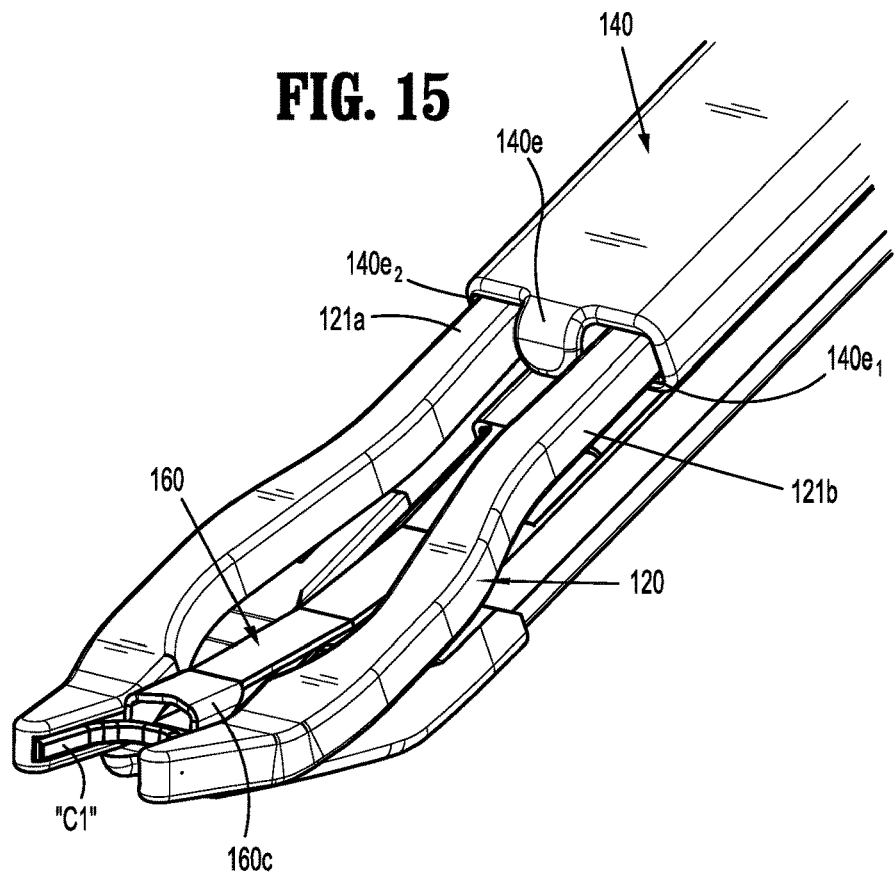
FIG. 16 is a perspective view of the distal end of the surgical clip applier of FIGS. 1-3 with the clip channel removed therefrom.

As seen in FIG. 5 and FIG. 14, a distal end of clip carrier 170 includes a resilient central tang 171. Tang 171 is configured and adapted to selectively engage a backspan of a distal-most surgical clip "$C_d$" of the stack of surgical clips "C" retained within carrier 170 to thereby prevent the stack of surgical clips "C" within channel 170c of clip carrier 170.

As seen in FIG. 4 and FIGS. 7-9 and 29, clip applier 100 further includes a clip follower 174 at least partially slidably disposed within channel 170c of clip carrier 170. As will be discussed in greater detail below, clip follower 174 is positioned behind the stack of surgical clips "C" and is provided to urge the stack of surgical clips "C" forward during an actuation of clip applier 100. As will also be described in greater detail below, clip follower 174 is actuated by a constant force spring 176 upon the advancement, by the pusher bar 160, of the distal-most surgical clip "$C_d$" distally passed the tang 171 of the clip carrier 170, during a firing of clip applier 100.

Clip follower 174 includes an elongate body 174a having a distal end portion 174b configured and dimensioned for passage through channel 170c of clip carrier 170. Distal end portion 174b of clip follower 174 is configured to seat against a backspan of a proximal-most clip "$C_p$" of the stack of surgical clips "C".

Clip follower 174 includes a proximal end portion 174c folded over onto itself to define a tail 174d such that proximal end portion 174c is in the form of a leaf spring. Proximal end portion 174c defines an upper window $174a_1$ formed in a proximal portion of elongate body 174a, and a lower window $174d_1$ formed in tail 174d and overlying or in registration with upper window $174a_1$. Clip follower 174 includes a tab 174e extending between elongate body 174a and tail 174d.

Clip follower 174 is fabricated from a resilient material such that tail 174d of clip follower 174 is lightly spring-biased against a surface of drive channel 140.

Turning momentarily to FIGS. 63-70, an alternate embodiment of a clip follower 274 is shown and will be described. Clip follower 274 is substantially similar to clip follower 174 and thus will only be described in detail herein to the extent necessary to describe differences in construction and functions thereof. As seen in FIGS. 63-65 and 67-70, clip follower 274 includes a proximal fin 274d projecting transversely from a proximal end portion 274c. Proximal fin 274d defines a proximal surface $274d_1$ having a concave arcuate profile configured to receive and seat with a coiled or spooled portion 176c of a constant force spring 176.

Figure 9:
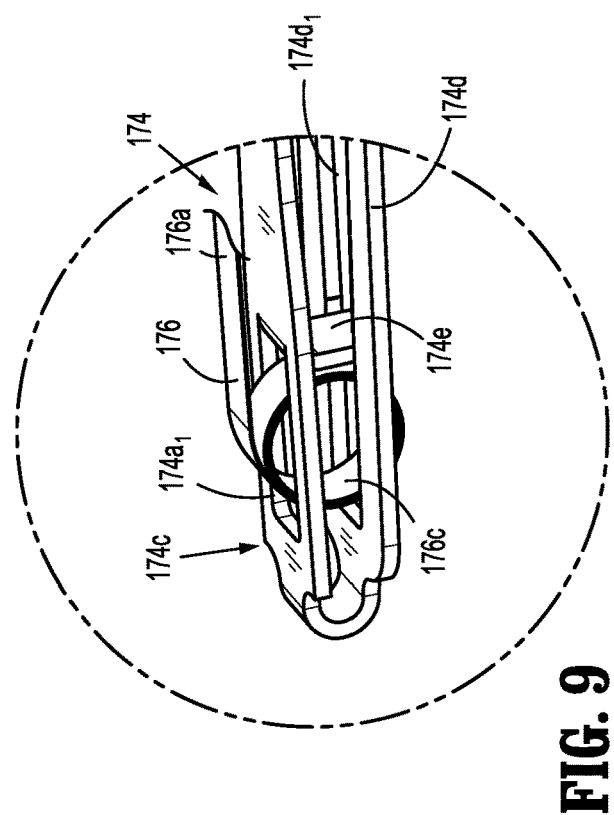
FIG. 9 is an enlarged view of a proximal end of the clip follower illustrating a biasing member associated therewith.
Figure 8:
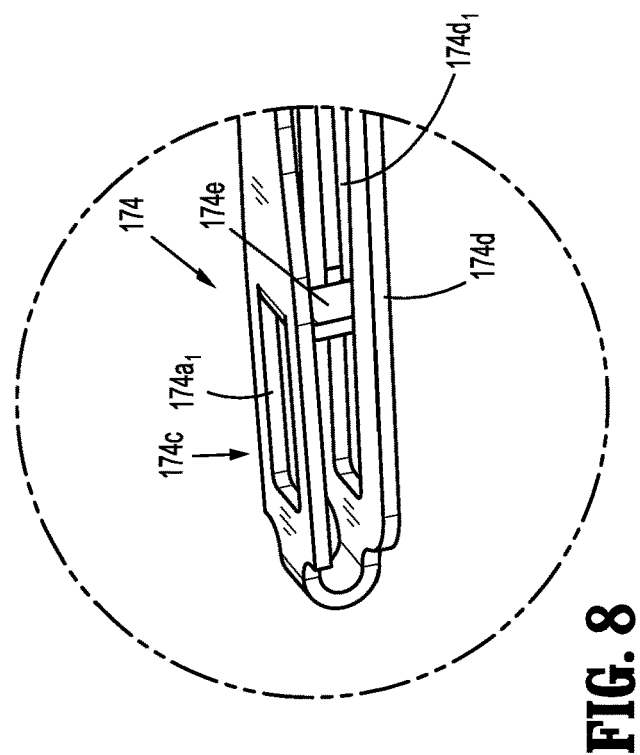
FIG. 8 is an enlarged view of the indicated area of detail of FIG. 7.
Figure 10:
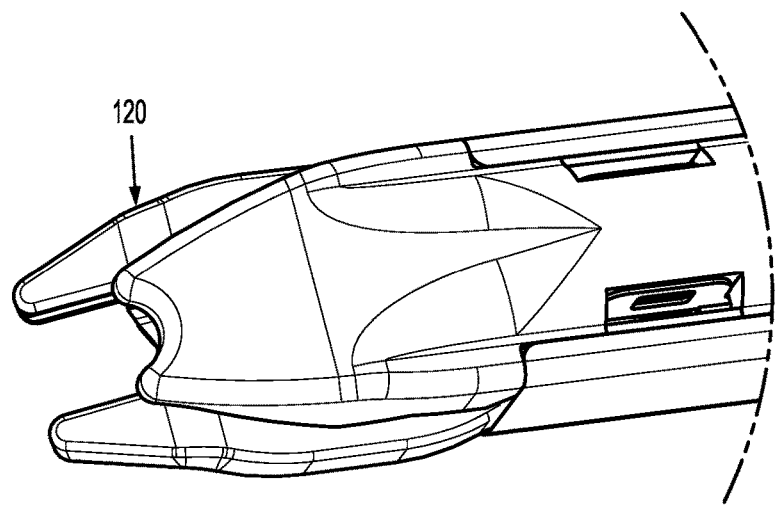
FIG. 10 is a perspective view of a distal end of the surgical clip applier of FIGS. 1-3.
Figure 11:
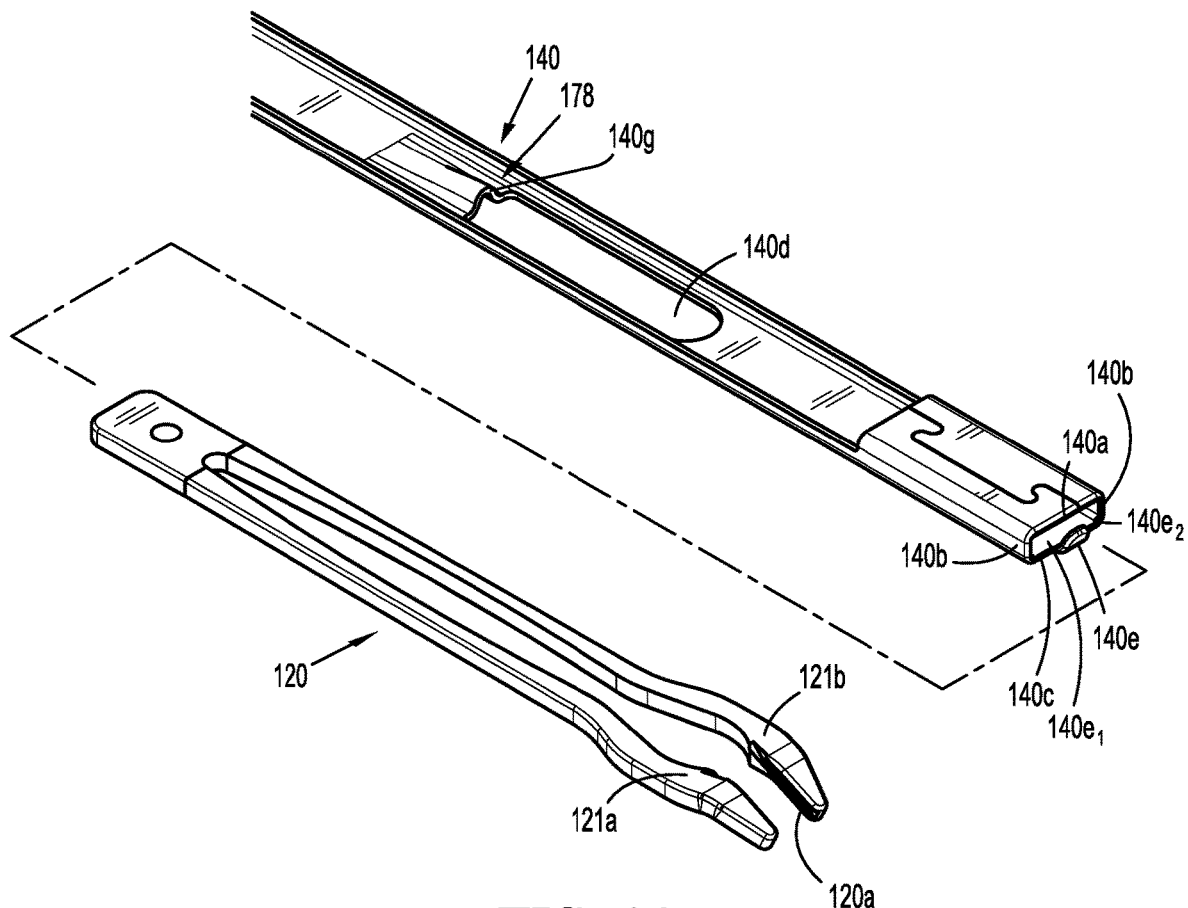
FIG. 11 is a perspective view, with parts separated of a pair of jaws and a distal end of a drive channel of the surgical clip applier of FIGS. 1-3.

Turning now to and as seen in FIGS. 4, 5 and 9, clip applier 100 includes a constant force spring 176 supported in handle assembly 104 and channel assembly 108. Constant force spring 176 is in the form of a ribbon including a body portion 176a having a distal end 176b, and a proximal end 176c coiled onto itself to form a spool.

Figure 17:
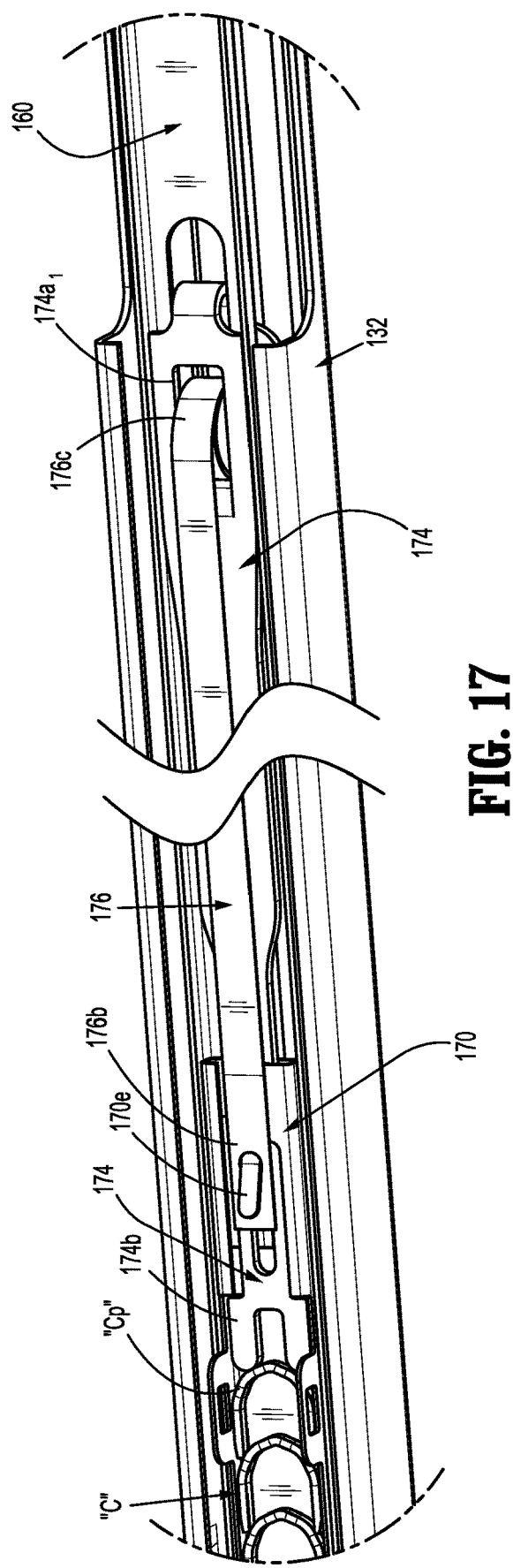
FIG. 17 is an enlarged view of the indicated area of detail of FIG. 13.
Figure 18:
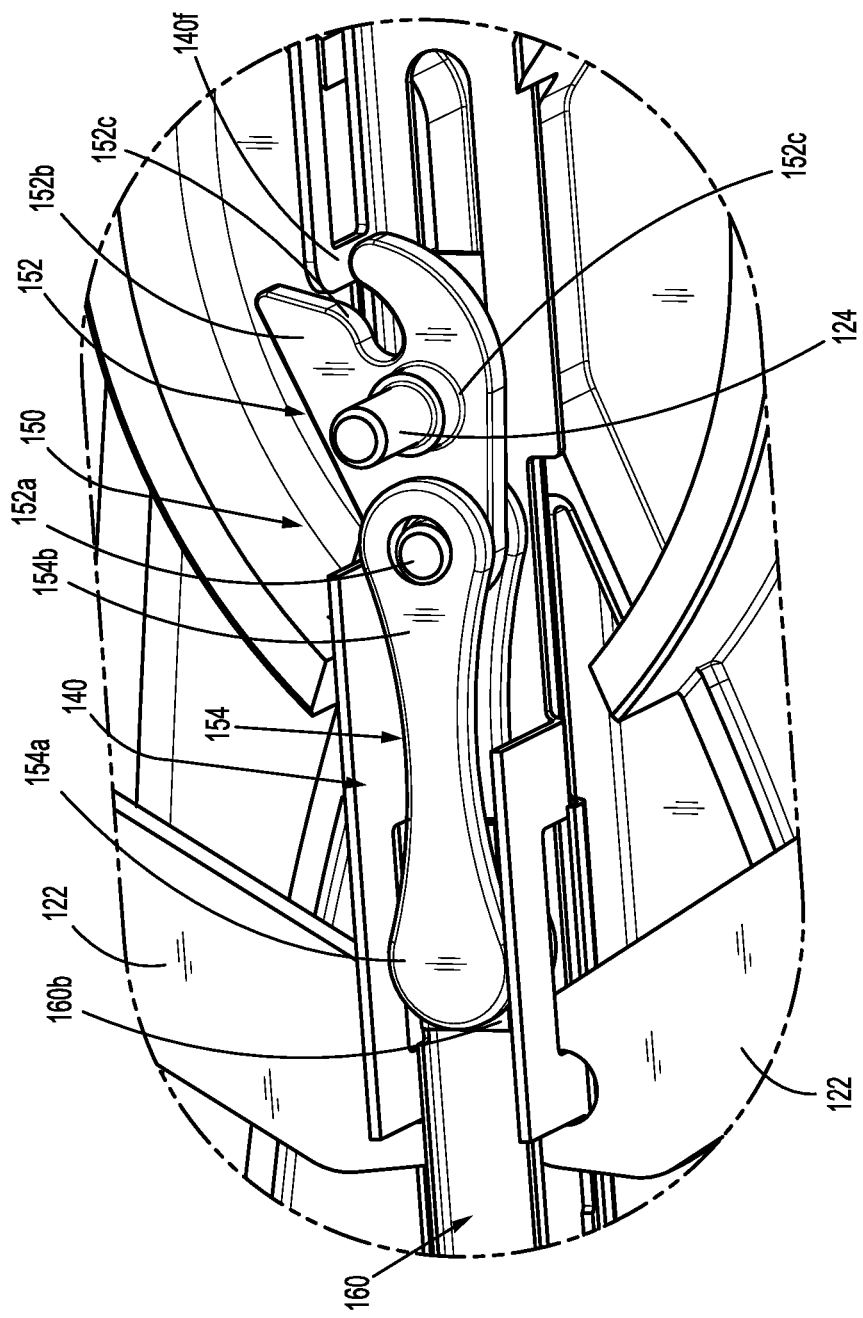
FIG. 18 is an enlarged view of the indicated area of detail of FIG. 13.
Figure 19:
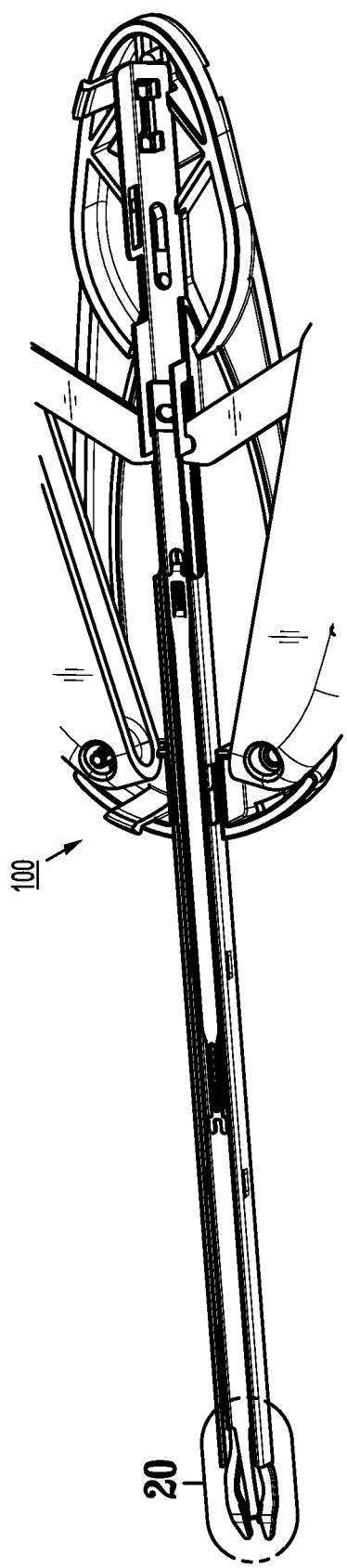
FIG. 19 is the partial enlarged view of the surgical clip applier illustrated in FIG. 13 with a stack of clips and a linkage mechanism removed.
Figure 20:
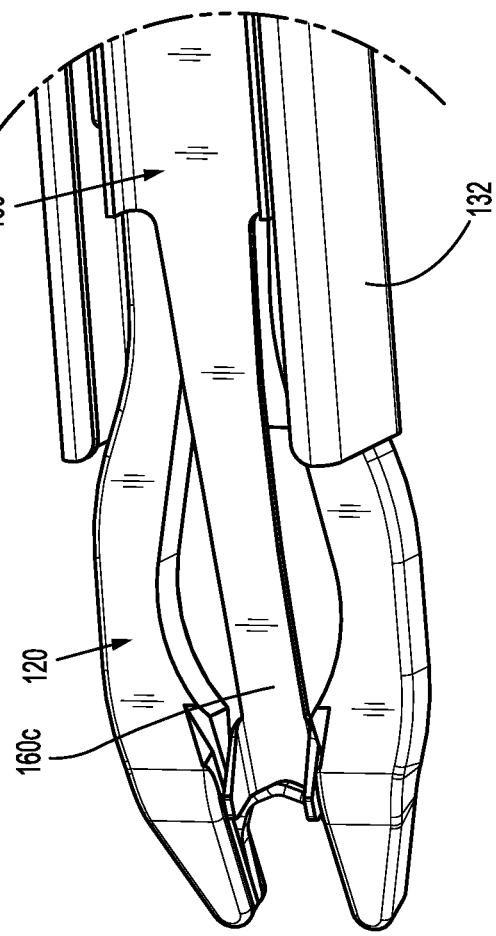
FIG. 20 is an enlarged view of the indicated area of detail of FIG. 19.
Figure 21:
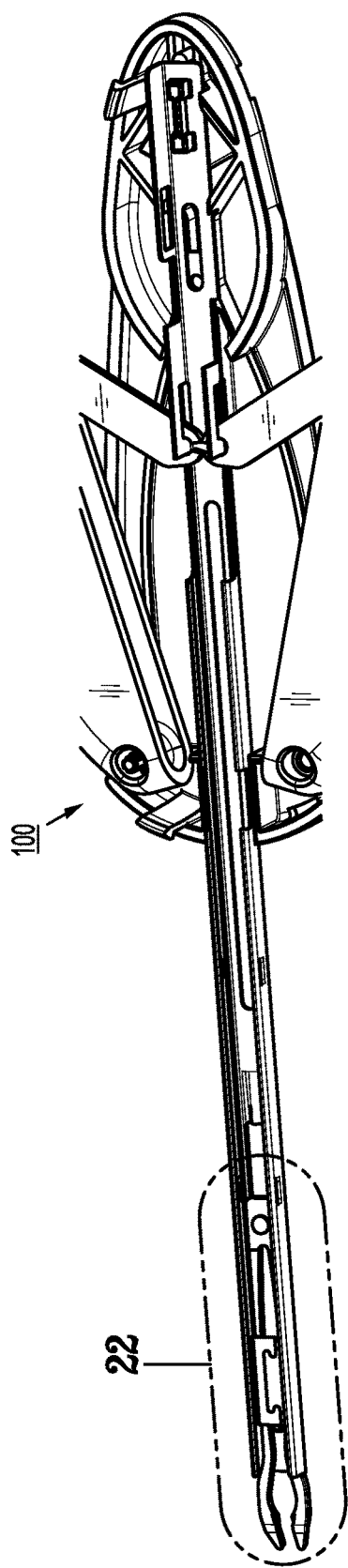
FIG. 21 is the partial enlarged view of the surgical clip applier illustrated in FIG. 13 with the stack of clips, the linkage mechanism, and a pusher bar removed.
Figure 22:
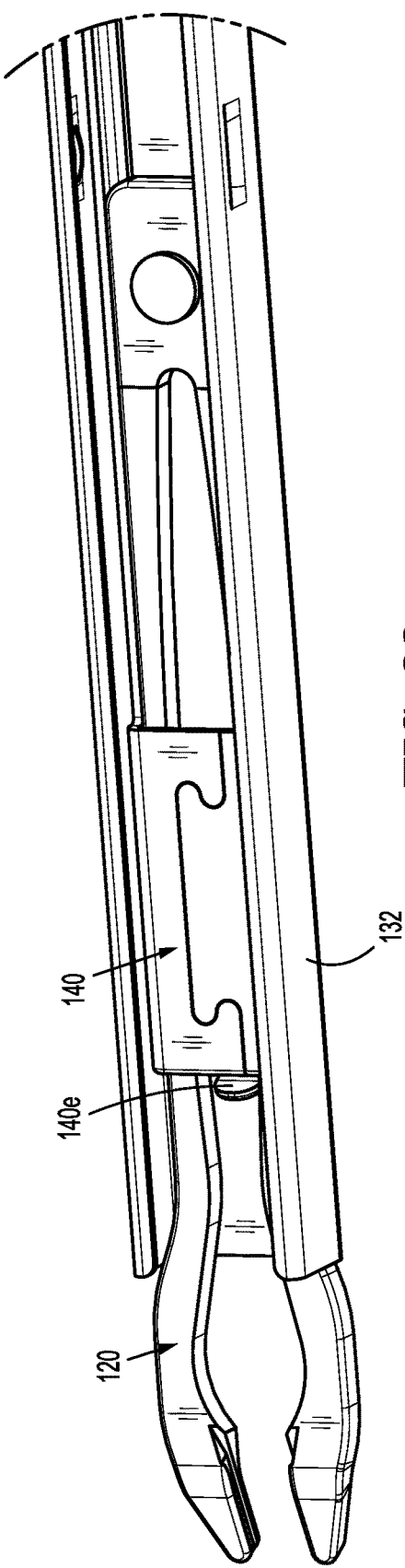
FIG. 22 is an enlarged view of the indicated area of detail of FIG. 21.
Figure 30:
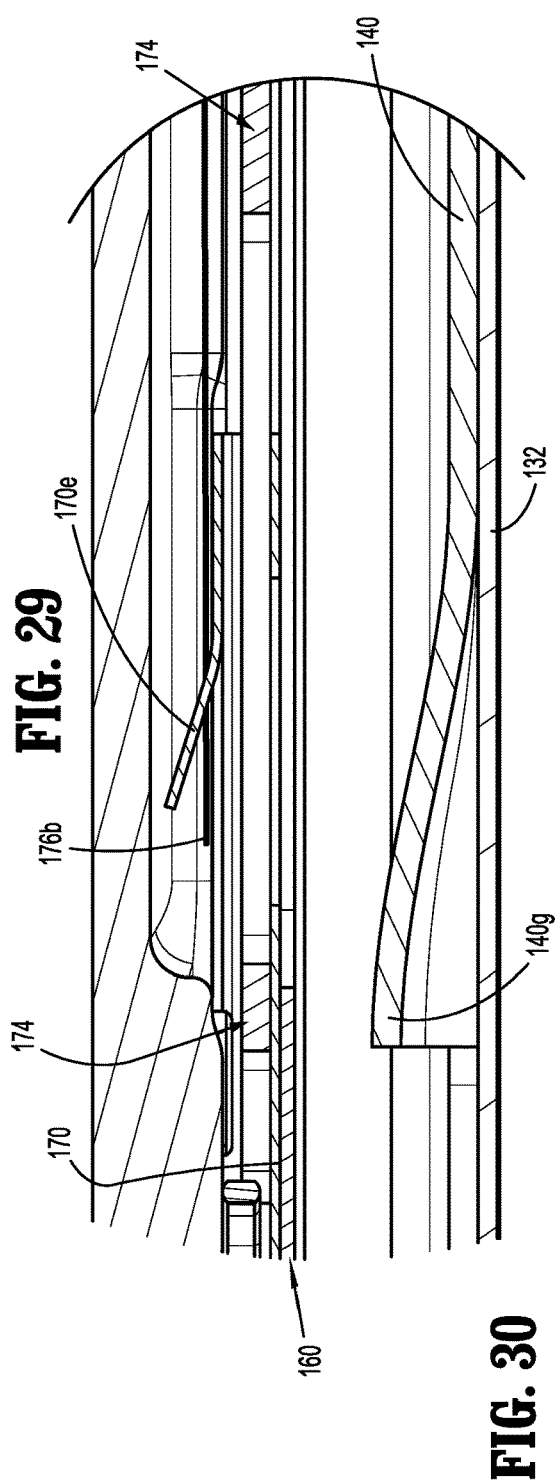
FIG. 30 is an enlarged view of the indicated area of detail of FIG. 29.
Figure 31:
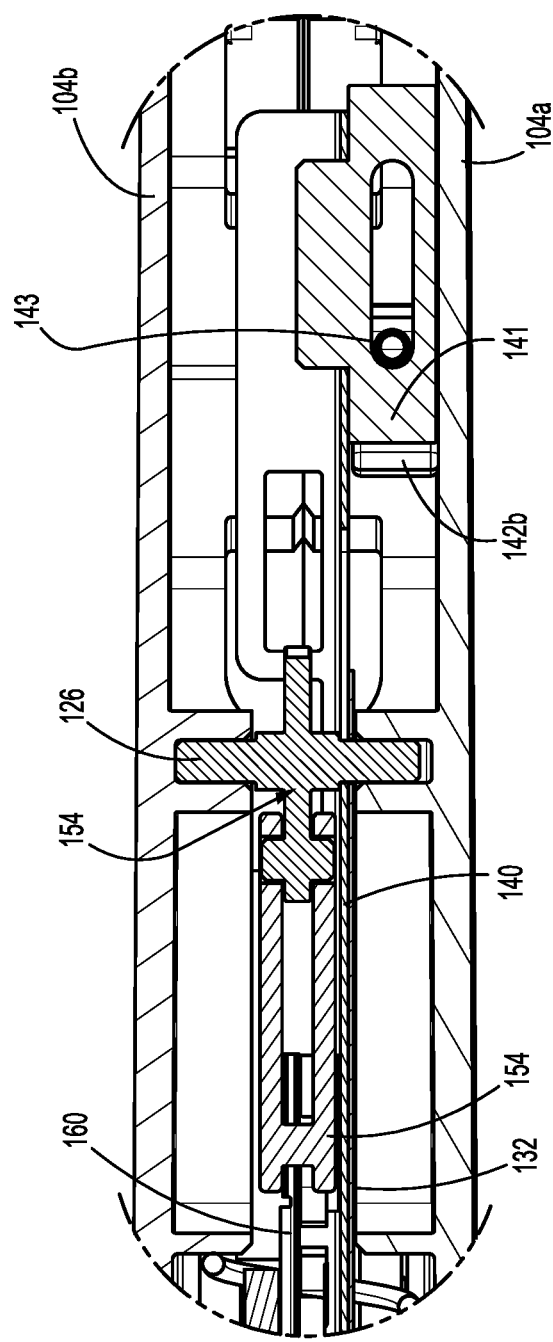
FIG. 31 is an enlarged view of the indicated area of detail of FIG. 27.
Figure 32:
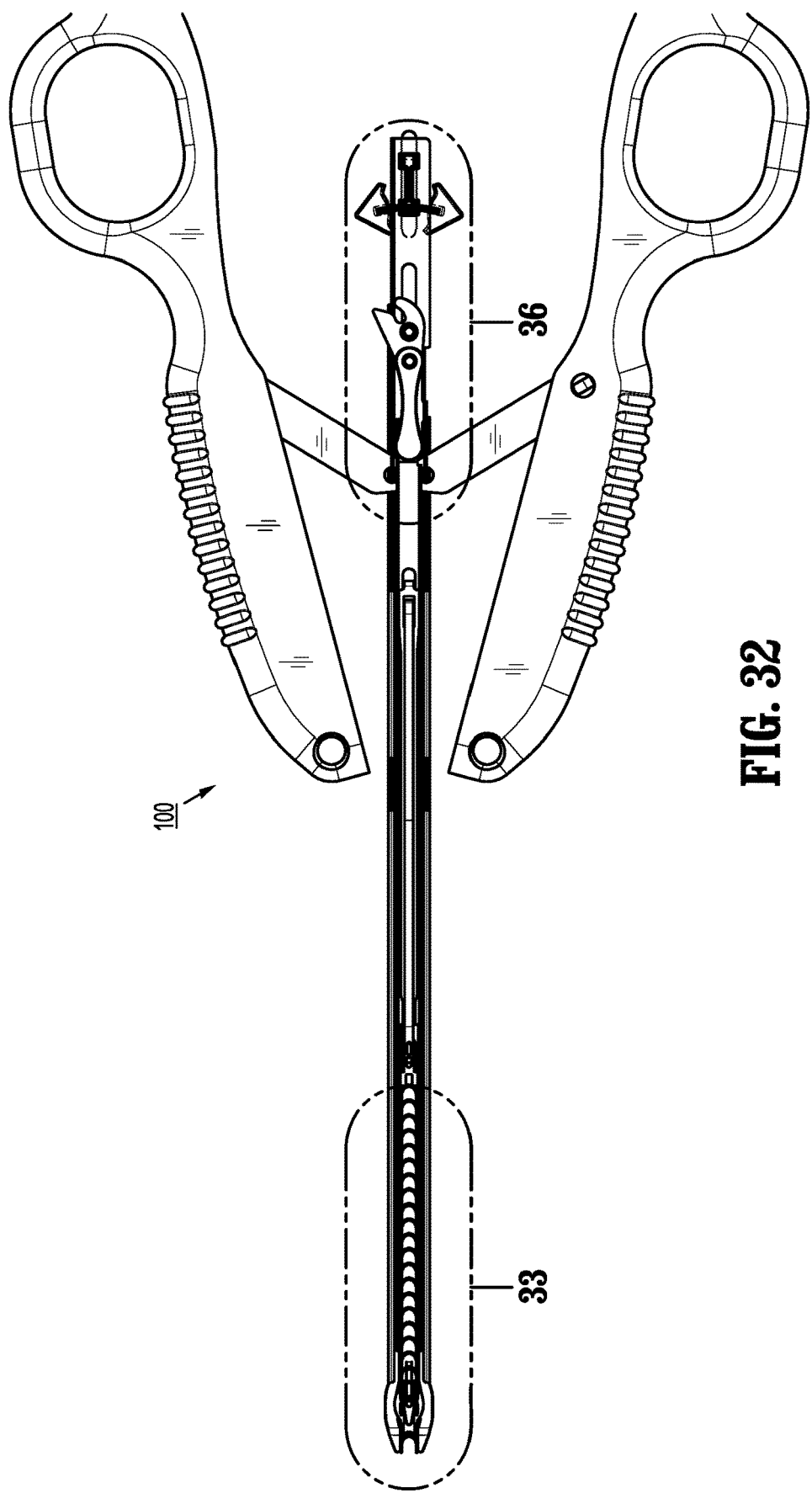
FIG. 32 is a plan view of the surgical clip applier of FIGS. 1-3 with the housing removed therefrom and illustrating the surgical clip applier in an un-actuated condition.

Body portion 176*a* and distal end 176*b* of constant force spring 176 are disposed within a channel formed in an underside of cartridge cover 130, wherein body portion 176*a* and distal end 176*b* of constant force spring 176 are interposed between cartridge cover 130 and elongate body 174*a* of clip follower 174. Distal end 176*b* of constant force spring 176 is secured to tine 170*e* of clip carrier 170, as described below. In particular, as seen in FIGS. 17 and 30, distal end 176*b* of constant force spring 176 defines an opening 176*b*$_1$ (See FIG. 5) that is slipped over a distally extending tine 170*e* of clip channel 170. In this manner, tine 170*e* of clip channel 170 prevents distal end 176*b* of constant force spring 176 from moving proximally.

Turning now momentarily to FIGS. 63-66 and 69-70, in an alternate embodiment, it is contemplated that distal end 176*b* of constant force spring 176 may be hooked onto a hook or tine 130*a* projecting distally and inwardly from an inner surface of cartridge cover 130.

Proximal coiled or spooled end 176*c* of constant force spring 176 is disposed within lower window 174*a*$_1$ and upper window 174*d*$_1$ of follower 174, wherein proximal coiled or spooled end 176*c* is interposed between tab 174*e* of follower 174 and a proximal end-most wall of follower 174. Due to a memory of constant force spring 176, proximal coiled or spooled end 176*c* thereof tends to want to roll-up along body portion 176*a*.

Constant force spring 176 is a pre-stressed flat strip of spring material which is formed into a virtually constant radius coil, wherein distal end 176*b* of constant force spring 176 is secured to clip channel 170 as described above, and wherein proximal coiled or spooled end 176*c* of constant force spring 176 is disposed within proximal end portion 174*c* of clip follower 174 as described above.

Constant force spring 176 functions to maintain a constant pressure or distal force on the stack of surgical clips "C" such that the stack of surgical clips "C" are pressed against resilient central tang 171 of clip carrier 170. In this manner, in operation, as will be discussed in greater detail below, the stack of surgical clips "C" advances distally on demand as the distal-most surgical clip "C$_d$" is advanced past resilient central tang 171 by pusher bar 160.

Figure 24:
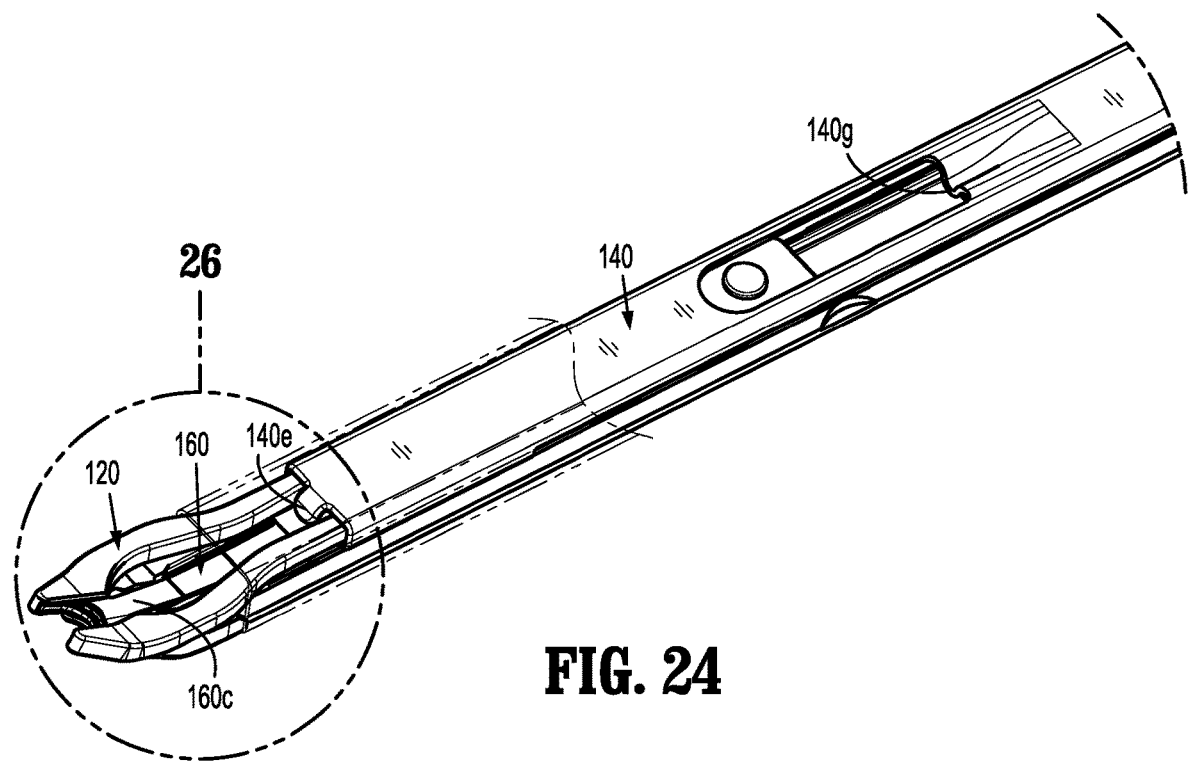
FIG. 24 is an enlarged view of the indicated area of detail of FIG. 23.
Figure 57:
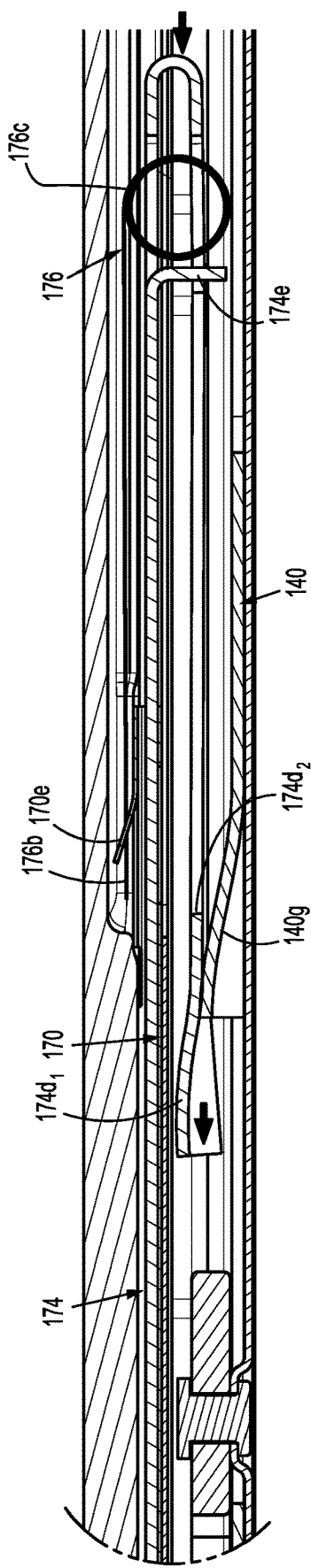
FIG. 57 is a longitudinal, cross-sectional view of the channel assembly of the surgical clip applier of FIGS. 1-3, illustrating a locking out of the surgical clip applier.
Figure 58:
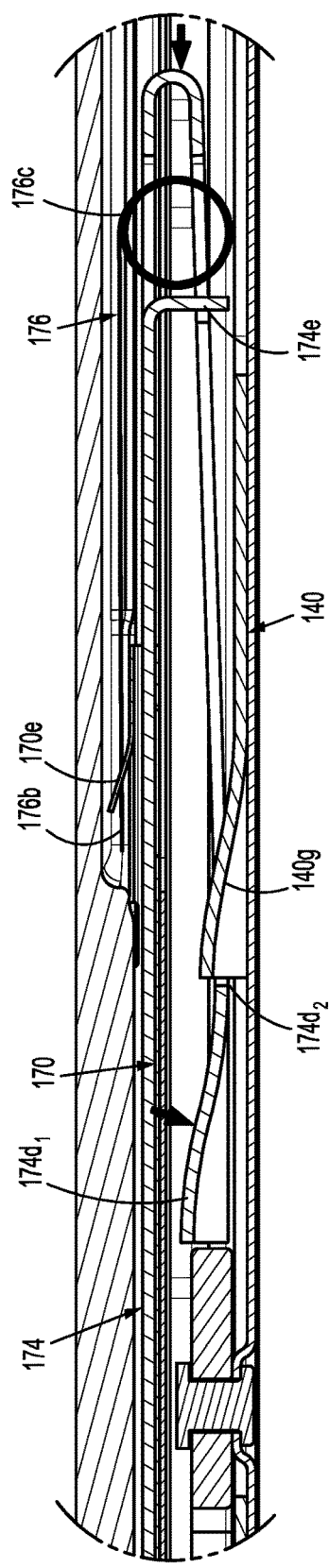
FIG. 58 is an enlarged view of the indicated area of detail of FIG. 55.
Figure 59:
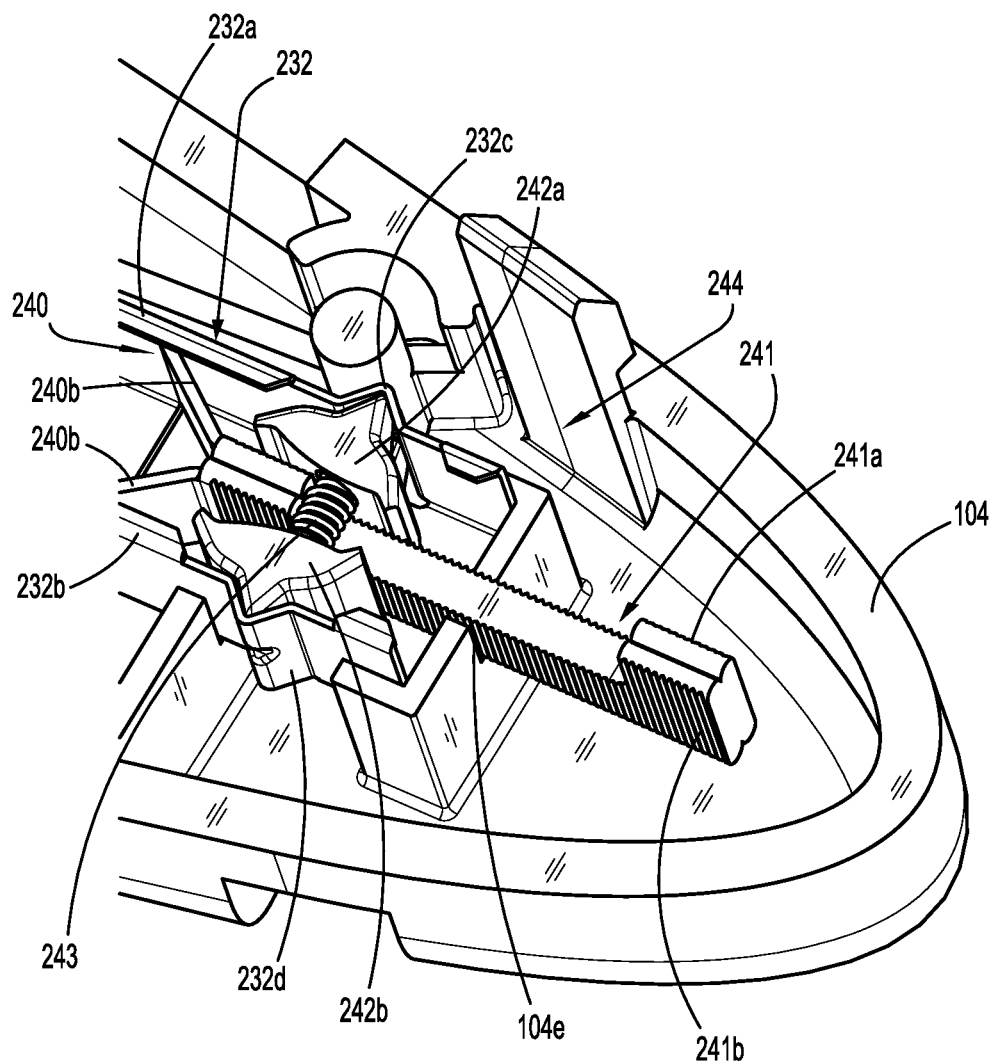
FIG. 59 is a perspective view of a rear end of a handle assembly of a surgical clip applier according to another embodiment of the present disclosure, with a housing half removed therefrom, illustrating a ratchet mechanism according to another embodiment of the present disclosure.
Figure 60:
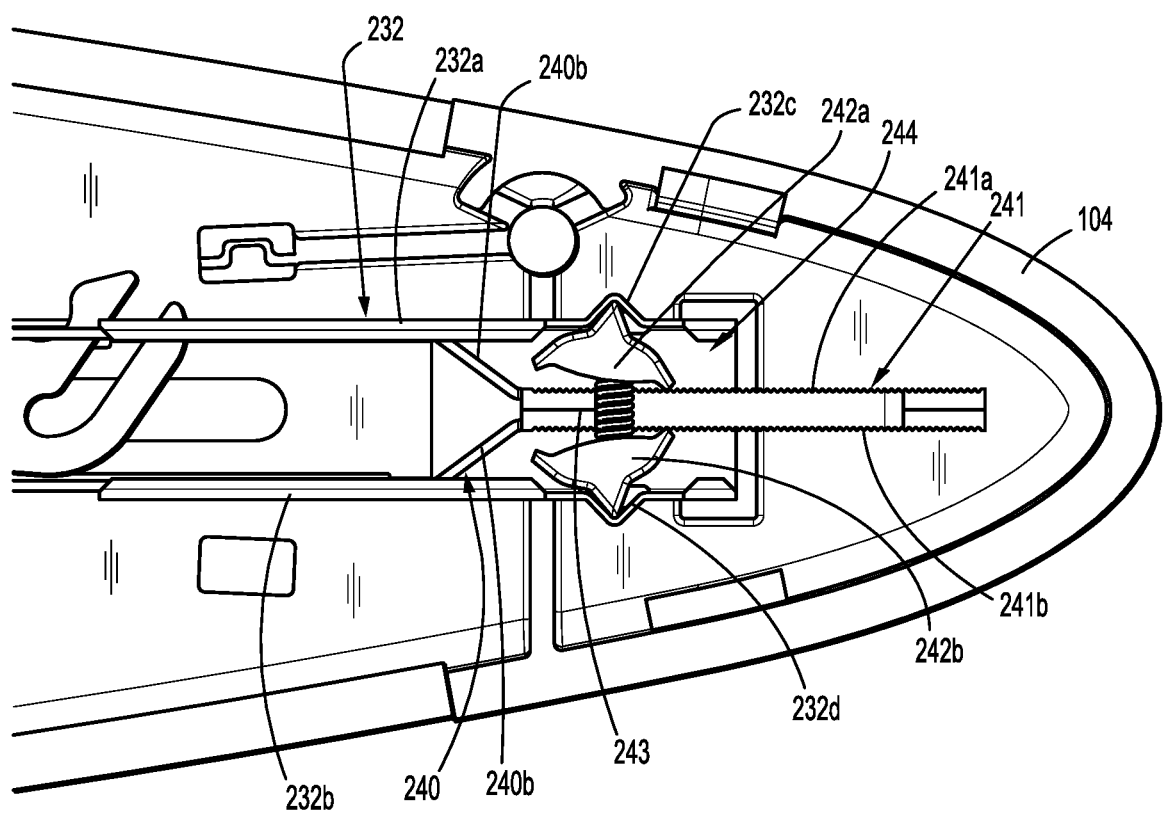
FIG. 60 is a top, plan view of the ratchet mechanism illustrated in FIG. 59.
Figure 61:
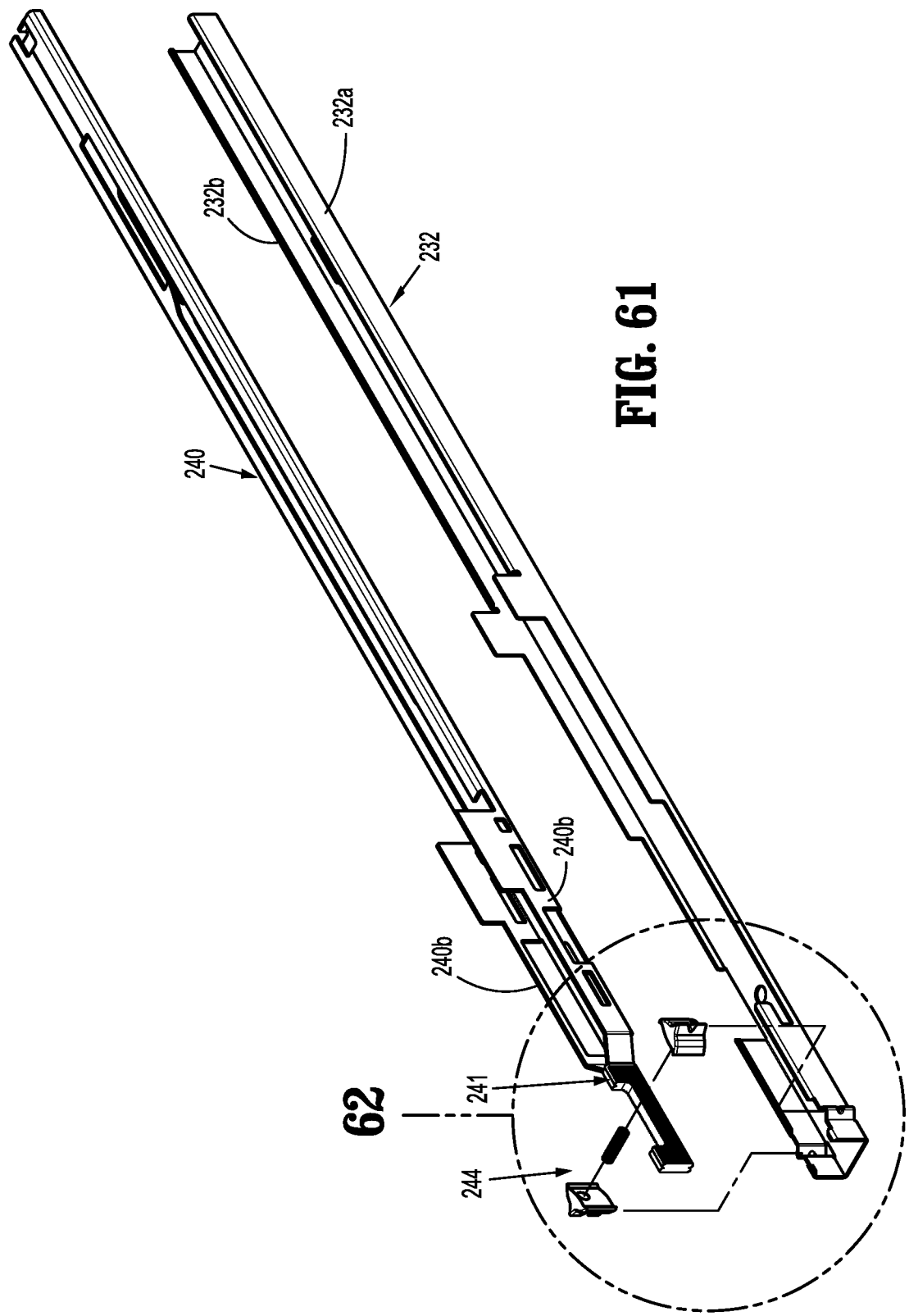
FIG. 61 is a perspective view, with parts separated, of a lower channel, a drive channel, and the ratchet mechanism of the surgical clip applier illustrated in FIGS. 59 and 60.

As seen in FIGS. 24, 57 and 58, clip applier 100 includes a lockout for preventing actuation of the pair of jaws 120 following an application of the last surgical clip of the stack of surgical clips "C". The lockout includes a stop tab or bump 174*d*$_2$ formed in distally oriented tail 174*d* of clip follower 174, and a stop tab or bump 140*g* projecting proximate a proximal end of drive channel 140. An operation of the lockout will be described in greater detail below.

With reference to FIGS. 1-58, and particularly to FIGS. 37-58, the operation of the Covidien Clip Applier 100 is provided. Prior to any initial squeezing of handles 106 of clip applier 100 (with clip applier 100 including a full stack of surgical clips "C"), as seen in FIGS. 12-36, drive channel 140 is located at a proximal-most position, pusher bar 160 is located at a distal-most position, and clip follower 174 is located at a proximal-most position. When pusher bar 160 is located at the distal-most position, pusher 160*c* thereof supports any surgical clip disposed between the pair of jaws 120.

With drive channel 140 located at a proximal-most position and pusher bar 160 located at a distal-most position, linkage mechanism 150 is situated in an un-actuated position, wherein driven link arm 154 is substantially aligned with a longitudinal axis of channel assembly 108.

Also prior to the initial squeeze, if no surgical clips "C" are present within the pair of jaws 120, a surgical clip "C" is first loaded into the pair of jaws 120 during an initial squeezing of handles 106 or a priming of clip applier 100 (to load an initial surgical clip into the pair of jaws 120).

Figure 37:
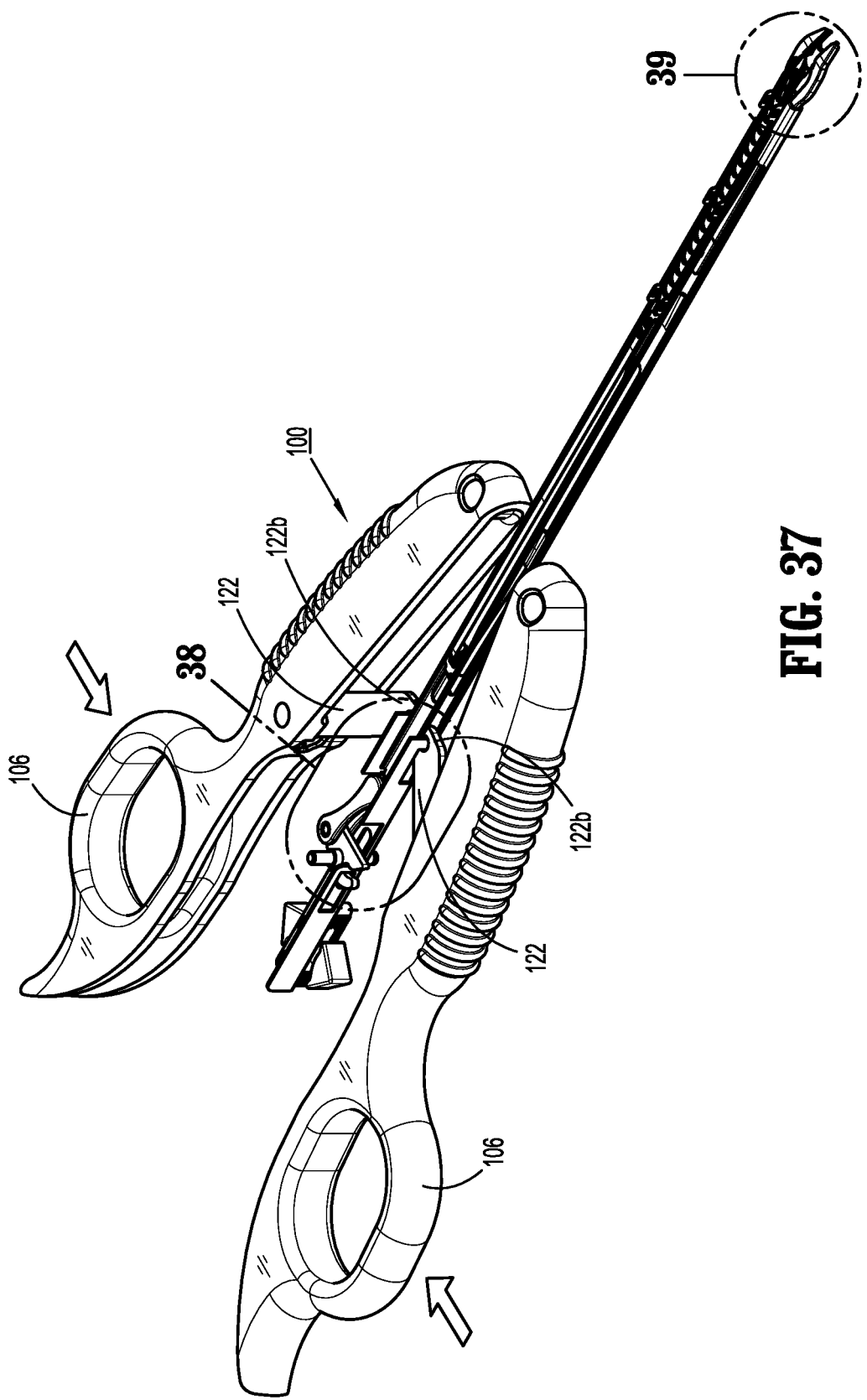
FIG. 37 is a perspective view of the surgical clip applier of FIGS. 1-3 with the housing removed therefrom and illustrating the surgical clip applier during an initial actuation thereof.
Figure 38:
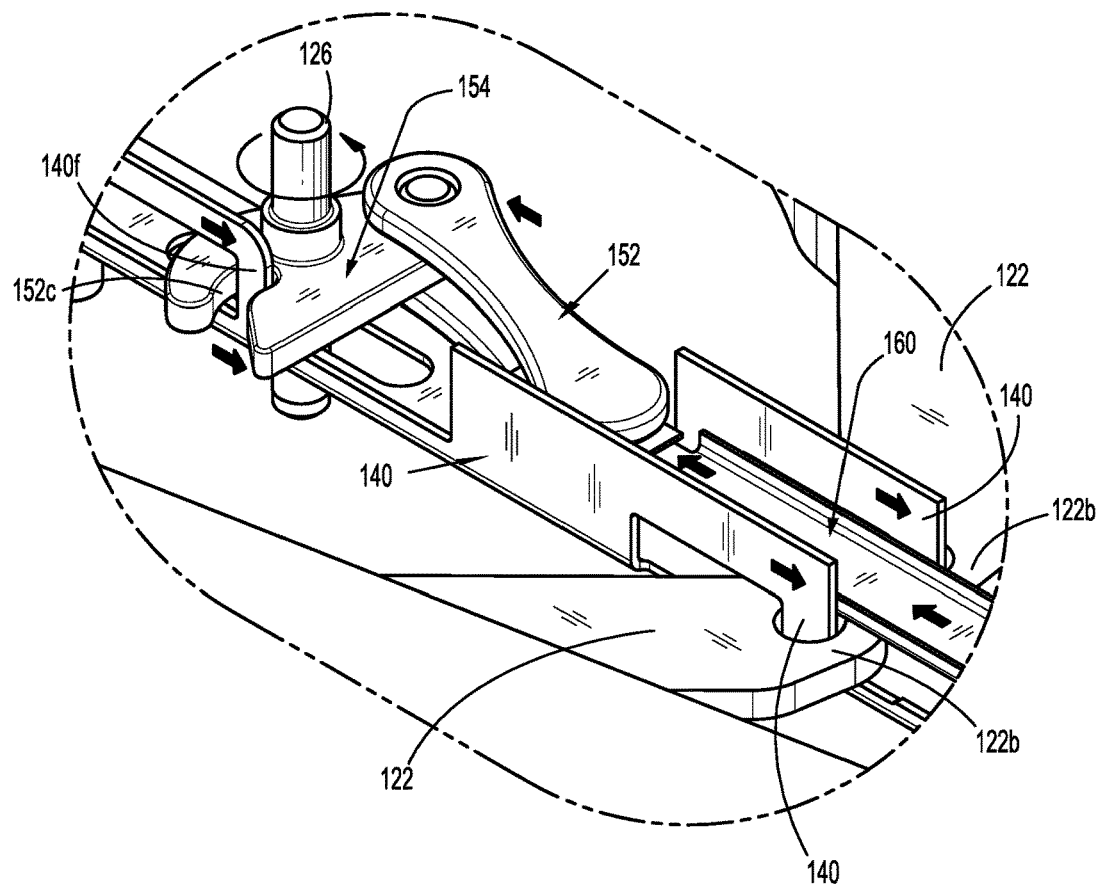
FIG. 38 is an enlarged view of the indicated area of detail of FIG. 37.

As seen in FIGS. 37-43 and particularly FIGS. 37 and 38, during a first stage of an initial squeezing of handles 106 or priming of clip applier 100, second ends 122*b* of link members 122 are caused to be moved distally relative to housing 104. As second ends 122*b* of link members 122 are moved distally, link members 122 act on drive channel 140 to transmit distal axial movement to drive channel 140.

Figure 42:
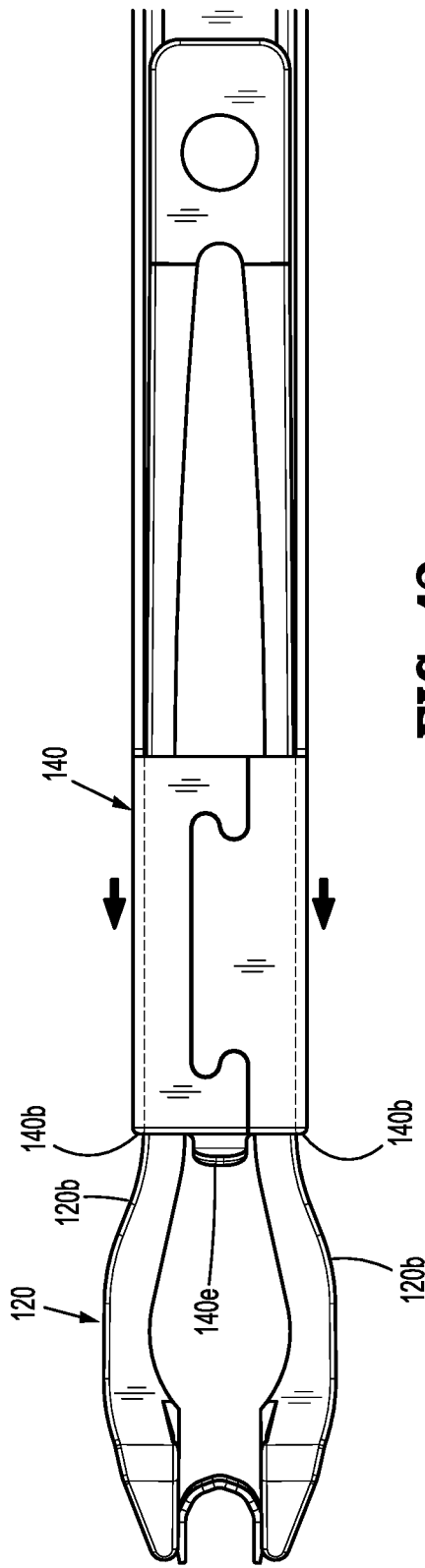
FIG. 42 is a top, plan view of the pair of jaws and the drive channel of the surgical clip applier illustrated in FIG. 37.

As seen in FIGS. 38 and 43 and FIG. 42, as drive channel 140 is moved distally, during a second stage of an initial squeeze of handles 106, following an initial dwell period, upon a further squeezing of handles 106, tab 140*f* of drive channel 140 enters into arcuate slot 152*c* of driver link arm 152 and acts on driver link arm 152 to rotate driver link arm 152 about pin 126.

As driver link arm 152 is rotated about pin 126, distal end 152*a* of driver link arm 152 acts on proximal end 154*b* of driven link arm 154 to pull driven link arm 154 in a proximal direction.

Figure 39:
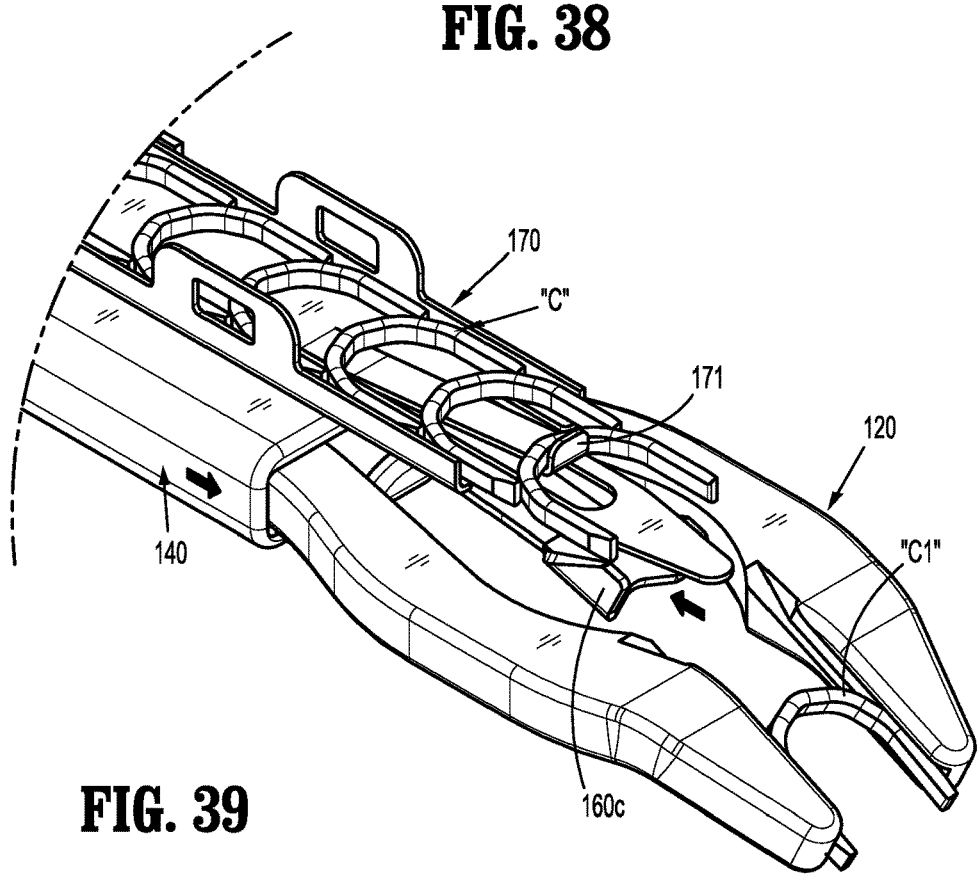
FIG. 39 is an enlarged view of the indicated area of detail of FIG. 37.
Figure 40:
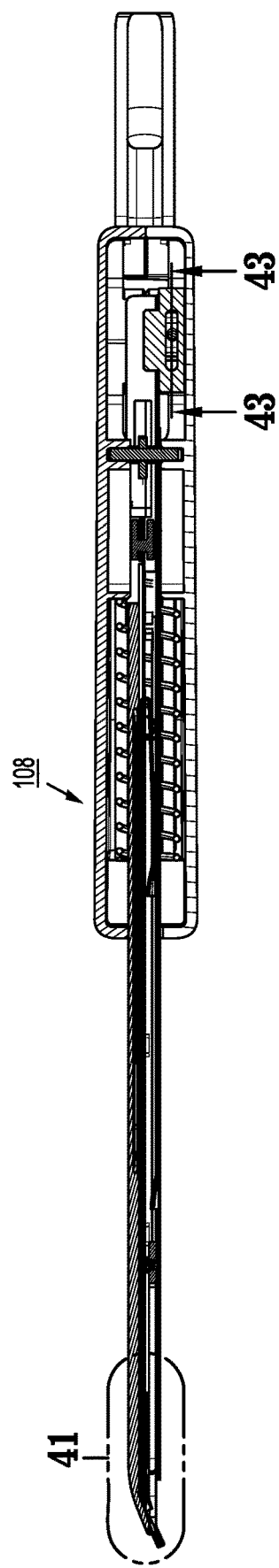
FIG. 40 is a longitudinal cross-sectional view of the surgical clip applier illustrated in FIG. 37.
Figure 41:
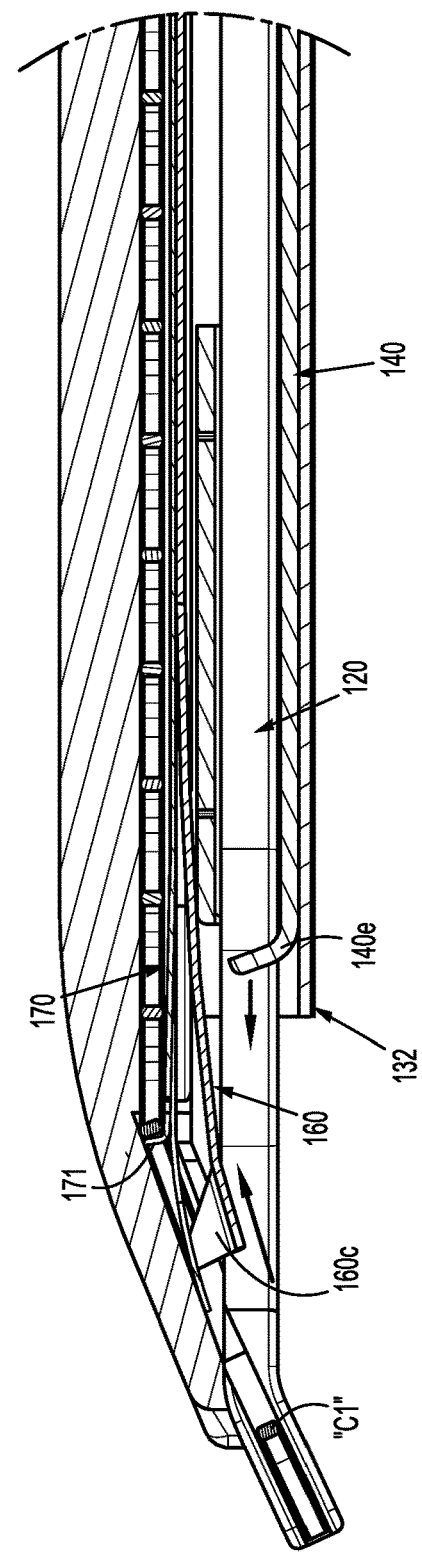
FIG. 41 is an enlarged view of the indicated area of detail of FIG. 40.

As seen in FIGS. 39-41, as driven link arm 154 is pulled in a proximal direction, distal end 154*a* of driven link arm 154 acts on pusher bar 160 to retract pusher bar 160 in a proximal direction. The relative dimensions and configurations of arcuate slot 152*c* of driver link arm 152, the radii of rotation of distal end 152*a* and proximal end 152*b* of driver link arm 152, and the relative length of driven link arm 154 determines when pusher bar 160 is retracted a sufficient amount such that pusher 160*c* is disposed proximal of a distal-most surgical clip "C1".

Following the retraction of pusher bar 160 by an amount sufficient that pusher 160*c* is disposed proximal of a distal-most surgical clip "C1", tab 140*f* of drive channel 140 exits arcuate slot 152*c* of driver link arm 152 such that proximal movement of pusher bar 160 is halted and distal movement of drive channel 140 continues.

During the initial squeeze of handles 106, pawls 142*a*, 142*b* function to create an audible click and/or a tactile vibration, thereby indicating to the user that handles 106 of surgical clip applier 100 have gone through at least a portion of a stroke. Additionally, cartridge cover 130 is fabricated from a transparent material, allowing the user to clearly see the clips "C" in the stack of clips.

As described above, the first audible/tactile indication, by pawls 142*a*, 142*b*, indicates to the user that a surgical clip "C" has been appropriately loaded.

As seen in FIG. 43, also during the first stage of the initial squeeze of handles 106, as drive channel 140 is moved in a distal direction, rack member 141 of ratchet mechanism 144 is moved distally causing teeth 141*a* thereof to move into engagement with and over or across a tooth of each pawl 142*a*, 142*b*. Once rack member 141 of ratchet mechanism 144 is moved into engagement with each pawl 142*a*, 142*b*, drive channel 140 can not return to a home or proximal-most position until rack member 141 has cleared pawls 142*a*, 142*b*.

During the second stage of the initial squeeze of handles 106, as seen in FIGS. 44-51, drive channel 140 is moved distally until a distal edge of side walls 140*b* of drive channel 140 engages against outer camming surfaces 120*b* of the pair of jaws 120 thus causing the pair of jaws 120 to approximate toward one another (and to form surgical clip "C1" interposed therebetween if a surgical clip is present).

Additionally, during the second stage of the initial squeeze of handles 106, as handles 106 are squeezed to distally advance drive channel 140, drive channel 140 and/or link members 122 act(s) on biasing member 146 to compress biasing member 146 against housing 104.

Referring to FIGS. 44-51, clip applier 100 is illustrated following a completed initial stroke or squeezing of handles 106 and during an opening of handles 106. In this condition, drive channel 140 is at a distal-most position, pusher bar 160 is at a proximal-most position, biasing member 146 is in a compressed condition, and each pawl 142a, 142b is located proximal of rack member 141.

In use, handles 106 may be opened by hand, or the closure force tending to maintain handles 106 closed is removed, whereby the compressed biasing member 146 may expand. As compressed biasing member 146 expands, biasing member 146 acts on link arms 122 and/or drive channel 140 to assist in the opening of handles 106 and the return of clip applier 100 to an open or initial condition.

Figure 53:
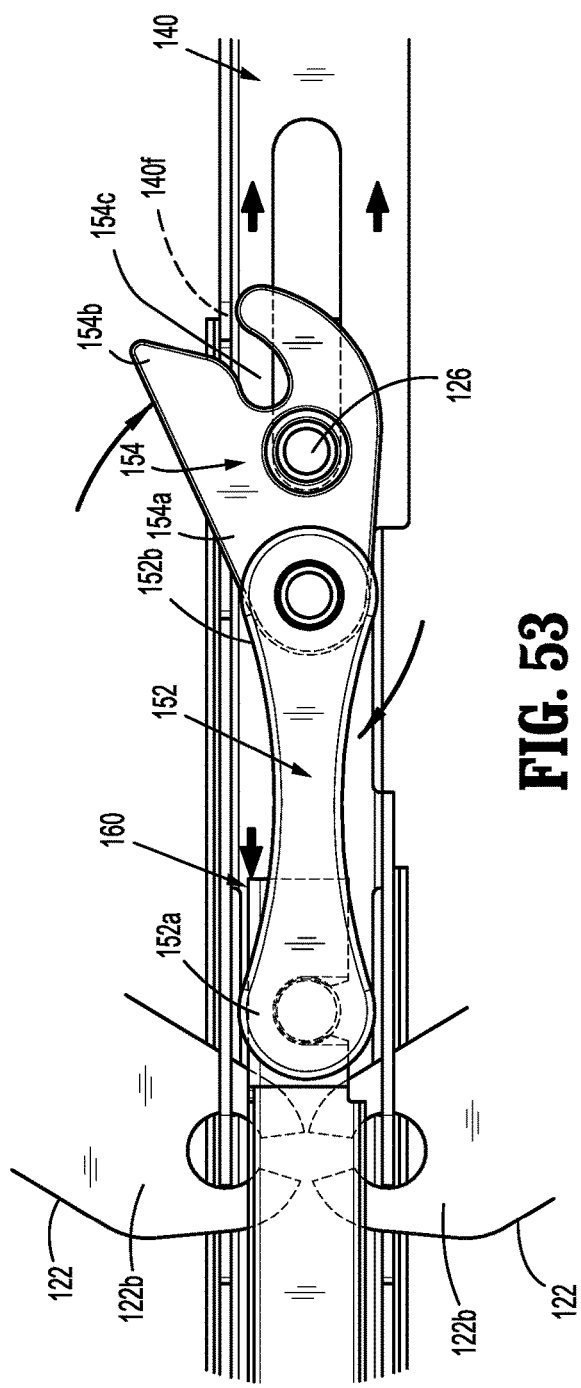
FIG. 53 is a top, plan view of the linkage mechanism illustrated during an opening of the surgical clip applier of FIGS. 1-3.
Figure 54:
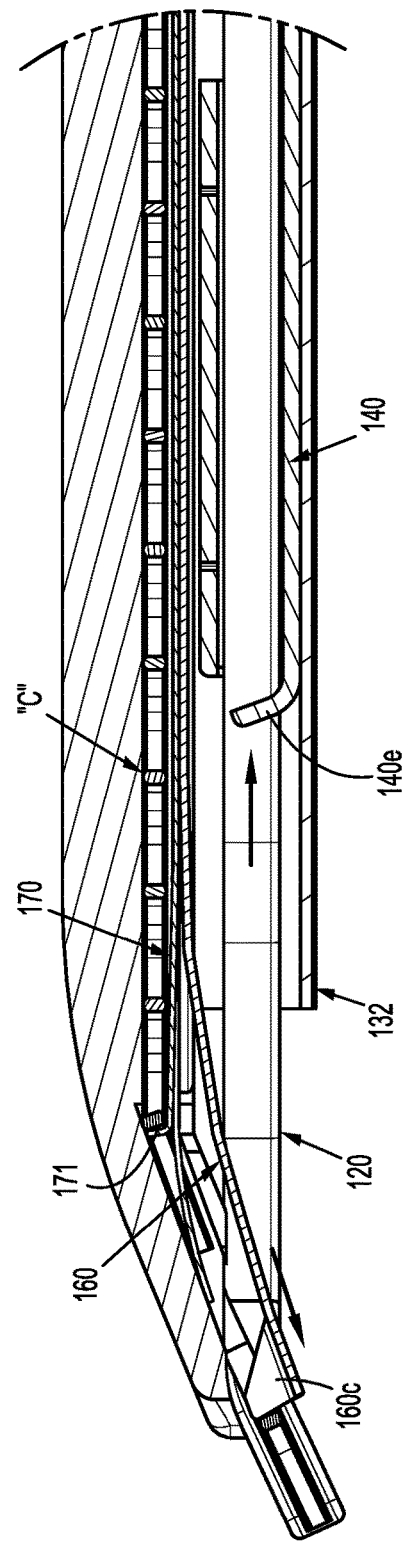
FIG. 54 is a longitudinal, cross-sectional view of the distal end of the surgical clip applier of FIGS. 1-3, illustrated during an opening of the surgical clip applier.

As seen in FIGS. 53-54, during an opening of handles 106, second ends 122b of link members 122 are caused to be moved proximally relative to housing 104. As second ends 122b of link members 122 are moved proximally, link members 122 act on drive channel 140 to transmit proximal axial movement to drive channel 140.

As drive channel 140 is moved proximally, following an initial dwell period, tab 140f of drive channel 140 re-enters into arcuate slot 152c of driver link arm 152 and acts on driver link arm 152 to rotate driver link arm 152 about pin 126 in a reverse direction.

As driver link arm 152 is rotated about pin 126 (in a reverse direction), distal end 152a of driver link arm 152 acts on proximal end 154b of driven link arm 154 to push driven link arm 154 in a distal direction.

As driven link arm 154 is pushed in a distal direction, distal end 154a of driven link arm 154 acts on pusher bar 160 to advance pusher bar 160 in a distal direction, as seen in FIGS. 53 and 54. The relative dimensions and configurations of arcuate slot 152c of driver link arm 152, the radii of rotation of distal end 152a and proximal end 152b of driver link arm 152, and the relative length of driven link arm 154 determines when pusher bar 160 is advanced a sufficient amount such that pusher 160c of pusher bar 160 loads a distal-most surgical clip "C1" of the stack of surgical clips "C" into the pair of jaws 120.

In particular, as pusher bar 160 is advanced in a distal direction, pusher 160c thereof engages a backspan of distal-most clip "C1" and begins to move or urge distal-most clip "C1" distally out of clip carrier 170 and into the pair of jaws 120. As distal-most clip "C1" is moved distally, central tang 171 of clip carrier 170 is momentarily deflected or cammed out of engagement with distal-most clip "C1" and returned to its un-deflected or un-cammed state to capture a subsequent surgical clip of the stack of surgical clips "C". During the opening of handles 106, pusher bar 160 is advanced an amount sufficient to place distal-most surgical clip "C1" in channels 120a of pair of jaws 120.

As pusher 160c of pusher bar 160 advanced distal-most surgical clip "C1" into the pair of jaws 120, the remaining stack of surgical clips "C" is advanced distally due to an advancement force acting on the stack of surgical clips "C" by clip follower 174. In particular, with the removal of the distal-most surgical clip "C1", proximal coiled end 176c of constant force spring 176 continues to coil up onto itself, thus shortening a length of body portion 176a since distal end 176b of constant force spring 176 is anchored to clip carrier, as described above.

As proximal coiled end 176c of constant force spring 176 coils up onto itself, proximal coiled end 176c acts on tabs 174e of clip follower 174 to exert a distal force on clip follower 174 and distally advance clip follower 174. Clip follower 174 is advanced distally until the stack of surgical clips "C" is stopped by central tang 171 of clip carrier 170.

Following the return of pusher bar 160 to the distal-most position, tab 140f of drive channel 140 exits arcuate slot 152c of driver link arm 152 such that distal movement of pusher bar 160 is halted and proximal movement of drive channel 140 continues.

With pusher bar 160 at the distal-most position, pusher 160c of pusher bar 160 remains against the backspan of the distal-most surgical clip "C1" that was loaded into the pair of jaws 120. In this manner, when the pair of jaws 120 are advanced over a target vessel, pusher 160c of pusher bar 160 supports the backspan of the distal-most surgical clip "C1" to inhibit the distal-most surgical clip "C1" from backing out of the pair of jaws 120.

During the complete opening of handles 106, the proximal-most positioning of drive channel 140 causes pawls 142a, 142b to flip and snap, creating an audible click and/or a tactile vibration, thereby indicating to the user that handles 106 of surgical clip applier 100 have completely opened and that surgical clip applier 100 has undergone a complete cycle.

As seen in FIG. 46, also during the opening of handles 106, as drive channel 140 is moved in a proximal direction, rack member 141 of ratchet mechanism 144 is moved proximally causing teeth 141a thereof to move back into engagement with and over or across a tooth of each pawl 142a, 142b. Once rack member 141 of ratchet mechanism 144 is moved back into engagement with each pawl 142a, 142b, drive channel 140 can not be re-advanced distally to an advanced or distal-most position until rack member 141 has re-cleared pawls 142a, 142b.

Figure 26:
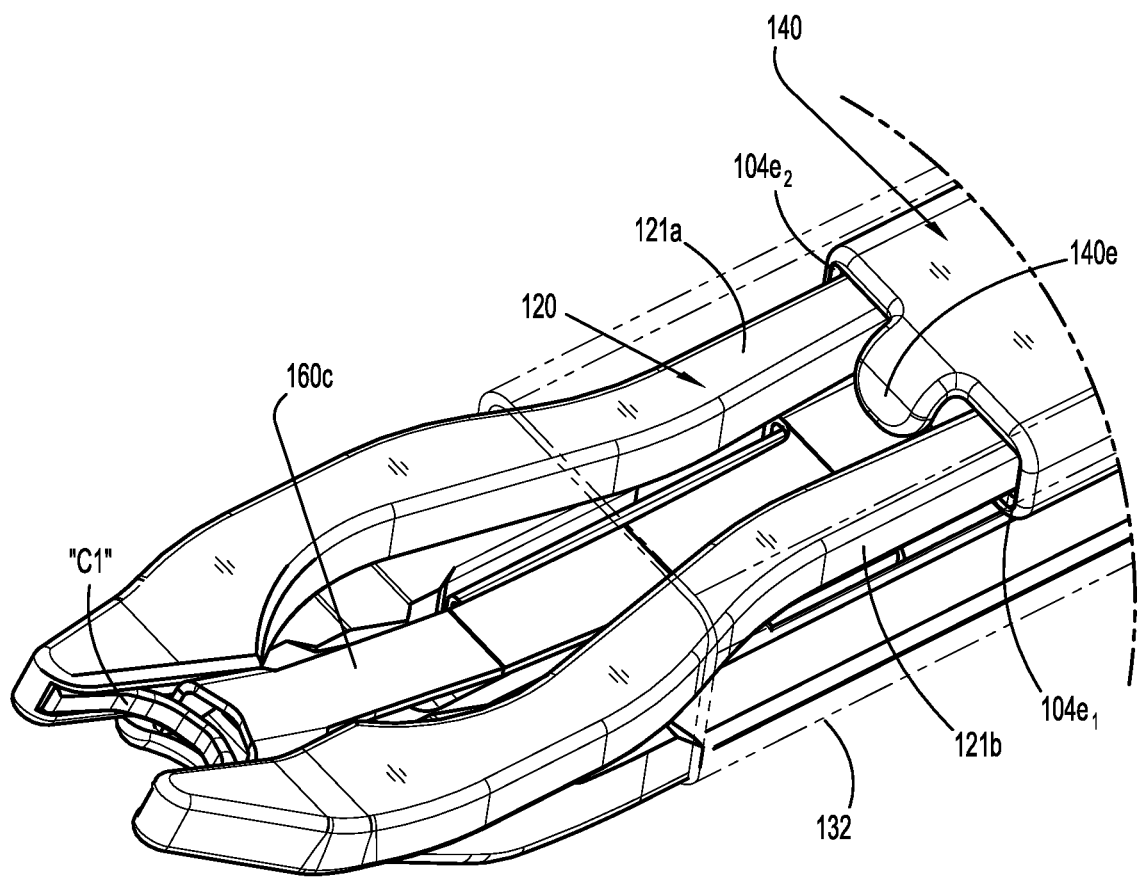
FIG. 26 is an enlarged view of the indicated area of detail of FIG. 24.
Figure 27:
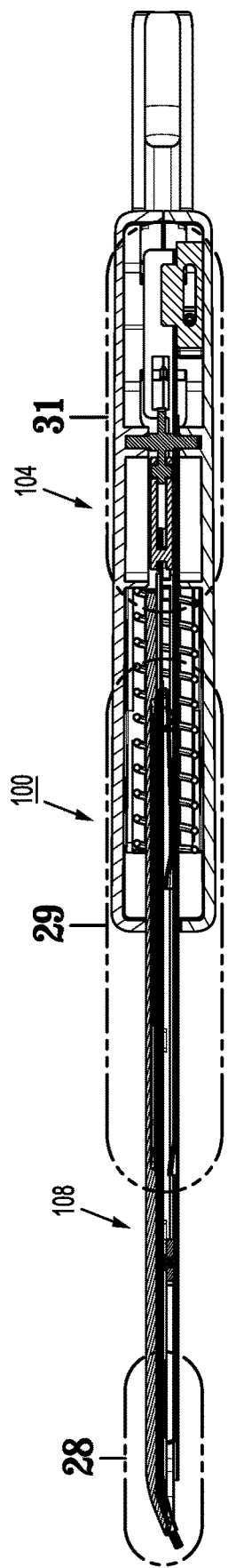
FIG. 27 is a longitudinal cross-sectional view of the surgical clip applier illustrated in FIG. 23.
Figure 28:
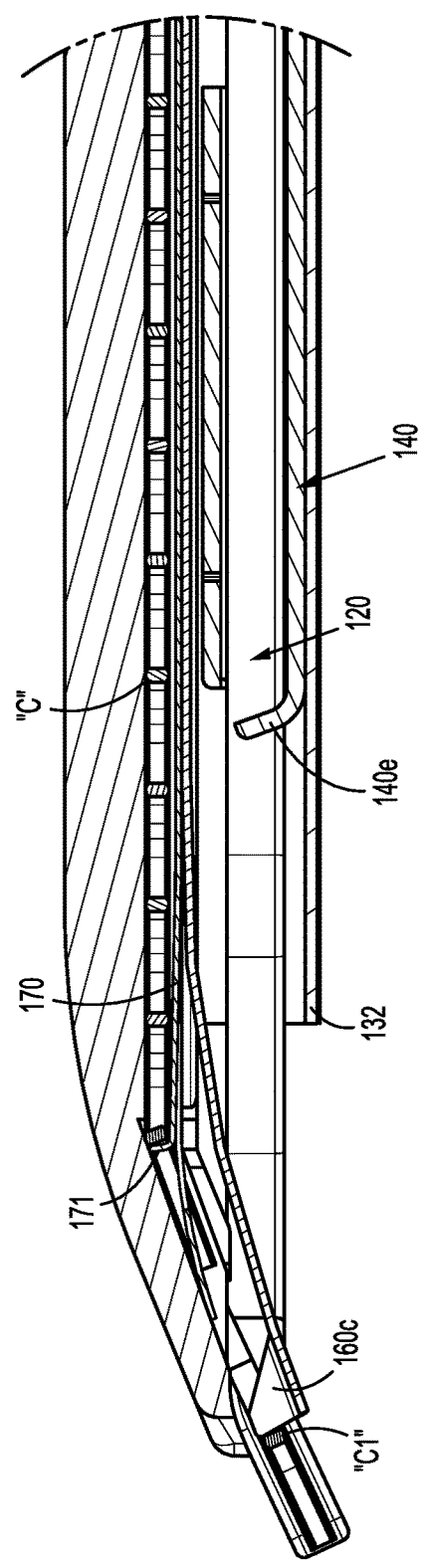
FIG. 28 is an enlarged view of the indicated area of detail of FIG. 27.
Figure 29:
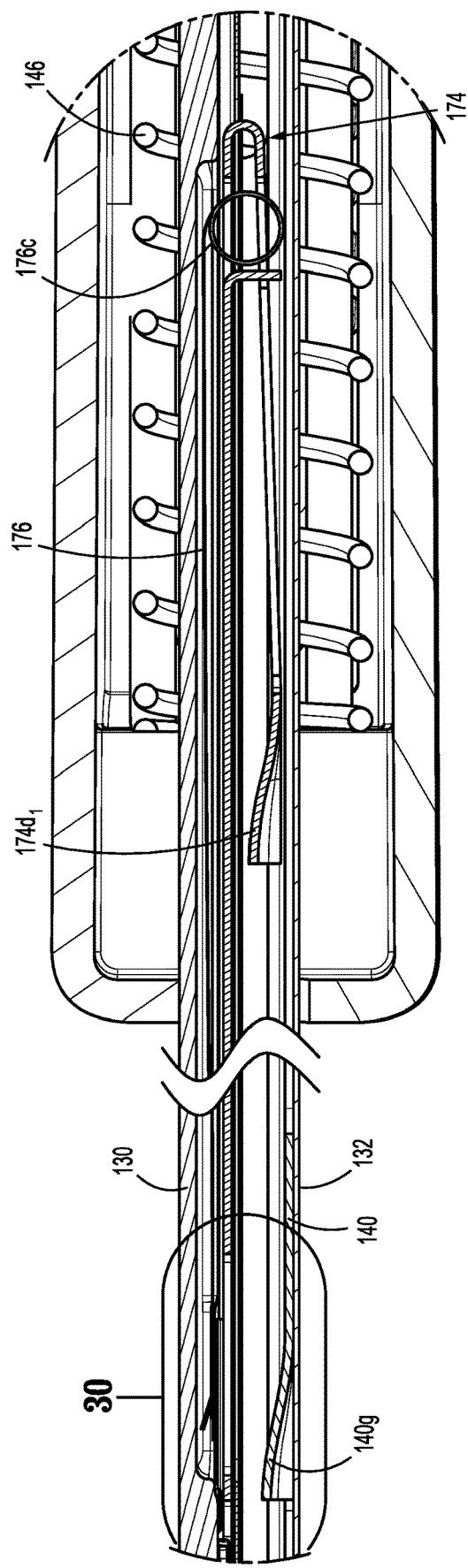
FIG. 29 is an enlarged view of the indicated area of detail of FIG. 27.

During the opening of handles 106, as seen in FIG. 26, drive channel 140 is moved proximally such that and until tongue 140e of drive channel 140 engages against inner camming surfaces 120c of the pair of jaws 120 thus assisting and/or causing the pair of jaws 120 to spread apart from one another to a fully open condition (in the event that the pair of jaws 120 were being held in an approximated condition by some external pressure or force).

Figure 52:
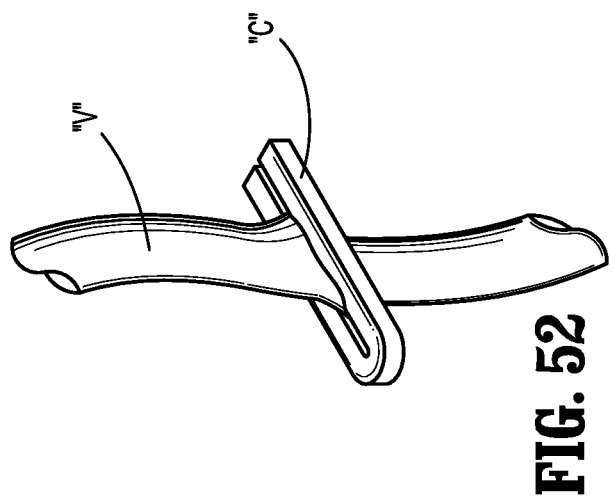
FIG. 52 is a perspective view of a body vessel including a clip of the surgical clip applier, shown applied thereto.

Following an initial priming of clip applier 100, any further squeezing of handles 106 will result in the firing of clip applier 100 to apply a surgical clip "C1" onto a vessel "V" or any other biological tissue, as seen in FIG. 52.

During a re-squeezing of handles 106 as drive channel 140 is moved distally and pusher bar 160 is moved proximally, as described above, with surgical clip "C1" loaded into the pair of jaws 120, as distal edge of side walls 140b of drive channel 140 engages against outer camming surfaces 120b of the pair of jaws 120, the pair of jaws 120 are approximated toward one another to form surgical clip "C1".

As seen in FIG. 52, surgical clip "C1" may be formed or crimped onto a vessel "V" or any other biological tissue. In certain instances, the surgeon may decide or need to fire a surgical clip "C1" onto a suture in lieu of typing a knot in the suture.

Turning now to FIGS. 55-56 and FIGS. 57-58, a distal end of clip applier 100 is illustrated following a complete stroke or squeezing of handles 106 and after a final surgical clip has been urged from clip carrier 170 and loaded into the pair of jaws 120, as described above. Following loading of the final surgical clip into the pair of jaws 120, clip follower 174 is advanced to a distal-most position by constant force spring 176, as described above.

With the last clip loaded into the pair of jaws 120, as clip applier 100 is fired once again to fire the last clip, by squeezing handles 106, pusher bar 160 is moved in the proximal direction (as described above) such that pusher 160c (see FIG. 6) cams over and proximal of distal end portion 174b (see FIG. 7) of clip follower 174. Then, as handles 106 are opened, pusher bar 160 is moved in the distal direction (as described above). As pusher bar 160 is moved in the distal direction, pusher 160c acts on distal end portion 174b of clip follower 174 to urge clip follower 174 distally until (1) distal end portion 174b of clip follower 174 is disposed between the pair of jaws 120, and (2) front edge $174d_3$ of lower window $174d_1$ (see FIG. 7) of tail 174d of clip follower 174 is disposed distally of stop tab 140g of drive channel 140.

At this point, there is no clip in the pair of jaws 120, and the lockout tail 174d on clip follower 174 is engaged with stop tab 140g on drive channel 140. As such, if the user attempts to fire clip applier 100 at this point, drive channel 140 drives lockout tail 174d of clip follower 174 against the pair of jaws 120, and together with distal end portion 174b of clip follower 174 being disposed between the pair of jaws 120, clip applier 100 is incapable of having the pair of jaws 120 closed.

Additionally, with stop tab 140g of drive channel 140 disposed proximally of front edge $174d_3$ of lower window $174d_1$ of tail 174d of clip follower 174, as seen in FIG. 58, any attempt to re-actuate clip applier 100, whereby drive channel 140 is distally advanced, will result in stop tab 140g of drive channel 140 abutting against front edge $174d_3$ of lower window $174d_1$ of tail 174d of clip follower 174 thereby preventing distal advancement of drive channel 140.

Turning now to FIGS. 59-62, a lower channel according to another embodiment of the present disclosure, is generally designated as 232. Lower channel 232 is substantially similar to lower channel 132 and thus will only be discussed in detail herein to the extent necessary to describe differences in structure and operation thereof. As seen in FIGS. 59-62, lower channel 232 includes a pair of opposed, upstanding, proximal side walls 232a, 232b. Each side wall 232a, 232b defines a substantially V-shaped channel 232c, 232d, wherein each V-shaped channel 232c, 232d extends in a direction orthogonal to a longitudinal axis of lower channel 232. A respective rib 232e, 232f extends into each V-shaped channel 232c, 232d.

With continued reference to FIGS. 59-62, a drive channel according to another embodiment of the present disclosure, is generally designated as 240. Drive channel 240 is substantially similar to drive channel 140 and thus will only be discussed in detail herein to the extent necessary to describe differences in structure and operation thereof. As seen in FIGS. 59-62, opposed side walls 240b thereof join together at a proximal end of drive channel 240 to form a tail or ratchet rack member 241. Ratchet rack member 241 includes a first set of teeth 241a, on a first side thereof, configured and adapted to engage with a first ratchet pawl 242a, and a second set of teeth 241b, on a second side thereof, configured and adapted to engage a second ratchet pawl 242b.

Ratchet rack member 241 of drive channel 240 extends between side walls 232a, 232b of lower channel 230 and through a slot 104e formed in housing 104. Additionally, first ratchet pawl 242a is interposed between side wall 232a of lower channel 230 and ratchet rack member 241 of drive channel 240, and second ratchet pawl 242b is interposed between side wall 232b of lower channel 230 and ratchet rack member 241 of drive channel 240.

Rack member 241 and pawls 242a, 242b define a ratchet mechanism 244. In use, as drive channel 240 is moved axially, rack member 241 is caused to be moved relative to first and second ratchet pawl 242a, 242b. In so doing, the series of rack teeth 241a, 241b have a length which allows respective pawls 242a, 242b to reverse and advance back over rack member 241 when rack member 241 changes between proximal and distal movement as drive channel 240 reaches a proximal-most or distal-most position.

Each pawl 242a, 242b is pivotally supported in lower channel 230 at a location wherein each pawl 242a, 242b is in substantial operative engagement with respective rack teeth 241a, 241b of rack member 241. Pawls 242a, 242b are engageable with rack member 241 to restrict longitudinal movement of rack member 241 and, in turn, drive channel 240.

Each pawl 242a, 242b has a substantially triangular profile, wherein a remote corner $242a_1$, $242b_1$ of each pawl 242a, 242b extends away from rack member 241 and is situated within an internal corner of respective V-shaped channel 232c, 232d of lower channel 230. The interface of the remote corner $242a_1$, $242b_1$ of each pawl 242a, 242b and respective V-shaped channel 232c, 232d of lower channel 230 defines a pivot point for pawls 242a, 242b. A degree of pivoting of each pawl 242a, 242b is limited by the relative shape and dimension of pawls 242a, 242b and the relative angular orientation of respective V-shaped channel 232c, 232d of lower channel 230.

Figure 62:
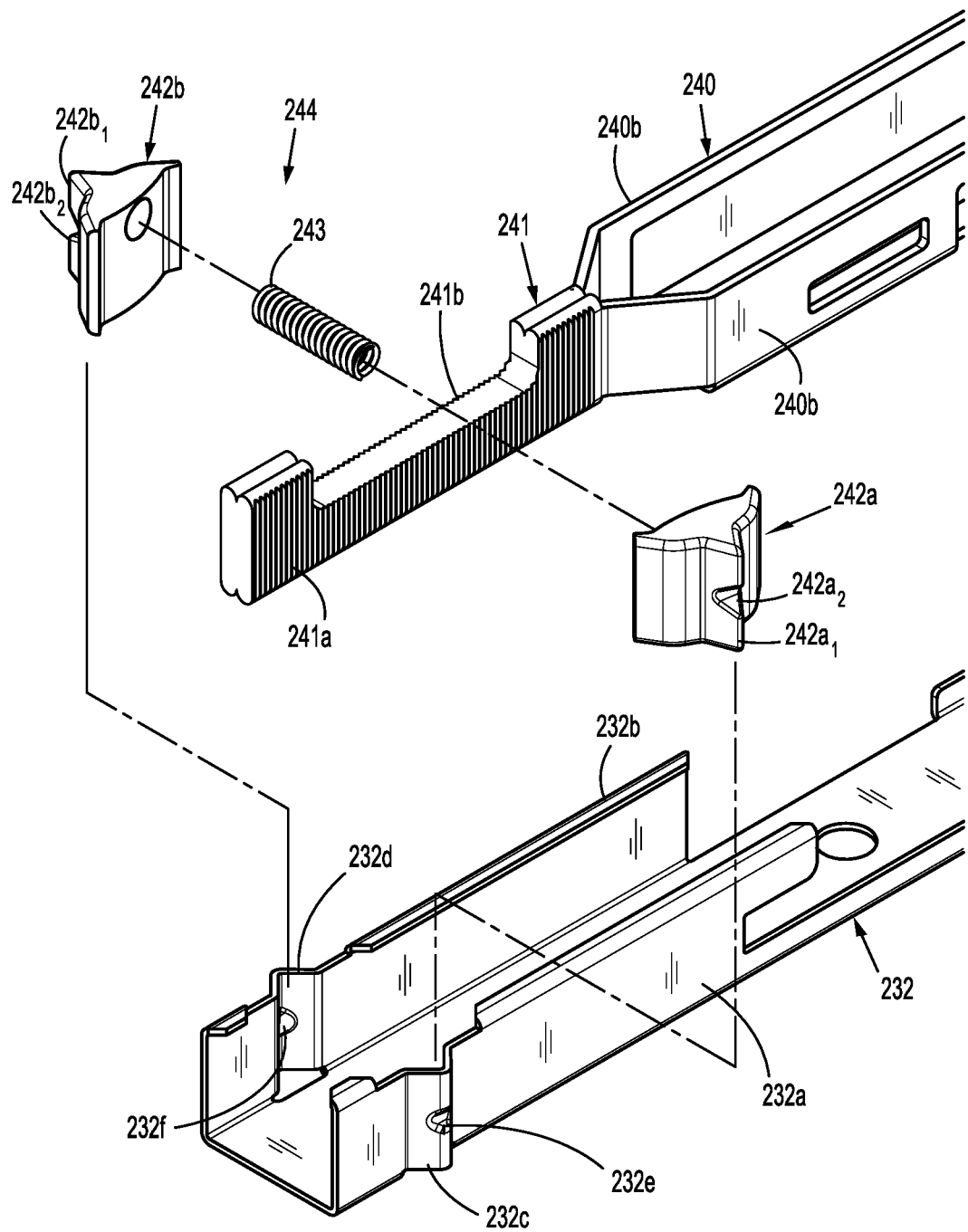
FIG. 62 is an enlarged view of the indicated area of detail of FIG. 61.
Figure 63:
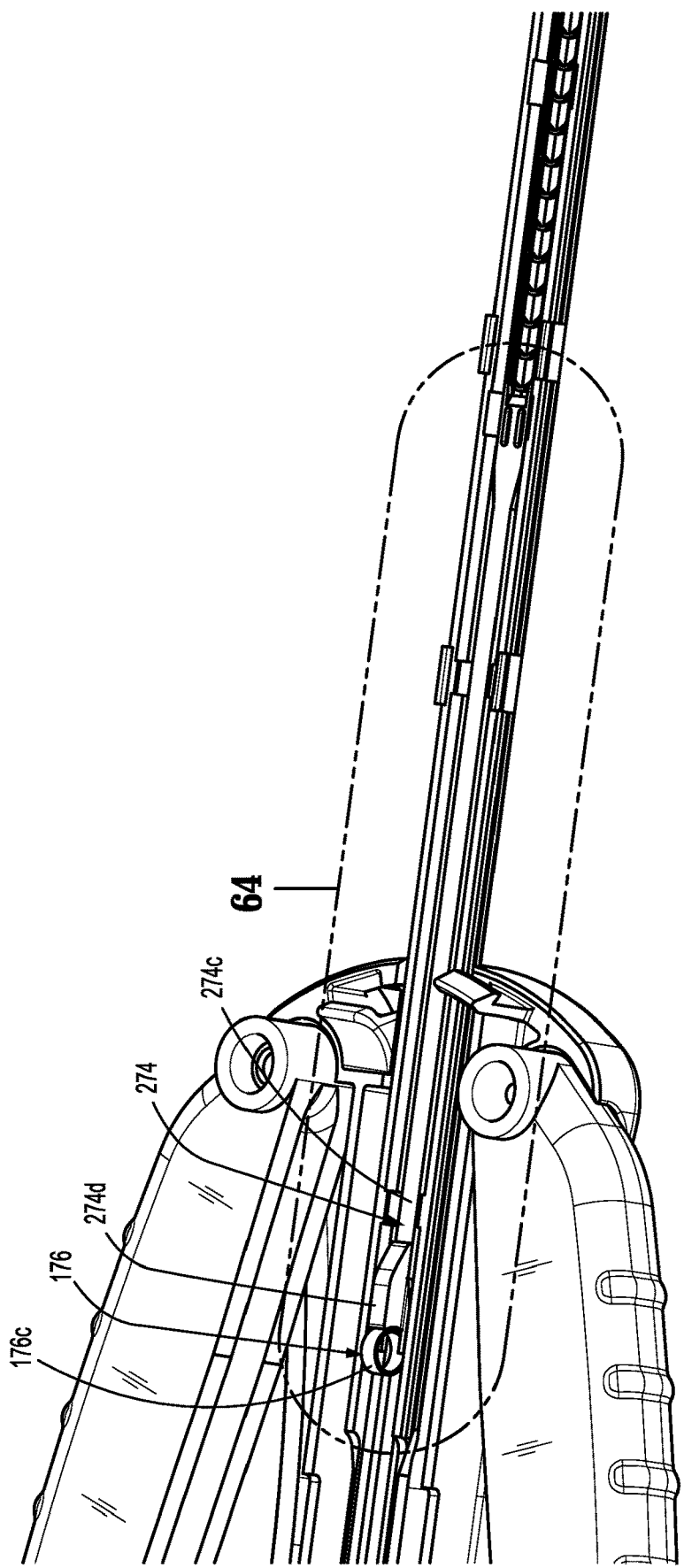
FIG. 63 is a top, perspective view of a surgical clip applier, with a cover and a housing half-section removed therefrom, illustrating a clip follower according to another embodiment of the present disclosure.
Figure 64:
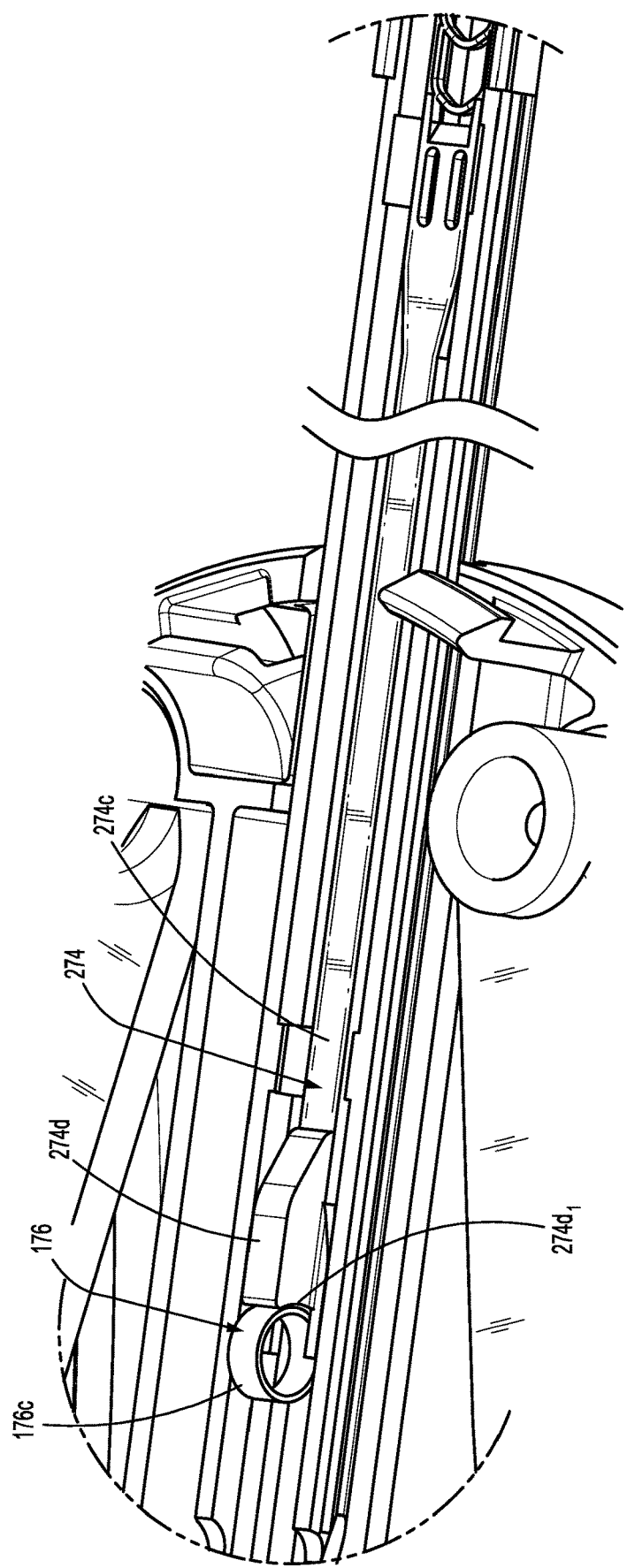
FIG. 64 is an enlarged view of the indicated area of detail of FIG. 63.
Figure 68:
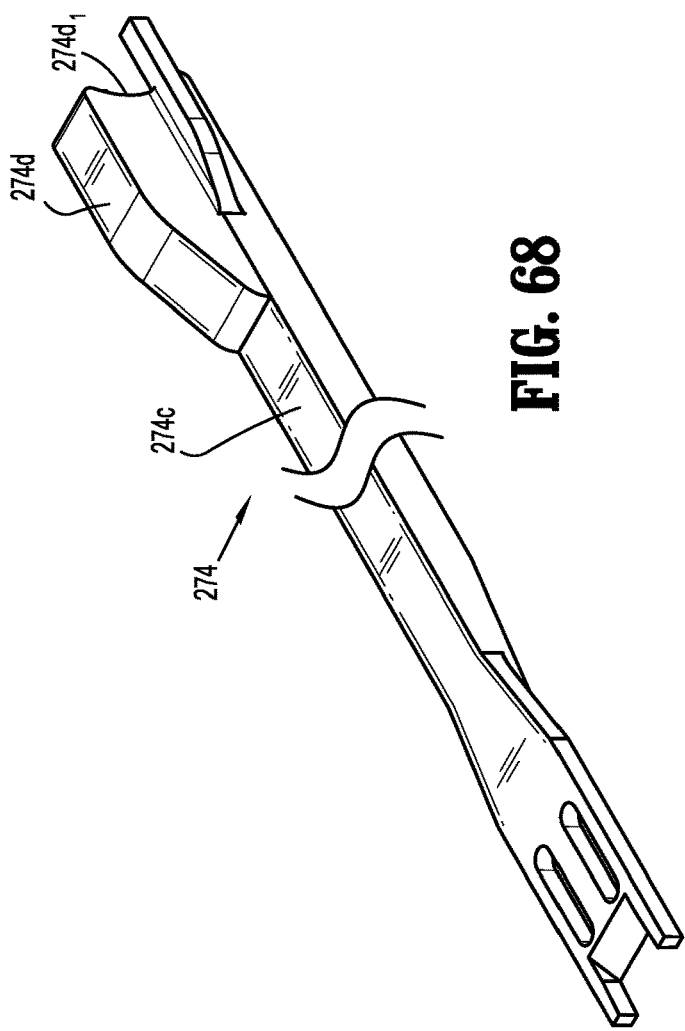
FIG. 68 is a front, top perspective view of the clip follower of FIGS. 63-65.
Figure 67:
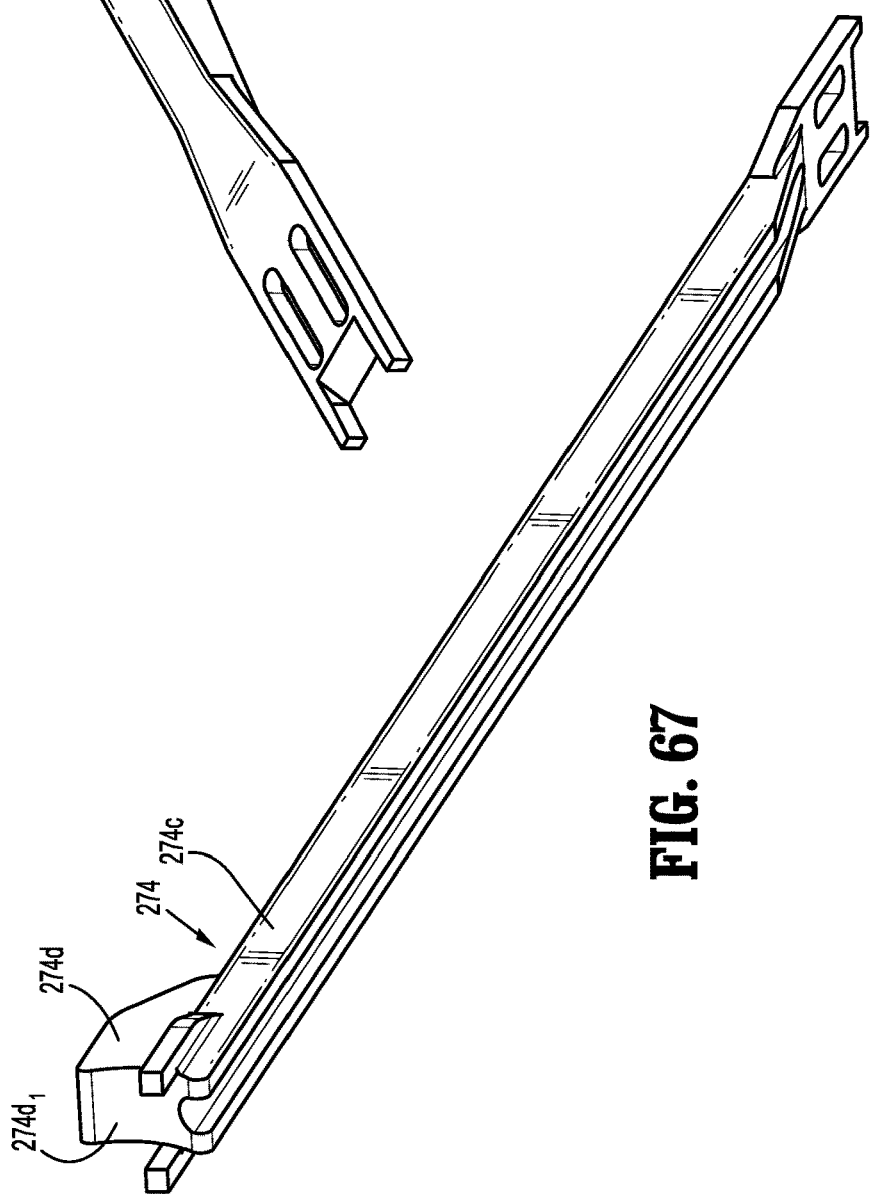
FIG. 67 is a rear, bottom perspective view of the clip follower of FIGS. 63-65.
Figure 69:
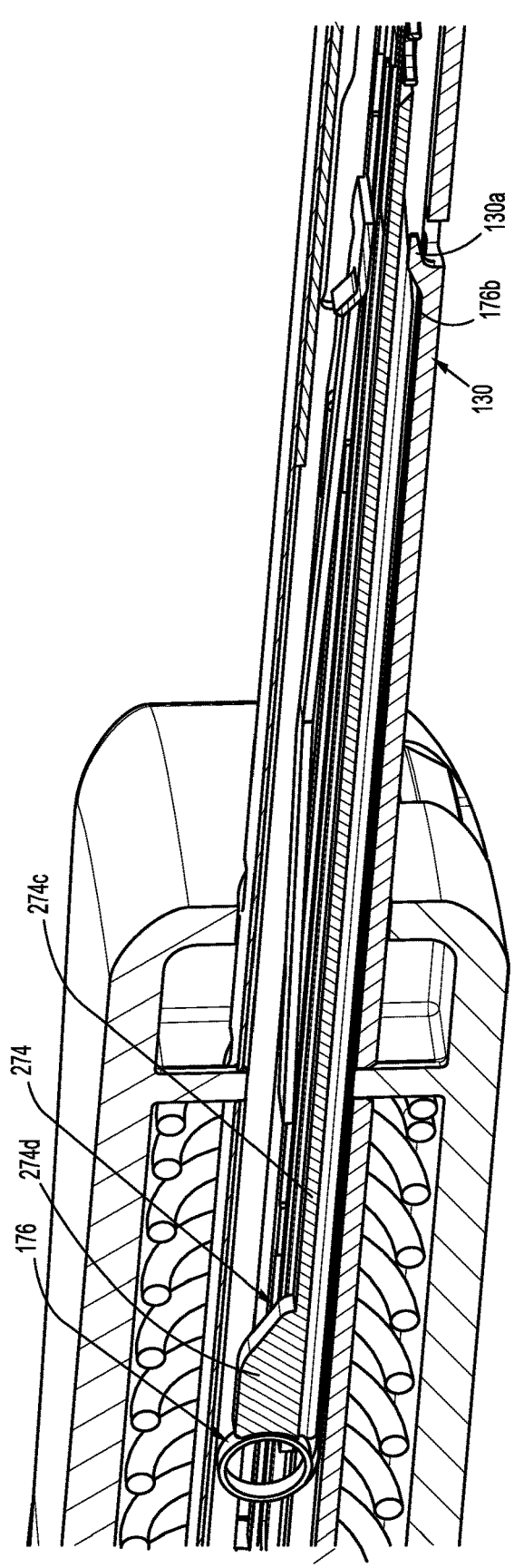
FIG. 69 is a perspective, longitudinal cross-sectional view of the clip applier illustrated in FIGS. 63-66.
Figure 70:
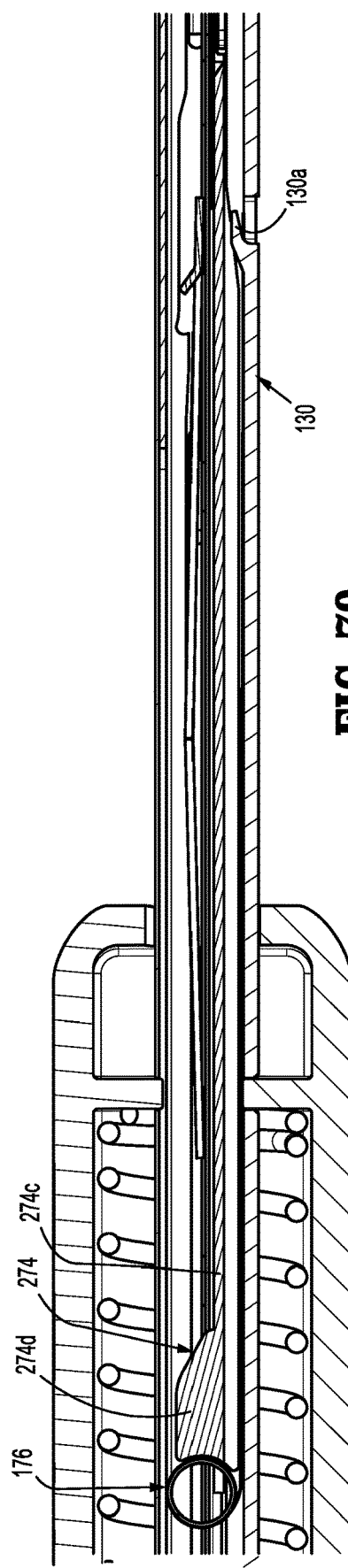
FIG. 70 is an elevational, longitudinal cross-sectional view of the clip applier illustrated in FIGS. 63-66.

Additionally, as seen in FIG. 62, remote corner $242a_1$, $242b_1$ of each pawl 242a, 242b defines a respective notch $242a_2$, $242b_2$ formed therein. Notches $242a_2$, $242b_2$ of each pawl 242a, 242b are configured to receive respective ribs 232e, 232f of V-shaped channels 232c, 232d of lower channel 230 to as to maintain pawls 242a, 242b in axial registration with V-shaped channels 232c, 232d and rack member 241.

Similar to ratchet mechanism 144, ratchet mechanism 244 includes a snap-over spring 143, in the form of a coil spring, interposed between pawls 242a, 242b and extending over and across a slot defined in rack member 241. Snap-over spring 143 has a length sufficient to urge each pawl 242a, 242b into respective V-shaped channels 232c, 232d of lower channel 230.

Snap-over spring 143 functions to maintain the teeth of pawls 242a, 242b in engagement with the respective rack teeth 241a, 241b of rack member 241 as rack member 241 is axially translated. When pawls 242a, 242b are in a first position (permitting drive channel 240 to move in a distal direction), snap-over spring 243 bulges in a proximal direction, and when pawls 242a, 242b are in a second position (permitting drive channel 240 to move in a proximal direction), snap-over spring 143 bulges in a distal direction.

In operation, when drive channel 240 is moved to the distal-most position, a distally oriented surface of rack member 241 engages distally bulging snap-over spring 143 to reverse the direction of buckling thereof, and thus reverse or change the orientation of pawls 242a, 242b. Additionally, when drive channel 240 is moved to the proximal-most position, a proximally oriented surface of rack member 241 engages proximally bulging snap-over spring 143 to again reverse the direction of buckling thereof, and thus again reverse or change the orientation of pawls 242a, 242b.

Clip applier 100 may also include audible/tactile indication or feedback with lower channel 230 and pawls 242a, 242b, when pawls 242a, 242b are flipped at either end of the stroke of drive channel 240. In particular, when pawls 242a, 242b flip, pawls 242a, 242b are accelerated by snap-over spring 243 and slap against the walls of respective V-shaped channels 232c, 232d of lower channel 230, thereby providing the user feedback that end of a stroke has been reached.

Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

The invention claimed is:

1. A surgical clip applier, comprising:
   a housing;
   a handle connected to the housing;
   a channel assembly extending from the housing;
   a clip carrier disposed within the channel assembly and defining a channel;
   a plurality of clips loaded in the channel of the clip carrier;
   a drive channel supported in the housing and the channel assembly; and
   a ratchet mechanism including:
      a rack member associated with the drive channel;
      a first pawl and a second pawl supported in the housing adjacent to the rack member; and
      a spring interposed between the first pawl and the second pawl, the spring coupled to the first pawl and to the second pawl, the spring configured to enable movement of the rack member and to approximate the first and second pawls toward the rack member.

2. The surgical clip applier of claim 1, further comprising a clip follower movably disposed within the channel of the clip carrier.

3. The surgical clip applier of claim 2, further comprising a biasing member positioned to urge the clip follower in a distal direction.

4. The surgical clip applier of claim 3, wherein the clip follower is incrementally advanceable to urge the plurality of clips into a pair of jaws.

5. The surgical clip applier of claim 4, further comprising a clip pusher bar positioned within at least one of the housing and the channel assembly.

6. The surgical clip applier of claim 5, wherein the pusher bar has a first end portion operatively connected to the handle and a second end portion defining a pusher.

7. The surgical clip applier of claim 6, wherein the pusher bar is movable away from the pair of jaws as the handle is actuated in order to move the pusher behind a distal-most clip of the plurality of clips.

8. The surgical clip applier of claim 7, wherein the pusher bar is configured to move towards the pair of jaws as the handle returns to an un-actuated position to move the distal-most clip between the pair of jaws.

9. The surgical clip applier of claim 8, further comprising a linkage mechanism that couples the drive channel to the pusher bar, the linkage mechanism having a driver link arm pivotally connected to a driven link arm.

* * * * *